(12) United States Patent
Naldini et al.

(10) Patent No.: US 7,833,789 B2
(45) Date of Patent: Nov. 16, 2010

(54) MONOCYTE CELL

(75) Inventors: Luigi Naldini, Milan (IT); Michele De Palma, Milan (IT); Mary Anna Lucia Venneri, Milan (IT)

(73) Assignees: Fondazione Centro San Raffaele del Monte Tabor, Milan (IT); Fondazione Telethon, Rome (IT)

( * ) Notice: Subject to any disclaimer, the term of this patent is extended or adjusted under 35 U.S.C. 154(b) by 66 days.

(21) Appl. No.: 11/831,248

(22) Filed: Jul. 31, 2007

(65) Prior Publication Data

US 2008/0057043 A1 Mar. 6, 2008

Related U.S. Application Data

(60) Provisional application No. 60/821,059, filed on Aug. 1, 2006.

(51) Int. Cl.
*C12N 5/00* (2006.01)
*C12N 5/08* (2006.01)

(52) U.S. Cl. ...................... 435/372; 435/325

(58) Field of Classification Search .............. 435/325, 435/372
See application file for complete search history.

(56) References Cited

U.S. PATENT DOCUMENTS

2003/0077249 A1* 4/2003 Bebbington et al.

OTHER PUBLICATIONS

Fujiyama et al., 2003, Circulation Research, vol. 93, p. 980-989.*
Weber et al., 2000, Journal of Leukocyte Biology, vol. 67, p. 699-704.*
Taussig et al., "Hematopoietic stem cells express multiple myeloid markers: implications for the origin and targeted therapy of acute myeloid leukemia," *Blood*, vol. 106, p. 4086-4092 (2005).
Wild et al., "Quantitative Assessment of Angiogenesis and Tumor Vessel Architecture by Computer-Assisted Digital Image Analysis: Effects of VEGF-Toxin Conjugate on Tumor Microvessel Density," *Microvascular Research*, vol. 59, p. 368-376 (2000).
Arai et al., "Tie2/Angiopoetin-1 Signaling Regulates Hematopoietic Stem Cell Quiescence in the Bone Marrow Niche," *Cell*, vol. 118, p. 149-161 (2004).
Elsheikh et al., "Only a specific subset of human peripheral-blood monocytes has endothelial-like functional capacity," *Blood*, vol. 106, p. 2347-2355 (2005).
Gordon et al., "Monocyte and Macrophage Heterogeneity," *Nature Reviews Immunology*, vol. 5, p. 953-964 (2005).
Jones et al., "The Receptors: New Modulators of Angiogenic and Lymphangiogenic Responses," *Nature Reviews Molecular Cell Biology*, vol. 2, p. 257-267 (2001).
Lemieux et al., "Angiopoietins can directly activate endothelial cells and neutrophils to promote proinflammatory responses," *Blood*, vol. 105, p. 1523-1530 (2005).
Rafii et al., "Vascular and Haematopoietic Stem Cells: Novel Targets for Anti-Angiogenesis Therapy?" *Nature Reviews Cancer*, vol. 2, p. 826-835 (2002).
De Palma et al., "Tie 2 identifies a hematopoietic lineage of proangiogenic monocytes required for tumor vessel formation and a mesenchymal population of pericyte progenitors," *Cancer Cell*, vol. 8, p. 211-226 (2005).

* cited by examiner

*Primary Examiner*—Shin-Lin Chen
(74) *Attorney, Agent, or Firm*—Steptoe & Johnson LLP

(57) ABSTRACT

The present invention relates to human and mouse monocyte cells expressing Tie2 and CD14 or CD16 and their use in methods for regulating angiogenesis and vascular integrity, such as methods of inducing angiogenesis, promoting vessel growth or stabilization, treating pathological disorders, inhibiting angiogenesis, and diagnosing or monitoring a pathological disorder.

10 Claims, 48 Drawing Sheets

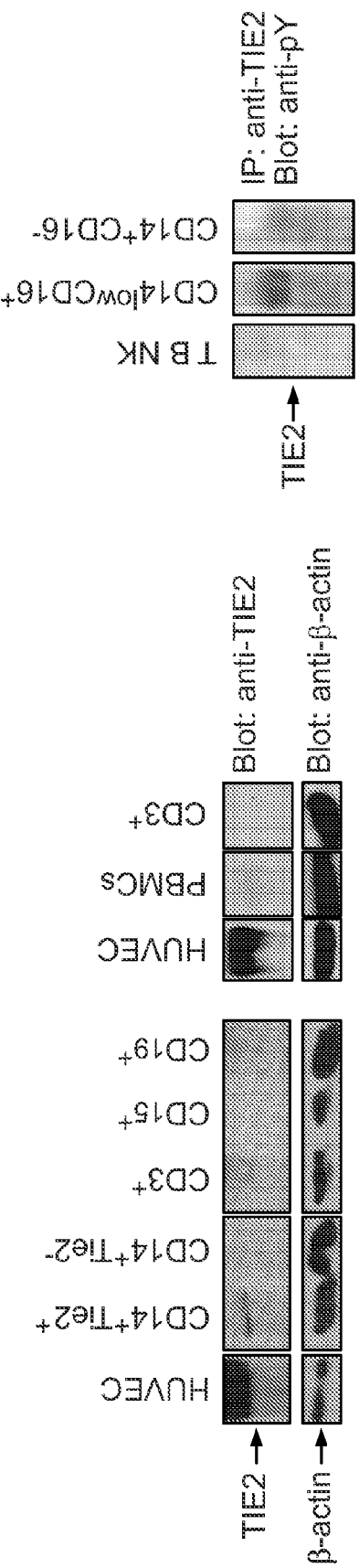

|            | WBC  | RBC  | HGB  | HCT  | PLT    |
|------------|------|------|------|------|--------|
| Tie2-GFP 2 | 4,2  | 10,5 | 15,7 | 54,6 | 1175   |
| Tie2-GFP 4 | 4,8  | 9,13 | 14   | 46,7 | 1263   |
| Tie2-GFP 5 | 5,2  | 9,92 | 15,4 | 51,4 | 1313   |
| PGK-GFP 1  | 3,2  | 9,8  | 14,5 | 50,4 | 1022   |
| PGK-GFP 2  | 4,6  | 10,2 | 14,9 | 52   | 1216   |
| PGK-GFP 3  | 4,1  | 11   | 15,4 | 53,7 | 1198   |
| Mean       | 4,4  | 10,1 | 15,0 | 51,5 | 1197,8 |
| SD         | 0,69 | 0,64 | 0,64 | 2,79 | 99,28  |
| Tie2-IFN 1 | 3,3  | 9,1  | 13,8 | 46,7 | 1060   |
| Tie2-IFN 2 | 4    | 9,7  | 14,9 | 50,8 | 1020   |
| Tie2-IFN 3 | 5,7  | 10,4 | 16,3 | 54,1 | 1043   |
| Tie2-IFN 4 | 3,1  | 10,6 | 15,8 | 49,1 | 1216   |
| Tie2-IFN 5 | 3,7  | 11,3 | 16,8 | 55,5 | 1221   |
| Tie2-IFN b2| 1,8  | 9    | 13,5 | 47   | 1863   |
| Tie2-IFN b3| 3,6  | 9,2  | 14,1 | 48,6 | 998    |
| Tie2-IFN b5| 5,5  | 9,9  | 14   | 50,9 | 1355   |
| Mean       | 3,8  | 9,9  | 14,9 | 50,3 | 1222,0 |
| SD         | 1,27 | 0,82 | 1,25 | 3,17 | 287,32 |
| s-IFN 1    | 3,9  | 8,8  | 13,5 | 45,8 | 620    |
| s-IFN 2    | 1,9  | 7,7  | 11,5 | 38,7 | 156    |
| s-IFN 3    | 4,2  | 9,1  | 14,4 | 48,9 | 539    |
| s-IFN 4    | 1,3  | 4,3  | 6,6  | 20,5 | 56     |
| Mean       | 2,8  | 7,5  | 11,5 | 38,5 | 342,8  |
| SD         | 1,25 | 1,91 | 3,02 | 11,02| 241,08 |

| t test          | WBC    | RBC    | HGB    | HCT    | PLT    |
|-----------------|--------|--------|--------|--------|--------|
| GFP/Tie2-IFN    | 0,3922 | 0,6439 | 0,8849 | 0,5015 | 0,8481 |
| GFP/s-IFN       | 0,0524 | 0,0226 | 0,0393 | 0,0378 | 0,0001 |
| Tie2-IFN/s-IFN  | 0,2404 | 0,0170 | 0,0289 | 0,0266 | 0,0005 |

Figure 11I

MONOCYTE CELL

CLAIM OF PRIORITY

This application claims priority to provisional U.S. Patent Application No. 60/821,059, filed Aug. 1, 2006, which is incorporated by reference in its entirety.

FIELD OF THE INVENTION

The present invention relates to human and mouse monocyte cells and their use in methods for regulating angiogenesis and vascular integrity, such as methods of inducing angiogenesis, promoting vessel growth or stabilization, treating pathological disorders, inhibiting angiogenesis, and diagnosing or monitoring a pathological disorder. The present invention also relates to a method of screening for a modulator of angiogenesis, vessel growth, or vessel stabilization. The present invention further relates to a method of gene delivery using the monocyte cells of the present invention.

BACKGROUND OF THE INVENTION

The term "angiogenesis" (also referred to as "neovascularization") is a general term used to denote the growth of new blood vessels both in normal and pathological conditions.

Angiogenesis is an important natural process that occurs during embryogenesis, fetal and post-natal growth and in the adult healthy body in the process of wound healing, and in restoration of blood flow back into injured tissues. In females, angiogenesis also occurs during the monthly reproductive cycle to build up the uterus lining and to support maturation of oocytes during ovulation, and in pregnancy when the placenta is formed, in the process of the establishment of circulation between the mother and the fetus.

In the therapeutic field, there has been in recent years a growing interest in the control of angiogenesis. In one aspect, the aim was to control or diminish excessive and pathological angiogenesis that occurs in diseases such as cancer, diabetic blindness, age related macular degeneration, rheumatoid arthritis, psoriasis, and additional conditions. In these pathological conditions the new blood vessels feed the diseased tissue, for example the tumor tissue, providing it with essential oxygen and nutrients thus enabling its pathological growth. In addition, the pathological angiogenesis may destroy the normal tissue. Furthermore, the new blood vessels, formed for example in the tumor tissue, enable the tumor cells to escape into the circulation and metastasize in other organs.

Typically, excessive angiogenesis occurs when diseased cells produce abnormal amounts of angiogenetic growth factors, overwhelming the effect of the natural angiogenesis inhibitors present in the body.

Anti-angiogenetic therapies developed recently, are aimed at preventing new blood vessel growth through the targeting and neutralization of any of the stimulators that encourage the formation of new blood vessels.

A contrasting indication of regulating angiogenesis is the stimulation of production of neovascularization in conditions where insufficient angiogenesis occurs. Typically, these conditions are diseases such as coronary artery diseases, stroke, and delayed wound healing (for example in ulcer lesions). In these conditions, when adequate blood vessels growth and circulation is not properly restored, there is a risk for tissue death due to insufficient blood flow. Typically, insufficient angiogenesis occurs when the tissues do not produce adequate amounts of angiogenetic growth-factors, and therapeutic angiogenesis is aimed at stimulating new blood vessels' growth by the use of growth factors or their mimics.

The main goal of the angiogenesis therapy is to produce a biobypass—i.e., to physically bypass diseased or blocked arteries, by stimulating the body into building new blood vessels.

Tie2 is a receptor tyrosine-kinase for the endothelium growth factor angiopoietin 2. Its expression is mainly restricted to endothelial cells. Tie2 has been shown to be involved in tumor related angiogenesis and the use of modulators of Tie2 has been proposed in, for example, WO2004/006862, WO02/060382, WO01/44460 and WO00/18437.

Nevertheless there is a continuing need to provide treatments for disorders associated with excessive angiogenesis or for promoting new blood vessel growth. The present invention seeks to provide such a solution.

In addition, there is a need to provide a way of monitoring the extent of ongoing angiogenesis in a patient, particularly a patient undergoing treatment. The present invention seeks to provide such a method.

SUMMARY OF THE INVENTION

We have determined the phenotype of Tie2-expressing monocytes (TEMs). Our findings provide novel and surprising insights into the cellular mechanisms of tumor vessel formation and may be used in the design and monitoring of novel therapies.

Surprisingly we have found that, with the exception of Tie2 and CD11b, Hu-TEMs display distinct and unpredictable surface markers from their mouse counterpart.

Furthermore, human circulating proangiogenic monocytes are a unique population of monocytes distinguishable from classical proinflammatory monocytes, and with tissue remodeling activity (pro-angiogenic).

In more detail, human monocytes can be divided into two main subsets, according to the presence and expression level of the following surface markers: $CD14^{high}CD16^-$ inflammatory monocytes (or classical monocytes) and $CD14^+CD16^+$ monocytes. Whereas the former are believed to be involved in innate inflammatory responses directed against pathogens, the latter comprise cells endowed with tissue remodelling activity and marked migration ability, possibly representing the precursors of tissue-resident macrophages. We have found that the $Tie2^+$ monocytes are a subset of $CD14^+CD16^+$ monocytes and are excluded from the $CD14^{high}$ population. Thus, based on the expression level of CD14, we refer to these cells as $CD14^{low}$. We further investigated the phenotype of circulating huTEMs and found that they were mostly $CD11b^+$, $CCR5^+$, $CD33^+$, L-selectin $(CD62L)^-$ and $CCR2^-$. Interestingly, huTEMs uniformly expressed the mouse colony stimulating factor receptor (M-CSFR, also known as CD115), a receptor involved in the recruitment of monocytes to tumors. Overall, the phenotype of huTEMs strongly suggests that they represent a unique subset of monocytes different from classical proinflammatory cells.

STATEMENTS OF THE INVENTION

According to a first aspect of the present invention there is provided a human monocyte cell characterised by the expression of the following markers: Tie2 and CD14.

According to another aspect of the present invention there is provided a human monocyte cell characterised by the expression of the following markers: Tie2 and CD16.

According to another aspect of the present invention there is provided a human monocyte cell characterised by the expression of the following markers: Tie2, CD14 and CD16.

According to another aspect of the present invention there is provided a human monocyte cell characterised by the expression of the following markers: Tie2, CD14, CD16, CD115 and CD33.

According to another aspect of the present invention there is provided a human monocyte cell characterised by the expression of the following markers: Tie2, CD11b, CD14, CD16, CD45, CD115, CD33 and CCR5.

Preferably the human monocyte cell does not express the CCR2 marker.

Preferably the human monocyte cell does not express the following markers: CCR2, CD62L, CD19 and CD3.

Preferably the human monocyte cell is characterised by the expression of the following markers: Tie2, CD11b, CD14, CD16, CD45, CD115, CD33 and CCR5; and wherein the cell does not express the following markers: CCR2, CD19, CD3, and CD62L.

Preferably the human monocyte cell is not a $CD14^{high}CD16^-$ classical monocyte.

According to another aspect of the present invention there is provided a mouse monocyte cell characterised by the expression of the following markers: Tie2 and CD11b.

According to another aspect of the present invention there is provided a mouse monocyte cell characterised by the expression of the following markers: Tie2 and CD45.

According to another aspect of the present invention there is provided a mouse monocyte cell characterised by the expression of the following markers: Tie2, CD11b and CD45.

Preferably the mouse monocyte cell does not express the Gr-1 marker.

Preferably the mouse monocyte cell does not express the following markers: Gr-1, c-Kit, CD19, CD3.

Preferably the mouse monocyte cell is characterised by the expression of the following markers: Tie2, CD11b and CD45 and wherein the cell does not express the following markers Gr-1, c-Kit, CD19, CD3.

In a preferred embodiment the monocyte cell of the present invention promotes angiogenesis.

In another preferred embodiment the monocyte cell of the present invention promotes cell migration.

In one embodiment the monocyte cell of the present invention comprises a nucleotide sequence of interest (NOI).

The NOI may be encoded within a vector, preferably a viral vector, more preferably a lentiviral vector.

Preferably the NOI encodes a therapeutic protein or a therapeutic RNA such as, but not limited to, a pro-angiogenic agent, an anti-angiogenic agent or an anti-cancer agent.

The cell of the invention may be obtained from hematopoietic precursor cells.

Preferably, the cell of the invention is an isolated cell.

According to another aspect of the present invention there is provided a composition comprising a monocyte cell of the present invention.

According to another aspect of the present invention there is provided a composition comprising a population of cells, wherein said population consists essentially of monocyte cells of the present invention. Preferably the composition is substantially free of other cell types such as classical human monocytes. Preferably the cells making up the composition comprise at least 50%, preferably at least 60%, more preferably at least 70%, more preferably at least 80%, more preferably at least 90%, more preferably at least 95%, more preferably at least 97%, more preferably at least 99% (by number) cells of the present invention.

Preferably said composition is a pharmaceutical composition comprising a pharmaceutically acceptable carrier, dilute or excipient.

According to another aspect of the present invention there is provided a method of inducing angiogenesis comprising delivering a monocyte cell or composition of the present invention in an amount effective to induce angiogenesis.

According to another aspect of the present invention there is provided a method for treating or preventing a disorder in a subject comprising administering a monocyte cell or composition of the present invention in an amount effective to treat the disorder by inducing angiogenesis.

Preferably the disorder is selected from the group comprising cardiac ischemia, atherosclerosis, diabetes, lower limb ischemia, renal vascular disease, a wound, unvascularized tissue related to grafts and transplants, and stroke.

According to another aspect of the present invention there is provided a method of promoting vessel growth or stabilisation comprising administering a monocyte cell and/or its precursor and/or a composition of the present invention in an amount effective to promote vessel growth or stabilisation.

According to another aspect of the present invention there is provided a method of diagnosing or monitoring the angiogenic phenotype in a subject comprising determining the presence or amount of a monocyte cell of the present invention or the markers characterizing a monocyte cell according to the present invention in a biological sample.

According to another aspect of the present invention there is provided a method of diagnosing or monitoring a disorder in a subject comprising determining the presence or amount of a monocyte cell of the present invention or the markers characterizing a monocyte cell according to the present invention in a biological sample.

Preferably the disorder is cancer or a disorder selected from the group consisting of cardiac ischemia, atherosclerosis, renal vascular disease, stroke, a wound, placental insufficiency, unvascularized tissue related to grafts and transplants, rheumatoid arthritis, diabetes, disorders relating to endothelial cell apoptosis or necrosis, hemangiomas and proliferative retinopathy.

According to another aspect of the present invention there is provided a method for treating or preventing cancer in a subject comprising administering a monocyte cell and/or its precursor expressing an anti-angiogenic agent or composition comprising the same in an effective amount.

According to another aspect of the present invention there is provided a method for treating or preventing angiogenesis in a subject comprising administering a monocyte cell or composition of the present invention in an effective amount.

The angiogenesis may be associated with, for example, tumor vascularization, retinopathies (e.g., diabetic retinopathy), rheumatoid arthritis, Crohn's disease, atherosclerosis, hyperstimulation of the ovary, psoriasis, endometriosis associated with neovascularization, restenosis due to balloon angioplasty, tissue overproduction due to cicatrization, peripheral vascular disease, hypertension, vascular inflammation, Raynaud's disease and phenomena, aneurism, arterial restenosis, thrombophlebitis, lymphangitis, lymphedema, tissue cicatrization and repair, ischemia, angina, myocardial infarction, chronic heart disease, cardiac insufficiencies such as congestive heart failure, age-related macular degeneration and osteoporosis.

According to another aspect of the present invention there is provided a method of screening a candidate agent for the ability to modulate angiogenesis comprising the steps of:

Exposing cells capable of forming blood vessels to a monocyte cell of the present invention in the presence and absence of the candidate agent;

measuring the angiogenic activity of the cells capable of forming blood vessels;

wherein a change in the angiogenic activity of the cells capable of forming blood vessels in the presence of the candidate agent relative to the activity in the absence of the candidate agent indicates that the candidate agent is a modulator of angiogenesis.

Preferably the cells capable of forming blood vessels are endothelial cells.

The angiogenic activity may be measured by any suitable method known in the art, such as, but not limited to, counting branch points from tubes formed between discrete endothelial cells.

In one embodiment the method comprises screening for an agent which inhibits angiogenesis.

In another embodiment the method comprises screening for an agent which promotes angiogenesis.

According to another aspect of the present invention there is provided an agent capable of modulating angiogenesis obtained by the screening method of the present invention.

The agent obtained by the screening may be used in the treatment or prevention of a pathological disease associated with angiogenesis.

According to another aspect of the present invention there is provided a method of screening a candidate agent for the ability to inhibit tumor angiogenesis comprising the steps of:

Exposing tumour cells to a monocyte cell of the present invention in the presence and absence of the candidate agent;

measuring the tumor angiogenesis;

wherein a decrease in the tumor angiogenesis in the presence of the candidate agent relative to the absence of the candidate agent indicates that the candidate agent inhibits tumor angiogenesis.

According to another aspect of the present invention there is provided an agent capable of inhibiting tumor angiogenesis obtained by the screening method of the present invention.

The agent obtained by the screening may be used in the treatment or prevention of cancer.

According to another aspect of the present invention there is provided a method of inhibiting angiogenesis which includes delivering an inhibitor of the monocyte cell of the present invention in an amount effective to inhibit angiogenesis.

According to another aspect of the present invention there is provided a method of delivering a gene to target cells in a subject, wherein said target cells are engaged in angiogenesis in a pathological condition (e.g., cancer), and expressing the gene in said cells, comprising transducing bone marrow-derived hematopoietic progenitor cells with a vector comprising said gene under the control of the Tie2 regulatory sequences.

Preferably, the regulatory sequences are sequences from the intronic and promoter regions of at least human Tie2. Examples of Tie2 regulatory sequences for use in the present invention are described in EP1264892A2. The intronic enhancer sequence of the mTie2 gene may be placed upstream to the promoter. Other possible examples are lentiviral constructs that comprise the intronic enhancer sequence of the Tie2 gene in another position, such as upstream to the transgene between the cPPT and the promoter, in the vector LTR or downstream to the transgene.

Preferably the vector is derived from a lentivirus.

Preferably the bone marrow-derived hematopoietic progenitor cells are transduced ex-vivo followed by transplantation into the subject.

Preferably the gene is a NOI that encodes an anticancer agent. In one embodiment, the NOI is a cytokine, preferably IRN, more preferably IFN-alpha.

According to another aspect of the present invention there is provided a method for screening for monocyte cells of the present invention in a population of cells comprising screening the population of cells for the markers expressed by any one of the monocyte cells of the present invention. The population of cells may be derived from hematopoietic precursor cells.

According to another aspect of the present invention there is provided monocyte cells of the present invention obtained from hematopoietic precursor cells.

Advantages of the use of TEMs in accordance with the present invention include the following:

Among other circulating Tie2+ cells such as circulating endothelial cells (CECs), TEMs should represent ideal candidates to monitor/target angiogenesis, for the following reasons:

TEMs are more abundant in the peripheral blood than the elusive CECs.

TEMs can be easily distinguished from other hematopoietic cells subsets by the combination of (at least two) surface markers (Tie2 and either CD14 or CD16). This combination of markers distinguishes huTEMs from related hematopoietic cell populations, including inflammatory monocytes, mast cells, hematopoietic progenitors and CECs.

TEMs circulate in the peripheral blood, thus they may be assayed by a simple procedure. Furthermore, TEMs increase in the peripheral blood of mice following angiogenic stimulation, such as the systemic injection of conditioned medium from tumor cell cultures. Thus, TEMs may serve as a quantitative pharmacodynamic marker to monitor the angiogenic phenotype in a living organism or a patient and the effectiveness of antiangiogenic therapies.

TEMs have superior proangiogenic activity among a number of hematopoietic cell populations tested, including classical inflammatory monocytes. Furthermore, TEMs are committed to a proangiogenic function already when they circulate in the peripheral blood, appearing to be a distinct lineage of previously unknown cells with dedicated (proangiogenic) function. Thus, TEMs may be targets of novel cancer therapies.

TEMs may be used to identify novel molecular targets of existing and novel drugs (several anticancer drugs that have myelosuppressive activity may be more active on tumors as compared to normal proliferating tissues because they also target proangiogenic myeloid cells required for tumor growth).

DETAILED DESCRIPTION

Figure 1A:
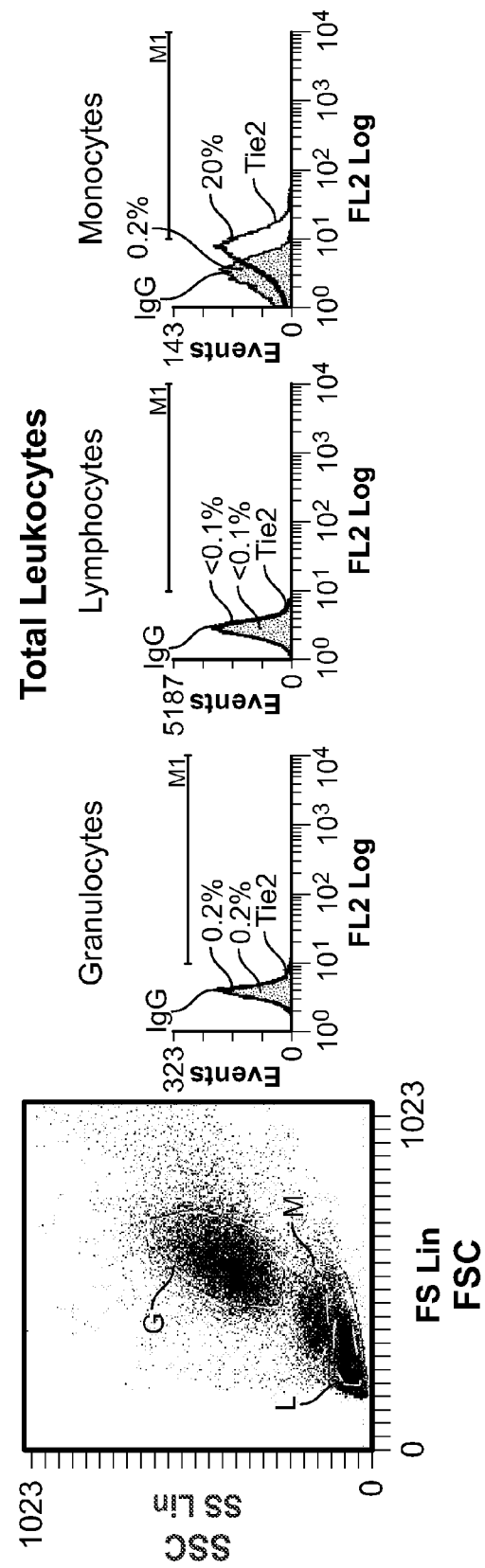
FIG. 1: A) Flow cytometry analysis of PB granulocytes (G), lymphocytes (L) and monocytes (M) identified on the basis of physical gating (dot plot on the left; gates indicated by dashed line) shows TIE2 expression in a subset of monocytes (open line in the histogram plots on the right; filled line IgG isotype control). Percentages of marker-positive cells are indicated. (B) The TIE2$^+$ cells are a small fraction of the total PBMCs (gate in right panel). Representative analysis of at least 16 performed on different donors. (C) The vast majority of TIE2$^+$PBMCs do not express the CEC/EPC markers AC133 and CD146. Rare TIE2$^+$AC133$^+$ and TIE2$^+$CD146$^+$ cells may represent EPCs and CECs, respectively. Similar findings were obtained on 2 different PBMC samples. (D) A small subset of TIE2$^+$ cells are VEGFR-2$^+$CD14$^+$, likely representing previously described monocytes with endothelial-like functional capacity. (E) and (F) PBMCs were stained with FITC-conjugated anti-CD14, PC5-conjugated anti-CD16, biotinylated anti-Tie2 or IgG1 isotypic control, followed by PE-conjugated Streptavidin. Biotinylated anti-IL2Ra followed by PE-conjugated Streptavidin was used as a irrelevant control antibody. Expression of CD14 and CD16 (dot plot on the top right) identifies two distinct monocyte subsets (see Examples). The gated cell populations (stained in different colors) were analysed for expression of TIE2 and IL2Ra versus isotype control. Note that the CD14$^{low}$CD16$^+$ fraction (resident monocytes; red dots) is highly enriched in TIE2$^+$ cells, whereas the CD14$^{high}$CD16$^-$ fraction (inflammatory monocytes; blue dots) contains much fewer TIE2$^+$ cells. CD14$^-$ cells (green and pink dots) mainly represent B and natural killer cells, and are mostly TIE2$^-$. Representative analysis of at least 6 experiments performed on different donors. Similar results were obtained using a PE-conjugated anti-TIE2 antibody.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; and E. M. Shevach and W. Strober, 1992 and periodic supplements, Current Protocols in Immunology, John Wiley & Sons, New York, N.Y. Each of these general texts is herein incorporated by reference.

Haematopoietic cells of diverse lineages contribute to tumour development (Coussens et al., Nature. 2002; 420:860-867; de Visser et al., Nat Rev Cancer. 2006; 6:24-37). Among these cells, tumour-associated macrophages (TAMs) play important roles in tumourigenesis (Condeelis et al., Cell. 2006; 124:263-266; Lewis et al., Cancer Res. 2006; 66:605-612). TAMs are believed to derive from circulating monocytes, which differentiate into macrophages upon homing to tumours. In tumours, TAMs may exert dichotomical functions. TAMs may indeed eliminate tumour cells and stimulate antitumour immunity (Griffith et al., J Exp Med. 1999; 189: 1343-1354; Dranoff et al., Nat Rev Cancer. 2004; 4:11-22) but increasing data suggest that they also exhibit protumoural functions, including tuning down antitumour immunity and stimulating angiogenesis, cell migration, invasion and metastasis (Condeelis et al., Cell. 2006; 124:263-266; Lewis et al., Cancer Res. 2006; 66:605-612; Pollard et al., Nat Rev Cancer. 2004; 4:71-78; Balkwill et al., Cancer Cell. 2005; 7:211-217). Although the divergent TAMs' functions (i.e. antitumoural and protumoural activities) are contextually modulated by the tumour microenvironment (Balkwill et al., Cancer Cell. 2005; 7:211-217), emerging data suggest the existence of distinct monocyte subsets committed to growth-promoting, proangiogenic and protumoural activities.

It has been recently emphasised that myeloid-lineage cells promote tumour angiogenesis (De Palma et al., Cancer Cell. 2005; 8:211-226; Coussens et al., Genes Dev. 1999; 13:1382-1397; De Palma et al., Nat. Med. 2003; 9:789-795; Yang et al., Cancer Cell. 2004; 6:409-421; Conejo-Garcia et al., Blood. 2005; 105:679-681; Kopp et al., Curr Opin Hematol. 2006; 13:175-181). In this regard, we identified in mouse tumour models a subset of tumour-infiltrating monocytes characterised by the expression of the angiopoietin receptor Tie2, a molecule previously known to be restricted to endothelial and haematopoietic stem cells. Tie2-expressing monocytes (TEMs) preferentially home to tumours, where they are required for angiogenesis. Indeed, TEM elimination by a suicide gene completely prevented human glioma neovascularization in the mouse brain and induced substantial tumour regression. Inhibiting the activities of proangiogenic myeloid cells may therefore represent a valuable anticancer strategy. The rationale for this approach obtains major support from our identification and functional characterization of putative proangiogenic myeloid cells in humans.

We have found that Tie2 expression in human peripheral blood identifies a novel subset of monocytes endowed with marked proangiogenic activity. These cells have unique features among monocytes, because they are distinct from classical proinflammatory monocytes and express a distinguishing combination of surface markers, which overlaps only in part with that of their mouse counterpart and thus could not be anticipated from previous studies. Remarkably, these human Tie2-expressing monocytes are preferentially recruited to tumours among a variety of tissues analysed, where they constitute the pre-eminent population of monocytes distinct from common TAMs. Our results highlight a potential critical role of Tie2$^+$ monocytes cells in human cancer progression. The present invention may therefore be used to identify novel biomarkers and targets of anti-angiogenic therapy, thus opening the way to the design of novel drugs that inhibit tumour angiogenesis and growth.

We have identified a novel subset of circulating proangiogenic monocytes based on the expression of a distinguishing combination of cell surface markers, including Tie2, CD14 and CD16. Both in mouse and human PB, TEMs are a small subset of circulating and tumour-infiltrating monocytes characterised by the expression of the angiopoietin receptor Tie2, a molecule previously known to be restricted to ECs and haematopoietic stem cells. We detected TEMs in several mouse tumour models—including subcutaneous tumour grafts, orthotopically growing gliomas and spontaneous pancreatic tumours—where they represent 1-15% of the total CD11b$^+$ myeloid HCs. A peculiar feature of TEMs is that they preferentially localise around angiogenic blood vessels in tumours, a figure that is consistent with their marked proangiogenic activity in transplantation assays.

We propose that TEMs are distinct from common TAMs based on their surface marker profile, which overlaps with that of previously described resident monocytes, a population of immature monocytes. Remarkably, we found that huTEMs were effectively recruited to human carcinomas and directly promoted angiogenesis in in vivo assays, pointing to a novel function of resident monocytes in tumor angiogenesis. Interestingly, we believe that classical inflammatory monocytes, which represent the major monocyte population in PB, were less proangiogenic than huTEMs in vivo.

We believe that only a fraction of resident monocytes expressed Tie2, indicating that these cells have a certain degree of phenotypical and functional heterogeneity. HuTEMs can be identified in PB as Tie2$^+$CD14$^{low}$CD16$^+$ CD115$^+$CD33$^+$CCR2$^-$ cells, although the expression of Tie2 and CD14 (or CD16) would be, in principle, sufficient to identify these cells in PB. Preferably the HuTEMs of the present invention have all of these above mentioned markers in combination as this preferably identifies proangiogenic monocytes.

Other circulating cells have been previously described that appeared to contribute to (tumour) angiogenesis. Among these cells there are the so-called CECs or endothelial progenitor cells (EPCs). Kerbel and colleagues proposed that the frequency of VEGFR-2$^+$ c-Kit$^+$ or VEGFR-2$^+$CD146$^+$ CECs/EPCs in human peripheral blood may serve as a quantitative pharmacodynamic marker to monitor i) the angiogenic phenotype, i.e. the type and magnitude of angiogenesis, in a living organism or a patient and ii) the effectiveness of anti-angiogenic therapies. Indeed, CECs are significantly increased in experimentally induced angiogenesis and are conversely decreased during antiangiogenic therapy. These observations suggested the possibility of using CECs as surrogate markers to monitor both angiogenesis and antiangiogenic drug activity and to identify the optimal biologic dose of such drugs. However, the concept of "CEC" has become the subject of intense debate, not only because there is no consensus on the cell surface marker profile that identifies these cells, but also because the existence of these rare cells and their functional role in angiogenesis has been questioned by several investigators. In the determination of CECs in peripheral blood, it should be taken in account that haematopoietic cells and endothelial cells share phenotypical and functional features, including the expression of common metabolic and surface markers. Markers that are co-expressed by ECs and HC subsets include VEGFR-1, Sca-1, Tie2, AC133, CD31 (PECAM-1), von Willebrand Factor and CD146 (S-endo-1 or P1H12). Unfortunately, virtually no surface marker is uniquely expressed by endothelial cells, thus making the identification of CECs rather problematic. For these reasons, the use of the proangiogenic haematopoietic cells of the present invention, rather than CECs, may be used as more reliable and biologically relevant quantitative pharmacodynamic markers to monitor angiogenesis and the effectiveness of antiangiogenic therapies.

Thus, the identification of the Tie2$^+$ monocytes of the present invention opens a number of avenues in the development of novel anticancer therapies. TEMs can be used as targets of novel antiangiogenic therapies. The identification of TEM-specific genes by a comparative analysis with other haematopoietic subsets would provide a panel of candidate molecular targets for the development of new drugs that selectively inhibit their activities.

TEMs can be used as surrogate markers to monitor the angiogenic phenotype (i.e. the extent of ongoing angiogenesis in a given patient), and the effectiveness of antiangiogenic therapies. This concept is supported by the observation that circulating TEMs are increased under angiogenic conditions.

Also, TEMs can be used as gene delivery vehicles in the setting of an autologous bone marrow transplant or adoptive transfer. Bone marrow progenitors or peripheral blood-derived haematopoietic cells could be engineered to express antiangiogenic genes under the control of Tie2 transcription regulatory elements, as shown for the delivery of type I interferon in a mouse model of glioma described below in example 5.

As the cells of the present invention are associated with angiogenesis, and are preferentially recruited to tumors, they provide a useful delivery system for pro-angiogenic, anti-angiogenic and anti-cancer agents and provide the advantage of reducing selective toxicity.

The NOI may encode a factor which stimulates angiogenesis such as (among others) VEGF, FGFs, IL-8, HGF/SF and PDGF. The NOI may also encode factors which inhibit angiogenesis, such as (among others) IL-10, IL-12, gro-[alpha] and gro-[gamma], platelet factor 4, angiostatin, the human chondrocyte derivative inhibitor, thrombospondin and the leukemia inhibitor. (Jensen, 1998 Surg. Neural., 49, 189-195; Tamatani et al., 1999, Carcinogenesis, 20, 957-962; Tanaka et al., 1998, Cancer Res., 58, 3362-3369; Ghe et al., 1997, Cancer Res., 57, 3733-3740; Kawahara et al., 1998, Hepatology, 28, 1512-1517; Chandhuni et al., 1997, Cancer Res., 57, 1814-1819; Jendraschak and Sage, 1996, Semin. Cancer Biol., 7, 139-146; Majewski et al., 1996, J. Invest. Dermatol., 106, 1114-1119).

The NOI may also encode a therapeutic RNA or nucleotide including but not limited to ribozymes, decoys, antisense and small interfering RNA (siRNA) or microRNA molecules. The therapeutic RNA may, for example, inhibit any of the aforementioned factors.

In particular, over the last few years, ribozymes, antisense and small siRNA technology has emerged as an exciting and promising strategy in the fight against cancer. The antisense concept is to selectively bind short, modified DNA or RNA molecules to messenger RNA in cells and prevent the synthesis of the encoded protein. As anticancer agents, ribozymes, antisense and small siRNA can be targeted against a myriad of genes involved in cell transformation, cell survival, metastasis, and angiogenesis. Indeed, the list of possible antisense targets increases as the knowledge of the genetic basis of oncogenesis expands (Kushner et al., Curr Oncol Rep. 2000 January; 2(1):23-30). A number of these compounds are currently in phase II trials, including those targeting protein kinase C-alpha, bcl-2, c-raf, and the R1-alpha subunit of protein kinase A.

Additional examples of anti-cancer genes to be delivered by TEMs include and are not limited to type I and type II interferons, Interleukin 10 and Interleukin 12, TRAIL, TNF, CXCL4, CXCL10, CXCL14, angiostatin, endostatin, thrombospondin, recombinant monoclonal antibodies and soluble receptors against angiogenic molecules. For a comprehensive list see review by Ruegg et al, BBA, 2006 (Biochim Biophys Acta. 2006 April; 1765(2):155-77).

The TEM may be engineered by procedures known in the art, including by use of a lentiviral particle containing a nucleotide sequence of interest (NOI), as shown in the example 5. Similarly, cells may be engineered in vivo for expression of an NOI. As the cells of the present invention are preferentially recruited to tumors, they provide a useful delivery system for anti-cancer agents and provide the advantage of reducing selective toxicity.

The present invention thus also relates to a method of gene delivery and selective expression in cells engaged in the angiogenesis of a tumor by introducing the above described engineered TEMs into the tumor mass.

Construction of appropriate expression vehicles and vectors for gene therapy applications will depend on the organ to be treated and the purpose of the gene therapy. The selection of appropriate promoters and other regulatory DNA will proceed according to known principles, based on a variety of known gene therapy techniques. For example, lentiviral and retroviral mediated gene transfer is a very effective method for gene therapy, as systems utilizing packaging defective viruses allow the production of recombinants which are infectious only once, thus avoiding the introduction of wild-type virus into an organism. Alternative methodologies for gene therapy include non-viral transfer methods, such as calcium phosphate co-precipitation, mechanical techniques, for example microinjection, membrane fusion-mediated transfer via liposomes, as well as direct DNA uptake and receptor-mediated DNA transfer.

Viral vectors which may be used to produce stable integration of genetic information into the host cell genome include vectors derived from lentiviruses, retroviruses, spumaviruses, adenoassociated virus (AAV). For a review on gene therapy vectors, see Kay, Glorioso and Naldini, Nature Medicine, 2001 (*Nat. Med.* 2001 January; 7(1):33-40).

The gene delivery and selective expression in cells engaged in tumor angiogenesis and in metastasis can be provided by injecting the engineered TEMs into the bloodstream via a peripheral vein or into the afferent vasculature of the tumor or of the region(s) affected by metastasis.

The present invention also relates to a method of gene delivery and selective expression in cells engaged in angiogenesis in a pathological condition by transducing the above described vectors into bone marrow-derived progenitor cells ex vivo followed by transplant into conditioned or unconditioned recipients. The pathological condition includes, but is not limited to, retinal neovascularization, and a chronic inflammatory disease.

The present invention also relates to a method of gene delivery and selective expression in cells engaged in the angiogenesis of a tumor and in metastasis by transduction of the above described vectors into bone marrow-derived progenitor cells ex vivo followed by transplantation into conditioned and unconditioned recipients.

In particular, according to the present invention, the gene is delivered in the TEMs or their hematopoietic progenitors ex vivo and the gene is selectively expressed in vivo in the TEMs.

It is also possible to use regulated vectors in combination with targeted expression, so that the expression of a therapeutic gene is temporally regulated, protecting against untoward effects of the therapy.

The vector according to the present invention can be used to express a transcription regulator, such as for example a tetracycline-dependent activator or repressor, selectively in cells engaged in angiogenesis, and would be combined with another vector containing the regulated expression cassette for the test or therapeutic genes.

By delivering a "suicide" gene such as HSVTK, it is possible to selectively eliminate the TEMs when used with an appropriate pro-drug, such as ganciclovir. This results in substantial inhibition of angiogenesis and slower tumor growth potentially without systemic toxicity.

Further information on how to target exogenous genes to a tumor angiogenesis by transplantation of genetically modified TEMs may be found in EP-A-1 264 892 and De Palma et al, (2003) Nature Medicine, 9(6): 789-795.

In accordance with the method of the present invention, the TEM of the present invention can be administered in vivo, intravenously, intramuscularly, intraperitoneally, subcutaneously, intracerebrally, into cerebral spinal fluid, or by instillation into hollow organ walls or newly vascularized blood vessels. It may be administered alone or with pharmaceutically or physiologically acceptable carriers, excipients, or stabilizers.

Preferably, the TEM, compositions and methods of the present invention are used in treatment and diagnosis on humans.

The TEM of the present invention may also be administered in injectable dosages by solution or suspension of TEM in a physiologically acceptable diluent with a pharmaceutical carrier. In general, water, saline, aqueous dextrose and related sugar solution, and glycols, such as propylene glycol or polyethylene glycol, are preferred liquid carriers, particularly for injectable solutions.

The present invention also relates to a method for treating a pathological disorder in a patient which includes administering a TEM of the invention in an amount effective to treat the pathological disorder by inducing angiogenesis in the manner described above.

In one embodiment, the pathological disorder is ischemic cardiopathy and/or cerebrovascular disorders caused by insufficient cerebral circulation.

Thrombi or emboli due to atherosclerotic or other disorders (e.g., arteritis or rheumatic heart disease) commonly cause ischemic arterial obstruction.

In another embodiment, the pathological disorder is a non-cardiac vascular disorder including atherosclerosis, renal vascular disease, and stroke.

In yet another embodiment, the pathological disorder is a wound. Such wounds include, but are not limited to, chronic stasis ulcers, diabetic complications, complications of sickle cell disease, thalassemia and other disorders of hemoglobin, and post-surgical wounds.

In a further embodiment, the pathological disorder is a condition of placental insufficiency. Such conditions include, but are not limited to, intrauterine growth retardation.

In yet a further embodiment, the pathological disorder unvascularized tissue related to grafts and transplants (see, e.g., PCT International Application No, WO 99/06073 to Isner, which is hereby incorporated by reference).

Another aspect of the present invention is a method of promoting vessel growth or stabilization which includes delivering an effective amount of a TEM in an amount effective to promote vessel growth or stabilization in the manner described above.

Yet another aspect of the present invention is a method for treating a pathological disorder in a patient which includes administering a TEM of the invention in an amount effective to treat the pathological disorder by promoting vessel growth or stabilization in the manner described above.

In a preferred embodiment, the pathological disorder relates to endothelial cell apoptosis or necrosis. An example of such a pathological disorder is vasculitis.

The present invention also relates to a method of inhibiting angiogenesis such as angiogenesis associated with a pathological disorder which includes delivering a recombinant TEM of the invention or an inhibitor of the TEM of the invention in an amount effective to inhibit angiogenesis.

In one embodiment, the pathological disorder of the present invention is a vascular proliferative disease. Suitable vascular proliferative diseases include hemangiomas and proliferative retinopathy.

In another embodiment, the pathological disorder is cancer.

Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma.

The present invention further relates to a method of screening for a modulator of angiogenesis, vessel growth, or vessel stabilization. Suitable methods include In Vitro HUVEC Tube Formation Assay and In Vivo Matrigel Plug Assay, such as are described in Eubank et al (2004) Immunity 21: 831-842 and DePalma et al (2005) Cancer Cell 8: 211-226.

Another aspect of the present invention is a method of diagnosing or monitoring a pathological disorder in a patient which includes determining the presence or amount of a TEM of the invention in a biological sample. For example, TEMs may be quantified in human blood by Fluorescence-Activated Cell Sorting (FACS), as described in example 2 below, and their level correlated to the extent of pathological angiogenesis or its inhibition by therapy.

Suitable pathological disorders include cardiac ischemia, atherosclerosis, renal vascular disease, stroke, a wound, placental insufficiency, unvascularized tissue related to grafts and transplants, disorders relating to endothelial cell apoptosis or necrosis, hemangiomas, proliferative retinopathy, and cancer.

In a preferred embodiment, the presence or amount of a TEMs of the invention in certain tissue, e.g., tumor cells, sclerotic vessels, and vascular channels surrounded by tumor cells, may be used as an early maker of tumor angiogenesis.

Determining the presence or amount of a TEM of the invention in a biological sample may be accomplished using methods known to those of ordinary skill in the art, such as flow cytometry or FACS.

Suitable biological samples include blood, cerebrospinal fluid, pathological fluid collections, urine, semen, tissue biopsy, and saliva.

Further features and embodiments of the present invention will now be described by way of non-limiting example with reference to the following Examples.

EXAMPLES

Example 1

Methods

Cell Purification and Cell Sorting

Human Cells:

PB was obtained from healthy volunteers following informed consent, according to the Declaration of Helsinki and a protocol approved by the H. San Raffaele Bioethical Committee. Total leukocytes were analysed after lysis of erythrocytes using ammonium chloride. PBMCs were isolated using Ficoll-Hypaque gradient. Granulocytes, T and B lymphocytes were positively selected by magnetic sorting (using CD15, CD3 or CD19 MicroBeads, respectively; Miltenyi). T cell-depleted PBMCs were negatively selected by CD3 MicroBeads. Resident monocytes ($CD16^+CD14^{low}$) were enriched from PBMCs by negative selection of T, B and NK cells (using a cocktail of CD3, CD19 and CD56 MicroBeads), followed by positive selection by CD16 MicroBeads. Inflammatory monocytes ($CD16^-CD14^+$) were enriched by negative selection of $CD16^+$ cells, followed by positive selection by CD14 MicroBeads. For cell sorting, we used a Becton Dickinson FACS Vantage SE-FACSDiVa equipped with Argon Ion and HeNe lasers and the Quadra-Sort option. Sorted populations included: $CD14^+TIE2^+$, $CD14^+TIE2^-$ and CD14+ monocytes (using FITC-conjugated anti-CD14 and PE-conjugated anti-TIE2 antibodies), and CD14+CD16+ and CD14+CD16− monocytes (using FITC-conjugated anti-CD14, PC5-conjugated anti-CD16 and PE-conjugated anti-TIE2 antibodies).

Flow Cytometry

Human Samples:

Blood cells and tumours reduced to single cell suspensions by collagenase digestion (De Palma et al., 2005) were processed for FACS analysis as it follows. Cells were blocked 1% BSA in phosphate buffered saline containing the FcR Blocking Reagent (Milteny), for 10 min at 4° C. After blocking, 1001 of the Fc-blocked cells ($10^5$ to $10^6$ cells) were stained with monoclonal anti-mouse antibodies (final concentration of 2-5 μg/mL) for 30 min at 4° C. The following antibodies were used: Biotinylated anti-Tie2 (5 μg/mL; cl. 9; from RELI-Atech), followed by PE-conjugated Streptavidin (1:500; from BD Pharmingen); Biotinylated IgG1 isotypic control (5 μg/mL; from BD Pharmingen), followed by PE-conjugated Streptavidin (1:500; from BD Pharmingen); Biotinylated anti-IL2Ra (5 μg/mL; from BD Pharmingen), followed by PE-conjugated Streptavidin (1:500; from BD Pharmingen); PE-conjugated anti-Tie2 (5 μg/mL; clone 83715) and anti-CCR2 (clone 48607), from R&D system; PE-conjugated anti-CD19 (clone HIB19), anti-CD4 (clone RPA-T4) and IgG1 isotypic control (5 μg/mL; clone 11711), from BD Pharmingen; PE-conjugated anti-CD133 (clone AC133) from Miltenyi; PE-conjugated anti-CD146 (clone S-endo1) from Biocytex; FICT-conjugated anti-M-CSFR, from R&D system; FICT-conjugated anti-CD62L, anti-CD31, anti-CD16, anti-CD14, from BD Pharmingen; FICT-conjugated anti-CD11c, from Caltag; FICT-conjugated anti-CD33, from ImmunoTools; FICT-conjugated anti-CD13, from eBioscience; APC-conjugated anti-TIE2 (clone 83715) and anti-VEGFR-2 (clone 89106), from R&D Systems; APC-conjugated anti-CD45, anti-CD14, anti-CD11b, anti-CD3, from BD Pharmingen; PE-Cy7-conjugated anti-CCR5, from BD Pharmingen; PC5-conjugated anti-CD56 and anti-CD16, from Beckman Coulter. All samples were analysed by a FC500 flow cytometer (Coulter). Frequency of marker-positive cells is expressed as mean±standard deviation (SD).

Mouse Samples:

For FACS analysis, we used a FacsCalibur (Becton-Dickinson). BM, PB and tumor-derived cell suspensions were incubated with 5% rat serum and 5 μg/ml rat anti-mouse FcγIII/II receptor (CD16/CD32) antibodies, and then stained using the following rat monoclonal antibodies: FITC-conjugated anti-Sca-1, anti-B220, anti-CD3, anti-CD11b, anti-Gr-1, anti-Ter119; PE-conjugated anti-CD11b, anti-Gr-1, anti-CD3, anti-CD19, anti-CD49b, anti-Sca-1, anti-CD13, anti-Tie2 (TEK4; see also Supplementary FIG. 2b for specificity of the antibody); PerCP-conjugated anti-CD45; APC-conjugated anti-CD31, anti-CD11b, anti-c-Kit. All antibodies and Fc-block, except for anti-Tie2 (E-Bioscience), were from BD PharMingen. All antibodies were used at a final concentration of 2-5 μg/ml.

Western Blot Analysis $10^6$ FACS-sorted human cells were lysed in Laemmli buffer, analysed by 8% SDS-PAGE, transferred on nitrocellulose, incubated for 2 hrs with rabbit anti-TIE2 (1:200; Santa Cruz Biotechnology) or mouse anti-β actin (1:5000; Sigma-Aldrich) antibodies, and revealed by goat anti-rabbit or anti-mouse HRP-conjugated antibodies (Upstate Biotechnology), followed by ECL plus (Amersham Biosciences) reaction and film exposures. For TIE2 immunoprecipitation, $10^7$ cells were lysed with RIPA lysis buffer and incubated overnight with anti-TIE2 antibodies (Santa-Cruz Biotechnology) and protein G microbeads (Miltenyi). Immunoprecipitated proteins were purified on separation columns (Miltenyi). Blots were incubated for 2 hrs with a mouse monoclonal HRP-conjugated anti-phospho-tyrosine antibody (1:1000; Upstate Biotechnology).

Real Time PCR

Total RNA was extracted from $1-5\times10^5$ cells using the RNeasy Micro kit (Qiagen) and retrotranscribed using the superscript III First-Strand kit (Invitrogen). Taqman analysis of TIE2, VEGFR-2 and GAPDH was performed on RNAse-treated cDNA using pre-made Taqman Gene Expression Assays from Applied Biosystems. Analyses were performed in 3 technical replicates, for 40 cycles in standard mode using an ABI7900HT apparatus. The SDS 2.2.1 software was used to analyse the data. The difference between the threshold cycle (Ct) of the TIE2 or VEGFR-2 transcript and that of the endogenous control GAPDH ($\Delta$Ct) was used to determine gene expression. The average Ct of GAPDH was ~16-18 in both hematopoietic cells and HUVEC. $\Delta$Ct values are expressed as mean±standard error. To obtain relative quantification values, we calculated the fold-change of each target mRNA over its content in a cell population taken as reference from the difference between the $\Delta$Ct of the target mRNA in the population of interest and the $\Delta$Ct of the target mRNA in the reference population ($\Delta\Delta$Ct) by the formula $2^{-\Delta\Delta Ct}$. For each relative value, an interval of confidence (=0.05) was calculated by the SDS 2.1.1 software; confidence intervals that did not overlap indicated statistically significant differences ($p<0.05$).

Immunohistochemistry, Immunofluorescence Staining and Confocal Analysis

Human Samples:

Tissue specimens were obtained from surgical resections following informed consent according to the Declaration of Helsinki and the H. San Raffaele Bioethical Committee. Samples were embedded in OCT compound and snap-frozen. Five-μm sections were fixed in 4% paraformaldehyde for 15 minutes and immunostained. Briefly, sections were incubated with anti-TIE2 antibodies followed by detection with a polymeric labelling two-step method (Super Sensitive™ ihc detection system, Biogenex) using 3,3'-diaminobenzidine as chromogen. After screening a panel of commercially available anti-TIE2 antibodies, two monoclonals, clone AB33 (Upstate Biotechnology; 1:200 dilution) and clone TEK9 (Reliatech; 1:100 dilution), were chosen based on their specific and efficient staining of blood vessels and utilized with similar results. After immunostaining, the sections were counterstained with hematoxylin and eosin. For immunofluorescence staining, frozen sections were blocked with 1% BSA and 5% fetal bovine serum (FBS). Sections were then stained with the following antibodies: goat polyclonal anti-TIE2 (from R&D systems) and monoclonal anti-TIE2 (clone AB33, from Upstate) antibodies followed by donkey anti-goat or goat anti-mouse AlexaFluor 546-conjugated antibodies (from Molecular Probes), respectively. To stain ECs and hematopoietic cells, the following antibodies were used: rabbit polyclonal anti-von Willebrand Factor (from DAKO) followed by AlexaFluor 488-conjugated anti-rabbit antibodies (from Molecular Probes); FICT-conjugated anti-CD31, anti-CD13, anti-CD16, anti-CD14 monoclonal antibodies; APC-conjugated anti-CD45, anti-CD34, anti-CD11b, anti-CD14 monoclonal antibodies (all from BD Pharmigen).

Mouse Samples:

Organs and tumors were prepared and cut into 6-20 μm cryostatic sections as previously described (De Palma et al., 2003). For immunofluorescence staining, we used the following antibodies: rat anti-CD31, anti-CD34; anti-CD45 (from BD Pharmingen); rat anti-CD11b (from Serotec); rat anti-IFN-α (Clone F18; HyCult Biotechnology). Rat anti-NG2 antibodies were a kind gift of Dr. P. Salven. GFP was immunolabeled using a rabbit anti-GFP antibody (Molecular Probes). Secondary antibodies were donkey anti-rabbit AlexaFluor488, goat anti-rat AlexaFluor488, donkey anti-goat AlexaFluor488, goat anti-rat AlexaFluor546, and donkey anti-goat AlexaFluor546 (from Molecular Probes). Cell nuclei were labeled by TO-PRO-3 (Molecular Probes).

Confocal microscopy used a three laser confocal microscope (Radiance 2100; BioRad). Fluorescent signals from the individual fluorophores were sequentially acquired from single optical sections and analyzed by Paint Shop Pro 7.02 (JascSoftware).

Migration Assays

Migration assays were performed in 24-well transwell containing 8 μm pore size inserts (Corning) coated with Basement Membrane Extract (Cultrex). Chemoattractants were placed in serum-free DMEM medium (600 μl) in the bottom compartment of the chamber, and 100 μl of cell suspension ($10^6$ cells/ml) was added to the top compartment. The chambers were incubated at 37° C. in humidified air with 5% $CO_2$ for 12 h. Migrated cells were labeled with 5 μg/ml calcein-AM (Molecular Probes) in DMEM at 37° C. for 1 h and counted under a fluorescence microscope. Results are expressed as mean±SD from three technical replicates. Number of cells migrated in the absence of chemoattractant (i.e. medium) was used as a reference value and set to 100%. 10% FBS was used as positive control. Neutralizing anti-TIE2 antibodies (R&D Systems) were preincubated with cells for 20 min at 37° C. Purified goat anti-human IgGs were from Caltag. Ang-2 (R&D Systems) was heat inactivated for 30 min at 95° C.

In Vivo Tumour Angiogenesis Assays

Human Cells:

FACS-sorted human cells were co-injected together with U87 human glioma cells in two ratios: 1:20 ($2.5\times10^5$ sorted cells together with $5\times10^6$ tumour cells) and 1:100 ($5\times10^4$ sorted cells together with $5\times10^6$ tumour cells), s.c. in nude mice, and tumours were grown for 5 (1:20 ratio experiment) or 7 (1:100 ratio experiment) days. To quantify angiogenesis, serial sections spanning the whole tumour were cut for each one of three tumours per group and immunostained for CD31 (rat anti-mouse CD31, from BD Pharmingen, followed by goat anti-rat AlexaFluor 546-conjugated antibodies, from Molecular Probes). The total tumour area in every fifth section was scanned at ×100 magnification by a confocal microscope. We then measured the vascular area on individual confocal planes by computer-assisted digital image analysis (Wild et al., 2000). Counts were averaged to obtain the vascular area and values are expressed as mean±SD. Statistical significance was calculated by student t-test.

Mouse Cells:

FACS_sorted mouse cells ($2.5\times10^4$) were injected together with N202.1A cells ($5-10\times10^5$) s.c. in nude mice and tumors grown for 5 days. To quantify angiogenesis, 3-5 sections of each of 2-7 tumors per group were immunostained for CD31 and scanned at ×200 magnification by a confocal microscope to identify regions of high vascular density. We then measured the vascular area by computer-assisted digital image analysis, as described (Wild et al., 2000), For matrigel plug assays, we used matrigel matrix with reduced growth factor composition (Becton-Dickinson). Matrigel plugs were obtained by mixing 250 μl of matrigel with 250 μl of IMDM medium containing $0.7-2.5\times10^5$ FACS-sorted murine cells, and by injecting the resultant cell suspension s.c. in male nude mice. To quantify angiogenesis, 3-5 sections of each of 2-7 tumors or matrigel plugs per group were immunostained for CD31 or CD34 and scanned at ×200 magnification by a confocal microscope to identify regions of high vascular density. We then measured the vascular area by computer-assisted digital image analysis, as described (Wild et al., 2000), or counted individual EC marker-positive vessels (or TO-PRO-3$^+$ nuclei belonging to vessels) in at least five ×200 fields from each section. Counts were averaged to determine the vascular area or the vessel density. In all studies, values are expressed as mean±sem. Differences were considered statistically significant at $p<0.05$ (unpaired Student's t-test).

Lentiviral Vectors

We cloned the murine interferon alpha (mIFN-α) cDNA (kindly obtained by S. Indraccolo, Padova) into the late-generation Tie2p/e-GFP and PGK-GFP lentiviral vectors (De Palma et al., Nat. Med. 2003 June; 9(6):789-95) in place of the GFP sequence. Concentrated lentiviral vector stocks, pseudotyped by the vesicular stomatitis viral envelope, were produced as described (Follenzi et al., Nat. Genet. 2000 June; 25(2):217-22) and their titers were determined using human umbilical vein ECs (HUVEC). Expression titers were $5\times10^9$ to $2\times10^{10}$ transducing units per ml with an HIV-1 p24 concentration of 100-500 μg/ml.

Bone Marrow Transplantation

Six to eight-week-old male nude mice were killed with $CO_2$ and their bone marrow was collected by flushing femurs and tibias. Lineage-negative cells were purified with a kit from StemCell Technologies. $5\times10^5$ lineage-negative cells/ml were transduced with increasing doses of vector ($1\times10^8$ HUVEC transducing units per ml) in serum-free StemSpan medium (StemCell Technologies) with cytokines. For BMT, transduced cells were injected into the tail vein ($1\times10^6$ cells/mouse) of 6-week-old female nude mice lethally irradiated to allow full engraftment of the transplanted hematopoietic stem cells (9.75 Gy). For clonogenic assays, we plated $1\times10^3$ bone marrow lineage-negative cells in a methylcellulose-based medium (MethoCult M3434; StemCell Technologies). For liquid culture, we plated $1\times10^5$ bone marrow lineage-negative cells in regular medium (IMDM, Sigma) supplemented with 10% FBS.

Intracranic Glioma Model

To induce orthotopic brain tumors in nude BMT mice, $2\times10^5$ human glioma U87 cells were delivered into the right striatum (0.2 μl/min) of deeply anesthetized (Avertin) adult female mice by stereotactic injection, as described (Galli et al., Cancer Res. 2004 Oct. 1; 64(19):7011-21). Tumor growth was monitored by MRI. MRI analyses were performed on a 3 Tesla human scanner (Intera 3T, Philips Medical Systems, the Netherlands), equipped with 40 mT/m gradients. A mouse-brain dedicated quadrature surface coil was employed (Rapid Biomedical, Germany). All mice were anaesthetized with Sevoflurane® (5% for induction and 2% for maintenance), in a 92% O2 mixture. During acquisition, mice were positioned prone on a dedicated temperature control apparatus to prevent hypothermia. After intra-venous administration of 0.2 mmol/kg of gadolinum (gadobutrol/Gadovist®, Shering, Germany), a 3D turbo T1 sequence was acquired on the axial plane (TR=501; TE=19; turbo-factor=7; voxel-size 80×80× 90 micron) and coronal and sagittal images were subsequently reformatted. The tumor volume and the absolute necrotic volume were calculated after manual segmentation of the lesion on the basis of signal intensity variation and enhancement characteristics. The total tumor volume and the absolute necrotic volume were obtained by summing the individual volumes (calculated as lesion area×slice thickness) in each slice. The relative necrotic fraction is the ratio (%) between the absolute necrotic volume and the total tumor volume.

Mice were euthanized by intracardiac perfusion with 4% paraformaldehyde. For immunofluorescence staining, the whole mouse brain was fixed in paraformaldehyde, stabilized by sucrose and snap-frozen in liquid nitrogen. To quantify angiogenesis, at least 5 sections from each organ or tumor were immunostained for CD31 and scanned at ×200 magnification by a confocal microscope (Radiance 2100; BioRad). We then used computer-assisted digital image analysis to measure the marker-positive area in at least 3-5×200 fields from each section. Counts were averaged to determine the relative vascular area, apoptotic-cell area, or number of immune cells/mm$^2$. In all studies, values are expressed as mean±standard deviation (SD) or standard error (SEM), as indicated. Differences were considered statistically significant at p<0.05 (unpaired Student's t-test). For immunofluorescence staining, we used the following antibodies: rabbit anti-Caspase-3 (Cell Signalling), anti-Ki67 (Novocastra), anti-NG2 (Chemicon), anti-GFP (Molecular Probes); rat anti-IFN-α (Clone F18; HyCult Biotechnology); PE-conjugated rat anti-CD31, APC-conjugated anti-CD11b (BD Pharmingen). Unconjugated primary antibodies were revealed by the following secondary antibodies: AlexaFluor488 donkey anti-rabbit and AlexaFluor546 goat anti-rat (Molecular Probes). Cell nuclei were labeled by TO-PRO-3 (Molecular Probes). To detect IFN-α, antigen retrieval by sodium citrate was performed on frozen sections prior to immunostaining. Confocal microscopy used a three laser confocal microscope (Radiance 2100; BioRad). Fluorescent signals from the individual fluorophores were sequentially acquired from single optical sections and analyzed by Paint Shop Pro 7.02 (JascSoftware).

Example 2

Tie2 Expression in Human Peripheral Blood Identifies a Subset of Noninflammatory Monocytes In order to investigate Tie2 expression by human haematopoietic cells, we stained peripheral blood (PB) obtained from healthy donors with a mouse anti-human Tie2 monoclonal antibody (clone 83715 from R&D systems; or clone 9 from RELIAtech. See methods above) and analysed cells by flow cytometry after lysis of erythrocytes.

Figure 1B:
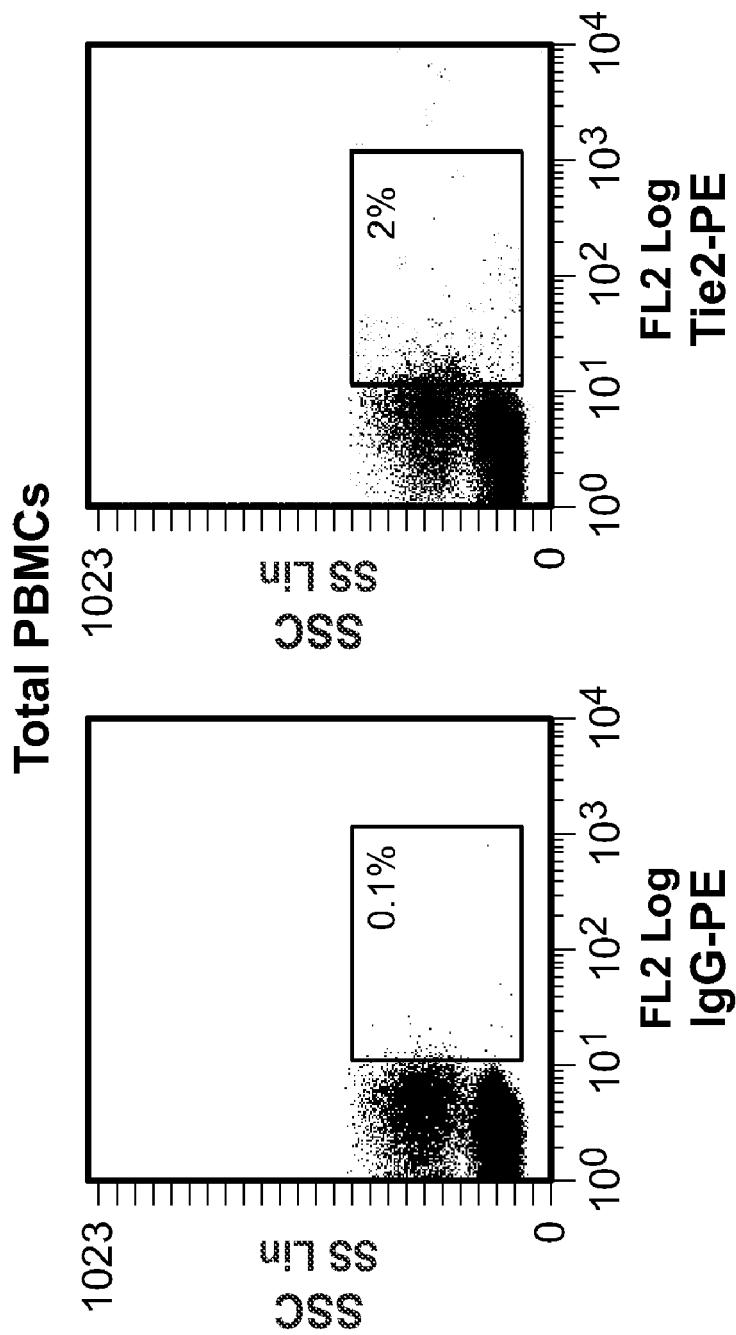

The main haematopoietic populations in PB are granulocytes (50-70%), lymphocytes (25-40%) and monocytes (5-10%). We found that only a small fraction (0.1-0.5%; n=7) of these leukocytes expressed Tie2 to detectable levels (FIG. 1A), implying that the wide majority of granulocytes were Tie2$^-$, a finding in contrast with a previous report that showed that human neutrophils expressed Tie2 (Lemieux et al., 2005). However, we noted that Tie2$^+$ cells co-purified with peripheral blood mononuclear cells (PBMCs; FIG. 1B)—the haematopoietic cell fraction containing lymphocytes and monocytes. Tie2$^+$ cells accounted for 1.6-7.4% (mean: 3.3±1.5%; n=16) of the total PBMCs (n>20 samples from different donors)

Figure 1C:
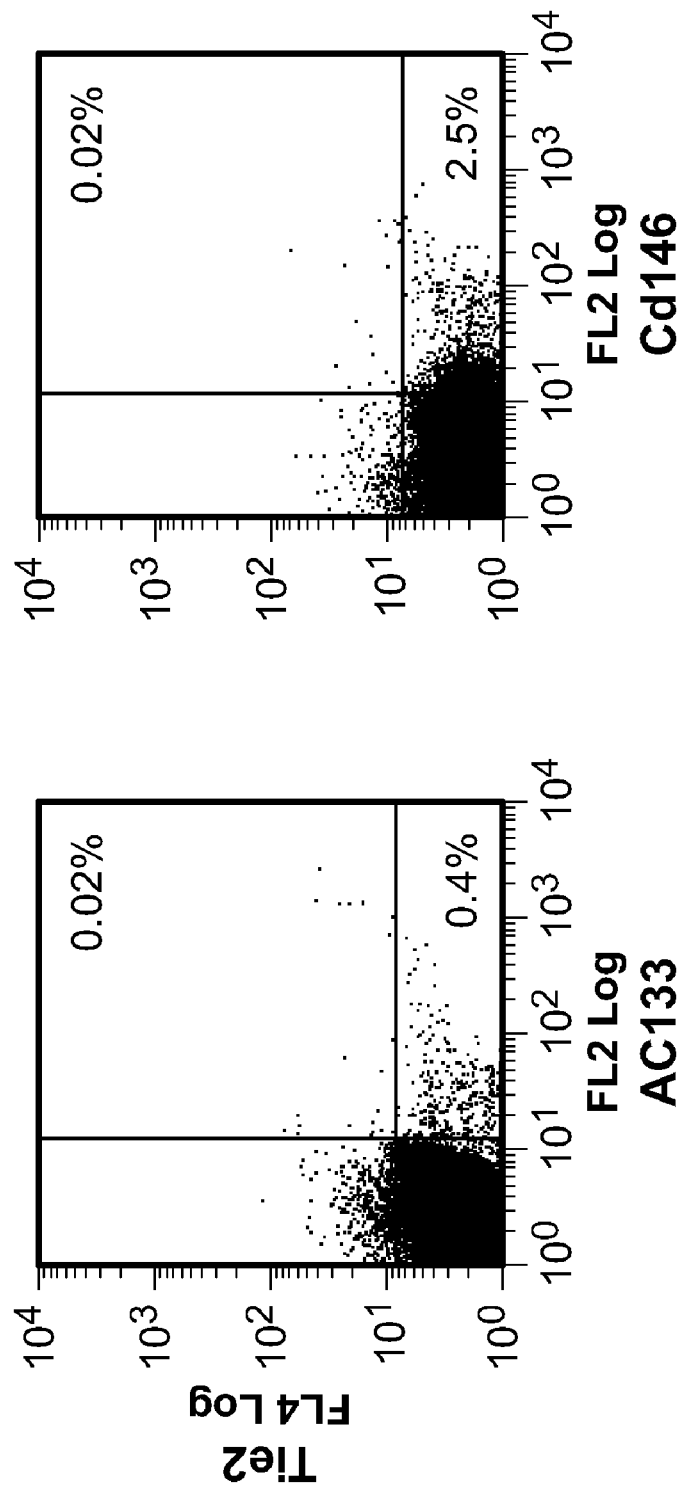
Figure 1D:
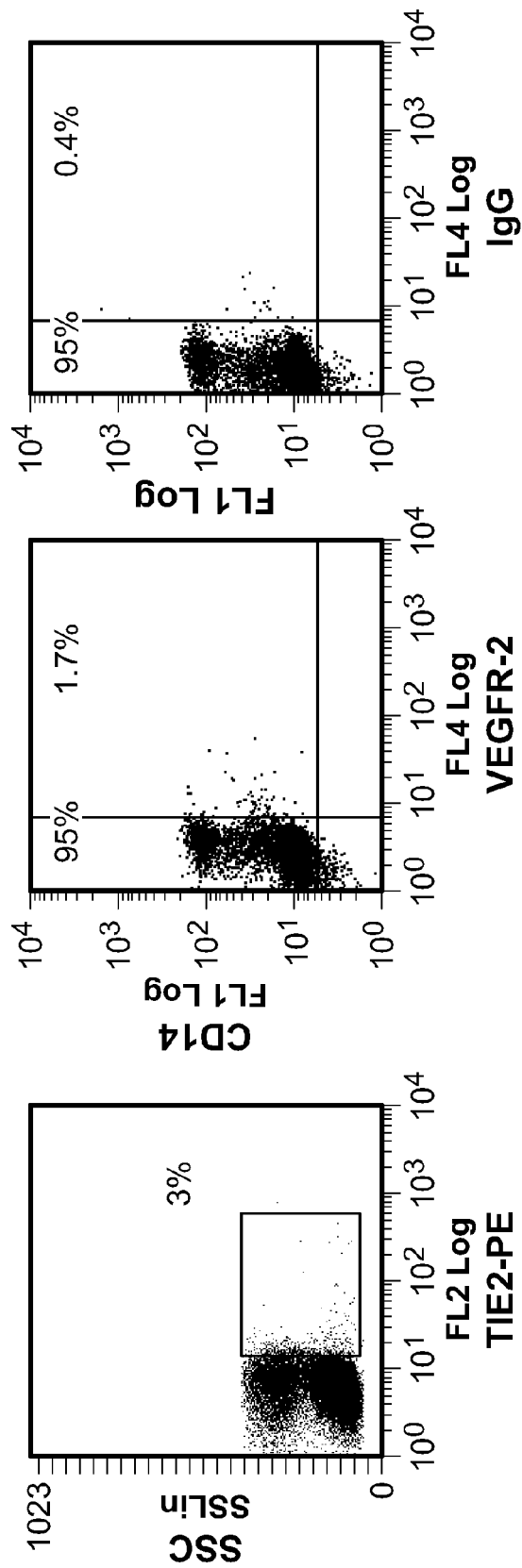

Circulating endothelial cells (CECs) and endothelial progenitor cells (EPCs) can be detected at very low frequency in PB and are expected to express TIE2 (Rafii et al., 2002). The relatively high frequency of the TIE2$^+$ cells described above and the fact that these cells express monocyte markers (see below) would, in principle, be sufficient to exclude that they represent CECs/EPCs. However, to formally rule out this possibility, we stained PBMCs with monoclonal antibodies directed against VEGFR-2, AC133 and CD146, which have been previously used to identify CECs/EPCs. We found that the vast majority of the PB TIE2$^+$ cells were AC133$^-$, CD146$^-$ (FIG. 1C) and VEGFR-2$^-$ (FIG. 1D), further indicating that they were distinct from circulating CECs/EPCs. We noted, however, that a small fraction (1-2%) of the TIE2$^+$ cells were CD14$^+$VEGFR-2$^+$, a phenotype previously associated with monocytes endowed with endothelial-like differentiation capacity (Elsheikh et al., 2005).

Figure 1E:
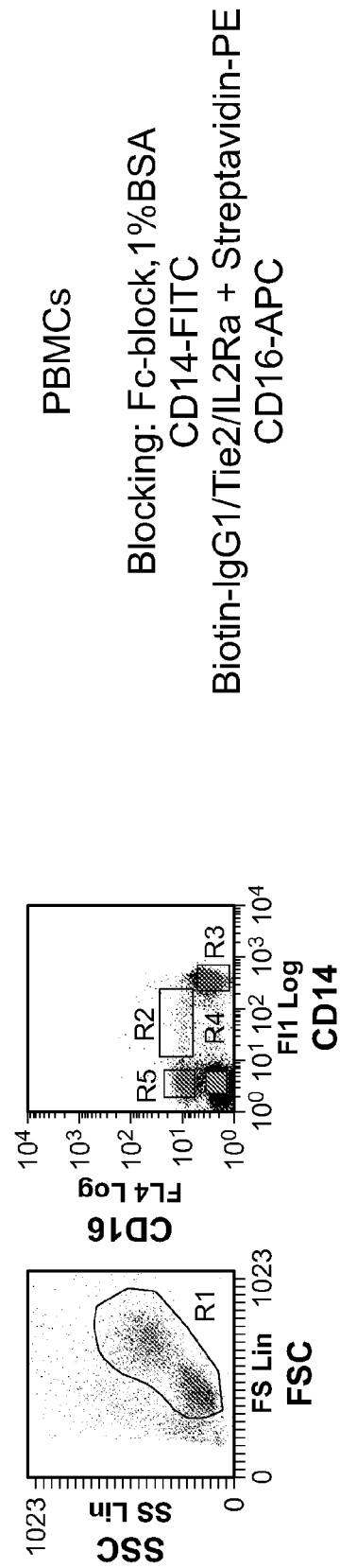
Figure 1F:
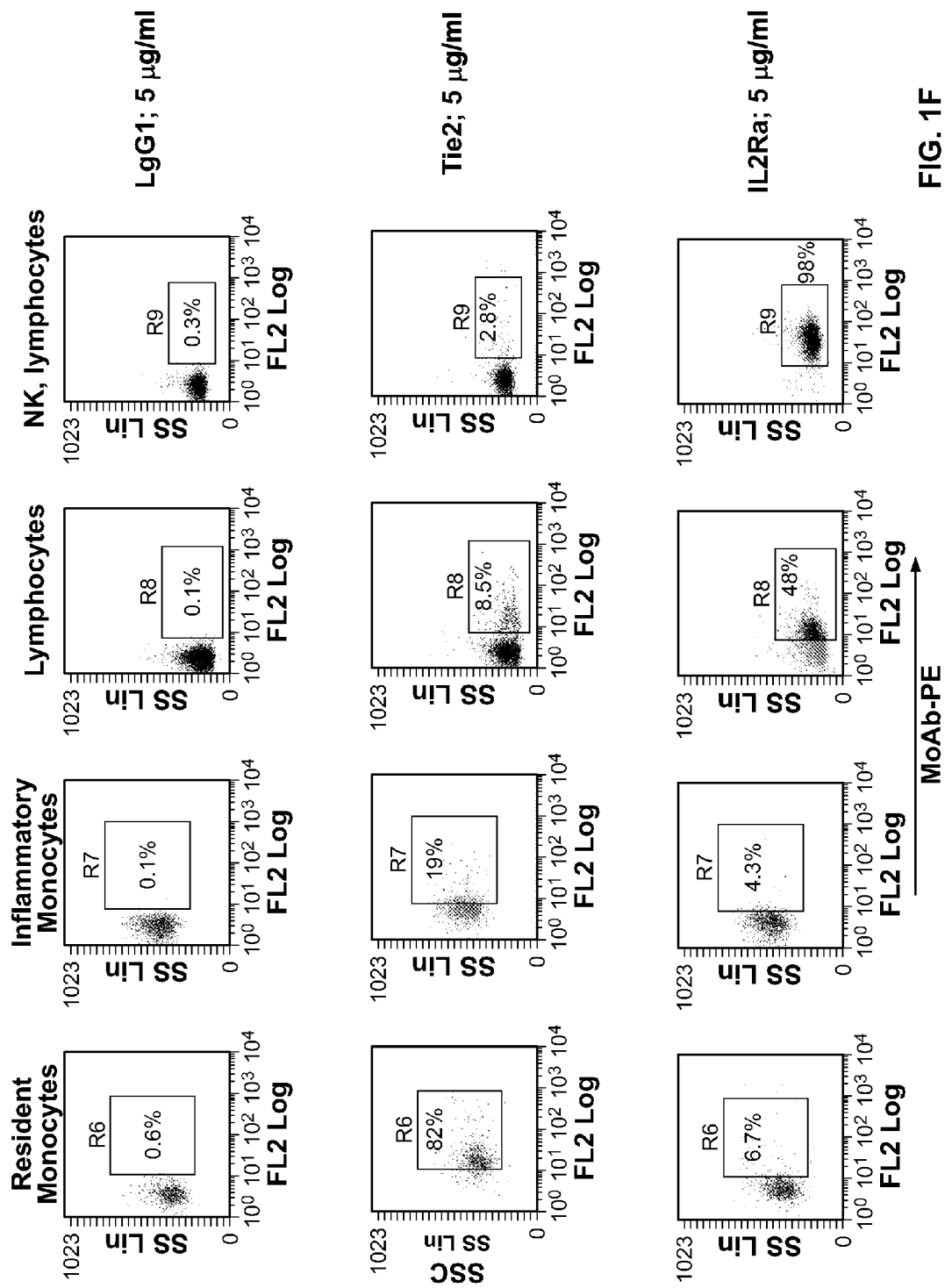

Studies have suggested that human monocytes can be divided into two main subsets (Gordon and Taylor, 2005) according to the expression of CD14, a component of the lipopolysaccharide receptor, and CD16, a human Fc gamma receptor III. CD14$^+$CD16$^-$ cells are the most abundant monocytes in PB (termed 'classical' or 'inflammatory' monocytes) and are thought to represent monocytes mediating innate inflammatory responses, whereas CD14$^+$CD16$^+$ cells are a minor and less characterised monocyte subset, possibly representing the precursors of tissue-resident macrophages, sometimes referred to as 'resident' monocytes. Interestingly, we found that CD14$^{low}$CD16$^+$ monocytes were highly enriched in Tie2$^+$ cells, whereas much fewer Tie2$^+$ cells were found among inflammatory CD14$^+$CD16$^-$ monocytes (FIG. 1E). In several samples (at least 12 samples from different donors), analysed either by multi-color flow cytometry (FIG. 1E) or after FACS-sorting of the two monocyte subsets (FIG. 1F), TIE2$^+$ cells accounted for 35-85% of the CD14$^{low}$CD16$^+$ monocytes. These results indicated that TIE2 expression in PB specifically identified a subset of CD16$^+$ monocytes distinct from common inflammatory monocytes.

Figure 2A:
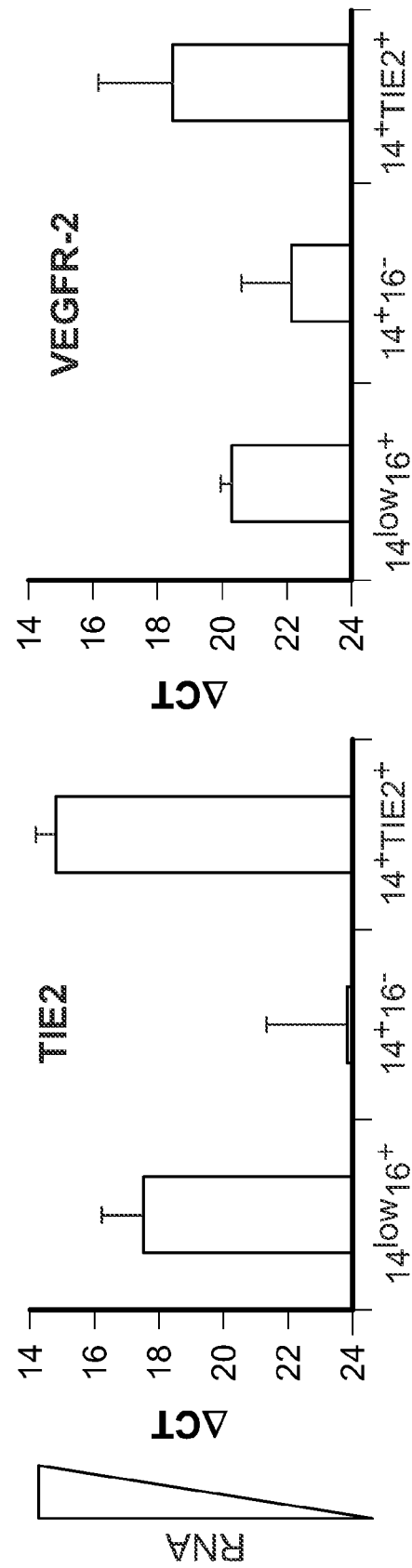
FIG. 2: TIE2 receptor expression by TIE2$^+$ monocytes. (A) TaqMan analyses of TIE2 and VEGFR-2 transcripts in FACS-sorted monocyte subsets showing ΔCt values over endogenous control GAPDH. The lower the ΔCt, the higher the expression of the transcript in the target cell population. ΔCt values are expressed as mean±standard error. Note that TIE2 transcript is clearly expressed in CD14$^{low}$CD16$^+$ (14$^{low}$16$^+$) resident but nearly undetectable in CD14$^+$CD16$^-$ (14$^+$16$^-$) inflammatory monocytes. (B) Relative quantification values of TIE2 transcript in FACS-sorted monocyte subsets. TIE2 transcript is significantly enriched in CD14$^+$TIE2$^+$ (14$^+$TIE2$^+$) TEMs as compared to the resident monocytes. For each relative value, an interval of confidence was calculated; confidence intervals that do not overlap indicate statistically significant differences (p<0.05). (C) Western blot analysis of TIE2 protein expression in the indicated cell populations. Blots were probed with C-terminus specific anti-TIE 2 rabbit (top panels) or mouse anti-beta actin (bottom panels) antibodies. The expected migration of each protein relative to molecular weight standards is indicated. Representative experiment of three performed. (D) TIE2 immunoprecipitated from CD14$^{low}$CD16$^+$ resident monocytes is phosphorylated on tyrosine. Representative experiment of two performed.
Figure 2B:
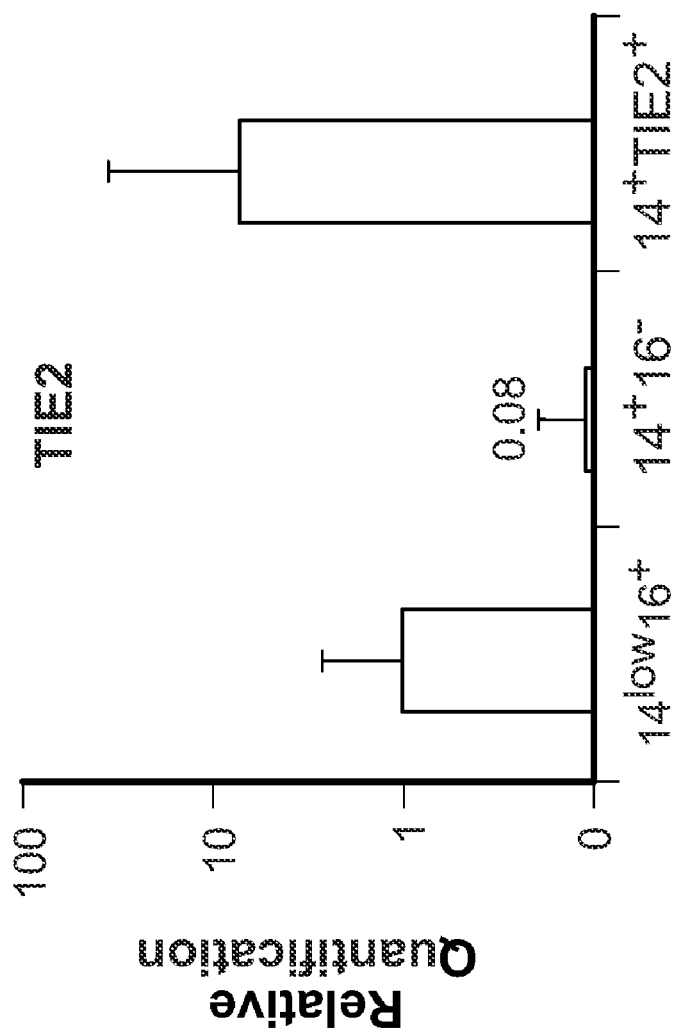
Figure 3A:
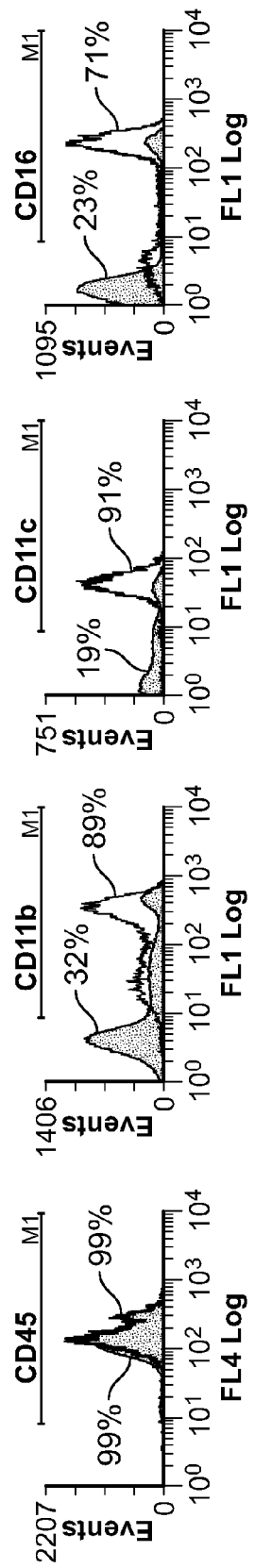
FIG. 3(A)-(D): Characterization of Tie2$^+$ mononuclear cells in unfractioned PBMCs stained with the indicated antibodies. Histograms show the frequency of marker-positive cells contained within the Tie2$^+$ population The open histogram indicates the Tie2$^+$ cells (with percentage of marker-positive cells), while the filled histogram indicates the total population (with percentage of marker-positive cells). The TIE2$^+$ cells were CD45$^+$, CD11b$^+$, CD11c$^+$, CD16$^+$, CD33$^+$, CD115$^+$ and CD13$^+$, which are all markers of monocytic cells. In addition, the TIE2$^+$ cells were CCR2$^-$, CD62L (L-selectin)$^-$ and CCR5$^+$, a surface profile previously associated with resident monocytes. As expected, the TIE2$^+$ cells were CD56$^-$, CD3$^-$ and CD19$^-$ and thus distinct from natural killer cells, T and B lymphocytes. Representative analysis of 3-6 experiments performed on different donors.
Figure 3B:
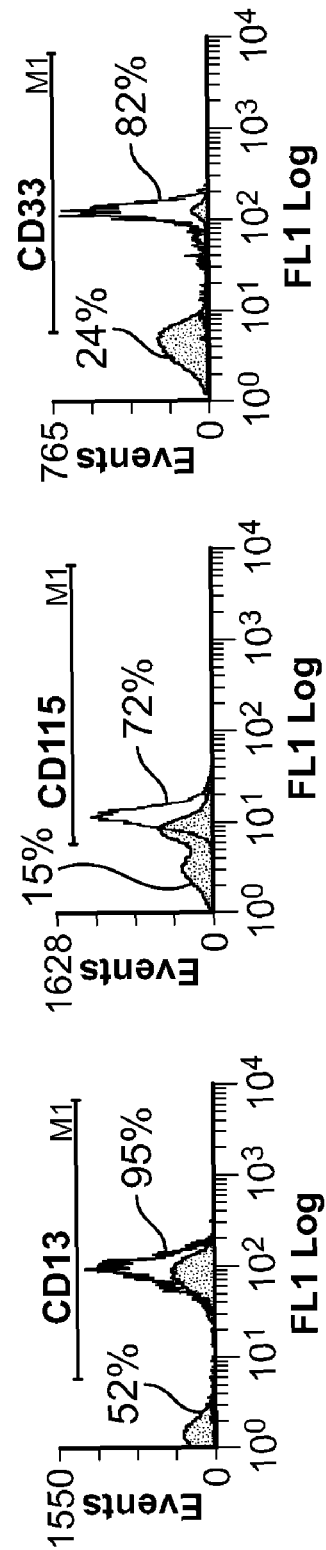
Figure 3C:
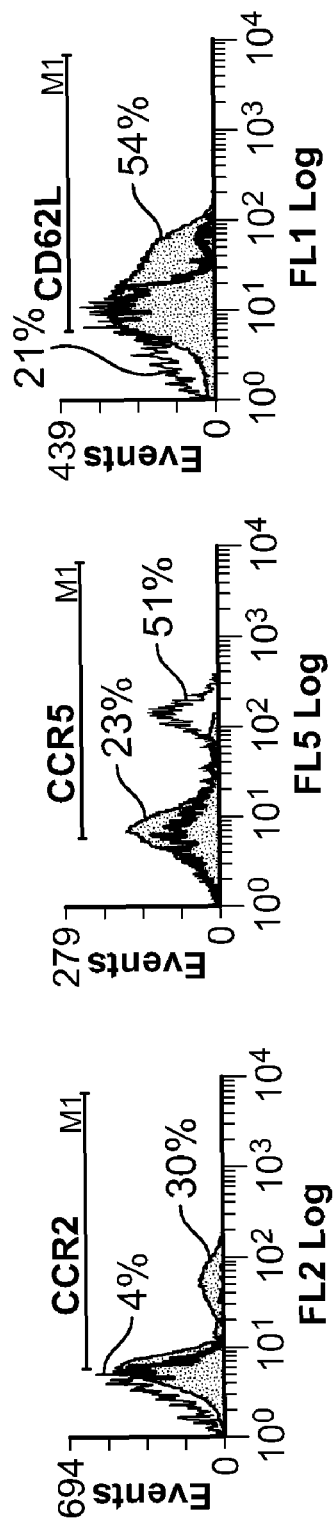
Figure 3D:
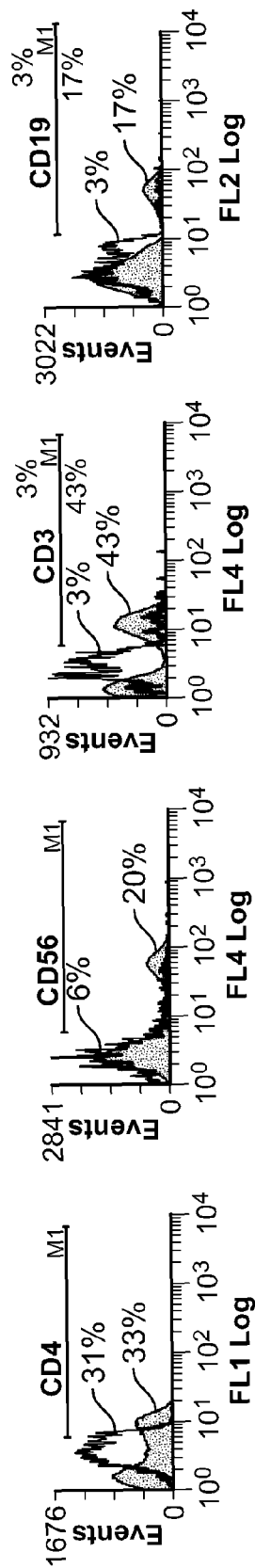

In order to verify TIE2 expression at the transcriptional level, we performed Real Time PCR of TIE2 mRNA on FACS-sorted CD14$^+$TIE2$^+$ TEMs, CD14$^{low}$CD16$^+$ resident and CD14$^+$CD16$^-$ inflammatory monocytes, using GAPDH as internal standard (FIGS. 2A and 2B). The TIE2 transcript was clearly expressed in CD14$^{low}$CD16$^+$ resident but nearly undetectable in CD14$^+$CD16$^-$ inflammatory monocytes, and it was significantly enriched (8-fold) in CD14$^+$ TIE2$^+$ TEMs as compared to the resident monocytes. However, TIE2 mRNA expression in TEMs was much lower than in human endothelial cells (HUVEC), used as positive control (ΔCt=6.1±0.6; n=2). Of note, the VEGFR-2 transcript, which was expressed in HUVEC to a similar level as TIE2 (ΔCt=5.8), was expressed to a much lower level than TIE2 in resident monocytes and TEMs. These results argue against the possibility that low-level contamination of the TIE2$^+$ cell fraction by CECs/EPCs was responsible for the recovery of TIE2 signal from monocytes.

We then analysed TIE2 receptor expression by Western blot analysis of sorted hematopoietic populations using antibodies directed against the C-terminus of the TIE2 protein. As shown in FIG. 2C, a band with the expected 145 kD molecular weight of the TIE2 protein and co-migrating with a major band in HUVEC was clearly detectable only in lysates of FACS-sorted CD14$^+$ TIE2$^+$ cells and barely detectable in total PBMCs, among all blood cell subsets analysed. TIE2 was auto-phosphorylated on tyrosine, as shown by immunoprecipitation from magnetically sorted resident monocytes and immunostaining with anti-phosphotyrosine antibodies, indicating functional activation of the receptor in these cells (FIG. 2D).

We further investigated the phenotype of circulating Tie2$^+$ cells (FIG. 3) and found that they were CD11b (MAC-1)$^+$, CCR2$^-$, CCR5$^+$ and L-selectin (CD62L)$^-$, a surface profile that has been previously associated with resident monocytes. As expected, Tie2$^+$ cells did not express the lymphocyte-specific markers CD3 (T cells) and CD19 (B cells), whereas they expressed CD4, a T lymphocyte co-receptor also expressed by monocytes. Tie2$^+$ cells expressed CD33 (sialic-acid binding Ig-like lectin 3), a sialoadhesion integrin highly expressed by monocytes, and the macrophage-colony stimulating factor receptor (M-CSFR, also known as c-fms or CD115), a chemokine receptor involved in the recruitment of monocytes to tumours. Interestingly, expression of both CD33 and CD115 has also been associated with an immature monocyte phenotype (Taussig et al., 2005). In summary, the phenotype of Tie2$^+$ cells strongly suggests that they represent a specific population of monocytes distinct from classical inflammatory monocytes and contained within the resident monocyte subset. The noninflammatory phenotype of human Tie2$^+$ monocytes is consistent with that of mouse TEMs, which express CD11b but not Gr-1, a combination of markers that has been proposed to be associated with mouse resident monocytes. Table 1 compares marker expression in human and mouse peripheral blood human Tie2 expressing monocytes.

TABLE 1

| MARKERS | Peripheral Blood Human Tie2 expressing monocytes (Hu-TEMs) | Peripheral Blood Mouse Tie2 expressing monocytes (TEMs) |
| --- | --- | --- |
| Tie2 | + | + |
| CD14 | + | − |
| CD11b | + | + |
| CD16 | + | NA |
| Gr-1 | NA | − |
| CD45 | + | + |
| CD31 | −/low | −/low |
| CCR5 | + | ND |
| CD33 | + | ND |
| L-selectin (CD62L) | − | ND |
| CCR2 | − | ND |
| M-CSFR (CD115) | + | ND |
| CD19 (B cell marker) | − | − |
| CD3 (T cell marker) | − | − |
| Sca-1 | NA | −/+ |
| c-Kit | ND | − |

NA = Not Applicable
ND = Not Determined

Example 3

Tie2-Expressing Monocytes are Recruited to Human Tumours

We showed that TEMs infiltrate murine tumours, including spontaneously and orthotopically growing neoplasms (De Palma et al., 2005). To study whether human Tie2$^+$ monocytes are present in human solid tumours, we analysed the haematopoietic infiltrate of 28 human carcinoma specimens, including kidney, colorectal, breast, gastric, pancreatic and lung cancers, by four-color FACS analysis, immunohistochemistry and immunofluoresce triple staining (Table 2).

TABLE 2

Cancer specimens and normal organs analyzed in this study

| | Tie2 expression in mononuclear cells | Method of analysis |
| --- | --- | --- |
| Cancer specimens | | |
| Colon adenocarcinoma (5) | 5/5 | C, F, |
| Gastric adenocarcinoma (2) | 2/2 | C, I |
| Pancreatic adenocarcinoma (1) | 1/1 | C, I |
| Liver metastasis (1) | 0/1 | I |
| Breast carcinoma (1) | 1/1 | C, F, |
| Renal clear cell carcinoma (2) | 2/2 | F, |
| Non small cell lung cancer (2) | 2/2 | C, F, |
| Brain glioblastoma (1) | 0/1 | I |
| Papillary cell carcinoma of thyroid (1) | 1/1 | F, |
| Soft tissue tumours (5) | 4/5 | C, I |
| Normal organs | | |
| Colon (5) | 0/5 | C, F, |
| Stomach (2) | 0/2 | C, I |
| Pancreas (1) | 0/1 | C, I |
| Liver (1) | 0/1 | I |
| Skin (2) | 0/2 | I |
| Kidney (2) | 0/2 | F, |
| Lung (2) | 0/2 | F, |
| Thyroid gland (1) | 0/1 | F, |
| Tonsil (1) | 0/1 | C, I |

Figure 4A:
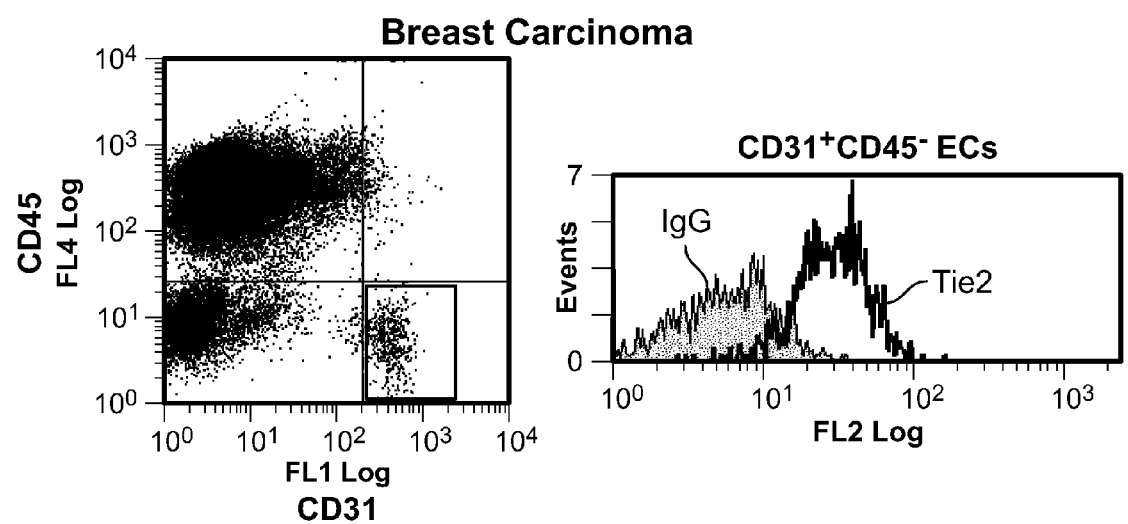
FIG. 4: FACS analysis of the indicated tumour specimens, analysed as described in the Examples. Briefly, fresh cancer specimens were processed mechanically and by collagenase digestion for 2 h at 37° C., then filtered and prepared for FACS analysis. The analysis used PE-conjugated anti-Tie2, APC-conjugated anti-CD45, FITC-conjugated anti-CD31 and PC7-conjugated anti-CD14 antibodies. The anti-Tie2 antibody was from R&D system. TIE2$^+$ monocytes are found in human tumours. Flow cytometry analysis of the indicated tumour specimens, processed and analysed as described in the text. FITC-conjugated anti-CD31 or anti-CD14, PE-conjugated anti-TIE2, APC-conjugated anti-CD45 antibodies were used, (A) Breast carcinoma. Note that the gated CD31$^+$CD45$^-$ tumour-derived ECs are TIE2$^+$ (open line in the histogram on the right; filled line is the IgG isotype control). (B) Renal carcinoma. In this tumour specimen, ~2% of the tumour-derived cells are CD31$^+$ (CD45$^-$, not depicted) ECs. The wide majority of these CD31$^+$ tumour-derived ECs are TIE2$^+$. Note that a fraction of the tumour-derived cells are CD31$^-$TIE2$^+$ non-ECs (upper right dot plot). In the same tumour sample, ~10% of tumour-derived cells are CD45$^+$ hematopoietic cells. Only a minor fraction (12%) of these CD45$^+$ cells are TIE2$^+$ (lower right dot plot). (C) and (D) Colon carcinoma (left) and non-neoplastic colon mucosa (right). In the tumour, 4% of the abundant CD45$^+$ hematopoietic cells and most of the CD14$^+$ monocytes are TIE2$^+$. In the normal mucosa, CD45$^+$ hematopoietic cells are much less abundant than in the tumour, and only a few TIE2$^+$ cells are found. Note that CD14$^+$ monocytes are not detected in the normal mucosa. (E) and (F) Lung adenocarcinoma (left) and non-neoplastic lung tissue (right). In the tumour, more than 30% of the cells are CD45$^+$ hematopoietic cells, of which 6% are TIE2$^+$. Most of the tumour-derived CD14$^+$ monocytes are TIE2$^+$. In the normal lung tissue, the CD45$^+$ hematopoietic cells are TIE2$^-$; note that CD14$^+$ monocytes are not found in this tissue.
Figure 4B:
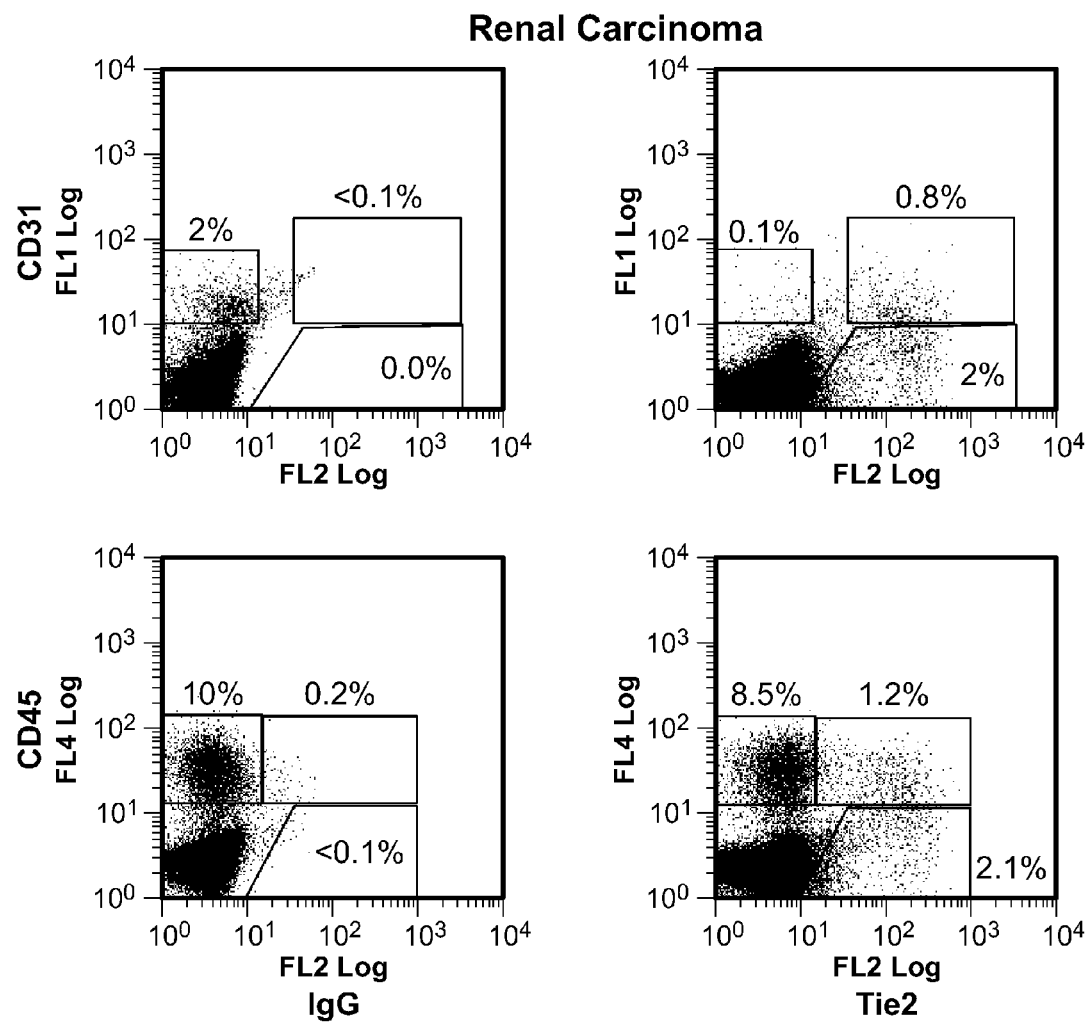
Figure 4C:
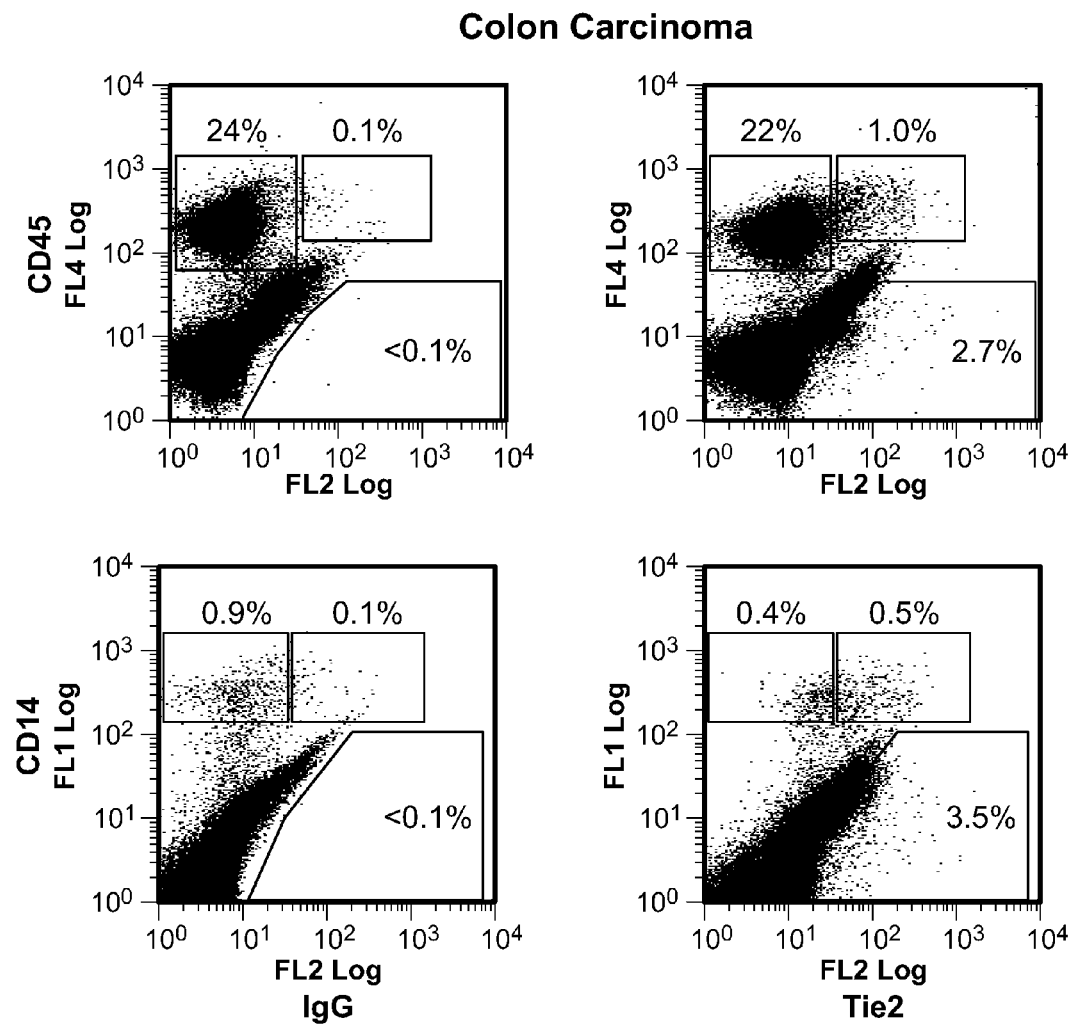
Figure 4D:
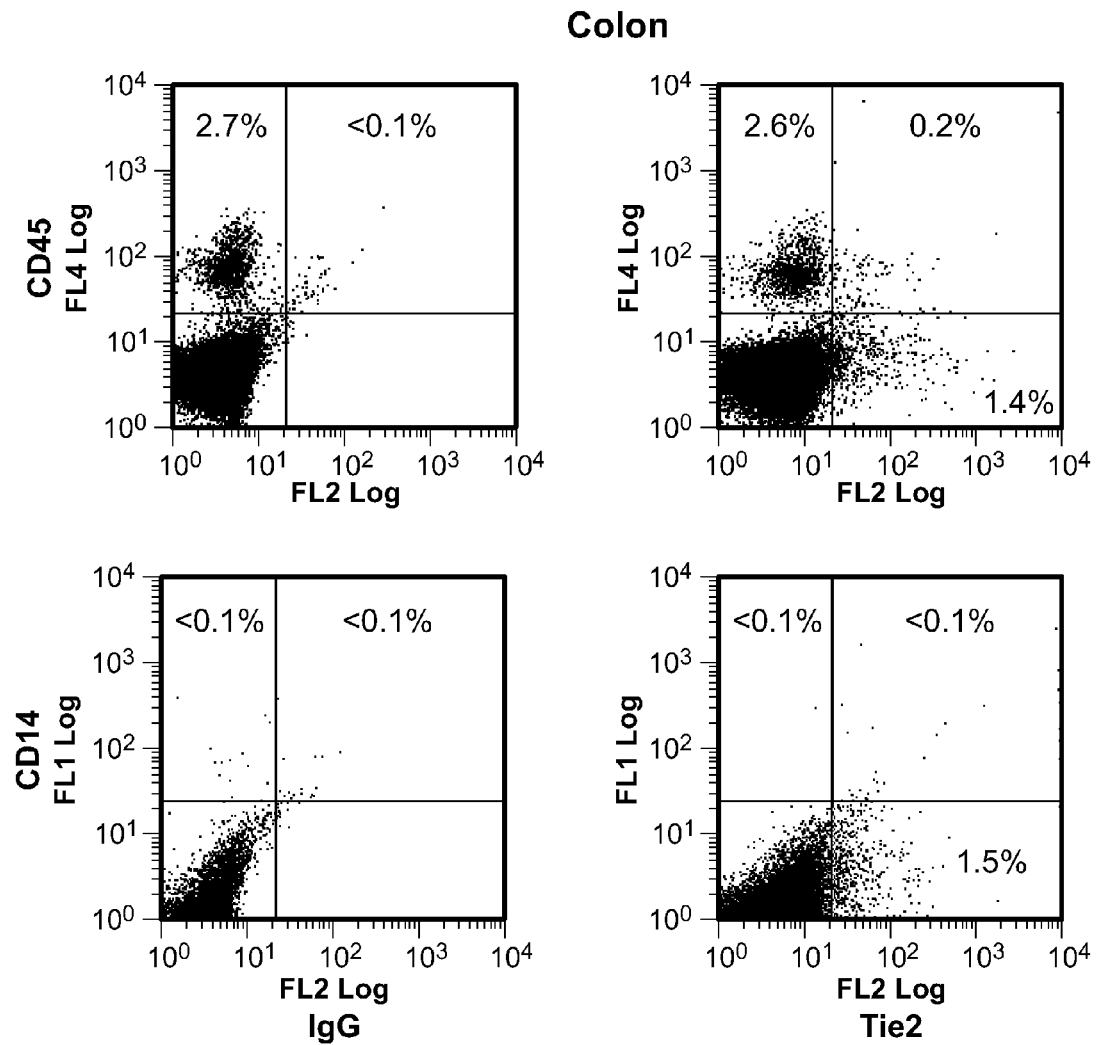
Figure 4E:
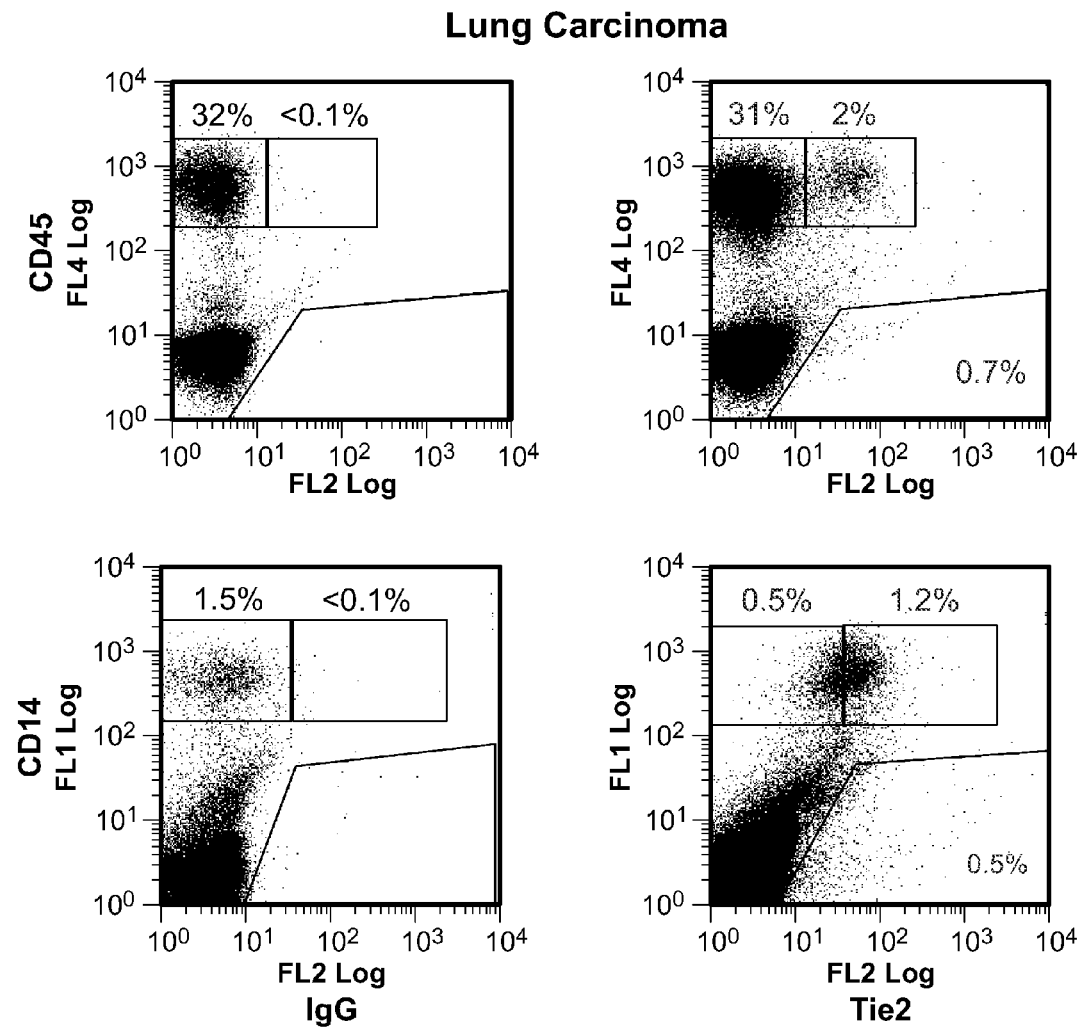
Figure 4F:
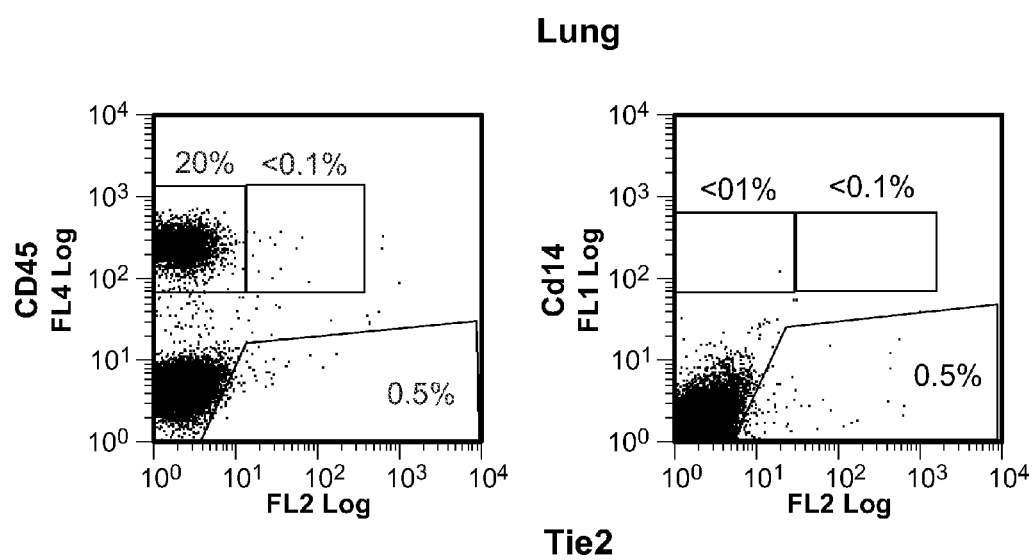

C = confocal immunofluorescence analysis; I = immunohistochemistry; F = flow cytometry Fresh tumour tissues obtained from surgical resections were made into single cell suspensions and analysed by flow cytometry for the expression of i) the pan-leukocyte marker CD45, ii) the monocyte markers CD14 or CD11b, iii) the EC markers CD31 or CD34, and iv) TIE2 (FIG. 4). Where possible, a sample of non-neoplastic tissue adjacent to the tumour was also obtained for comparative analysis. As expected, in all tumours analysed (n=9) the vast majority of ECs, defined as CD31$^+$CD45$^-$ or CD34$^+$CD45$^-$ expressed TIE2 (FIGS. 4A and B). In addition to ECs, we noted that a small fraction (1-12%) of the total CD45$^+$CD31$^{-/low}$ tumour-derived leukocytes expressed TIE2 (FIG. 4B). Interestingly, these TIE2$^+$CD45$^+$ cells were highly enriched in the CD14$^+$ population (37-72% TIE2$^+$, n=7), which is a small fraction of the hematopoietic infiltrate and likely represents monocytes or immature macrophages. As compared to the blood TEMs, the average expression level of TIE2 appeared substantially higher in the TIE2$^+$ tumour-infiltrating monocytes. Two representative examples of these analyses are illustrated in FIGS. 4C and D, which shows that 4% and 6% of the CD45$^+$ leukocytes and 55% and 70% of the CD14$^+$ monocytes were TIE2$^+$ in a colorectal (FIG. 4C) and a lung (FIG. 4D) carcinoma, respectively. Of note, in both tumours the wide majority of tumour-infiltrating CD45$^+$ leukocytes, which may comprise TAMs, lymphocytes and granulocytes, were TIE2$^-$. Intriguingly, the frequency of TIE2$^+$CD45$^+$ cells was significantly lower or undetectable in non-neoplastic tissues adjacent to the tumours. As expected, normal tissues had a lower overall content of CD45$^+$ hematopoietic cells than the tumours.

Figure 5A:
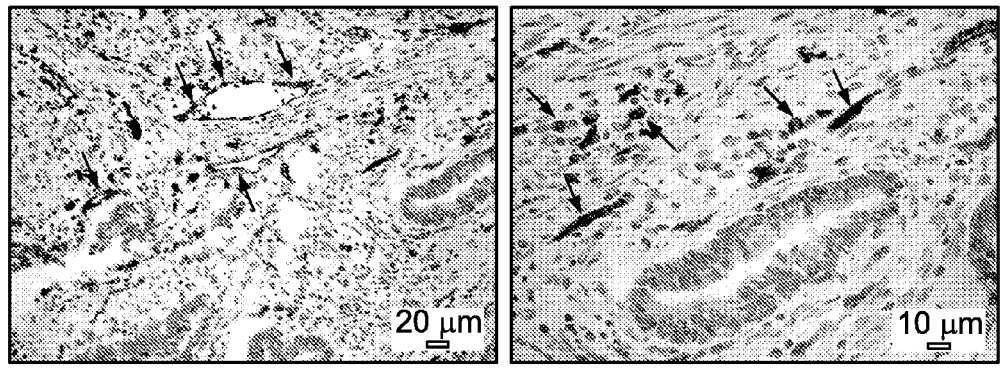
FIG. 5: TIE2 immunohistochemistry of human cancer cryosections. After TIE2 immunostaining, the sections were counterstained with haematoxylin and eosin, and shown at lower (left) or higher (right) magnification. (A) Colon adenocarcinoma. In addition to vascular ECs (arrowheads), TIE2 staining highlights the presence of stromal mononuclear elements morphologically consistent with monocytes (arrows). These cells appear inhomogeneously distributed, with foci of high density (arrows). (B) Gastric undifferentiated adenocarcinoma. Many TIE2$^+$ mononuclear cells are found in the tumour stroma (arrows). Blood vessels indicated by arrowheads. (C) Pancreatic adenocarcinoma. The majority of TIE2$^+$ structures in the left panel are blood vessels (arrowheads). An individual TIE2$^+$ mononuclear cell is shown (arrow) in the right panel.
Figure 5B:
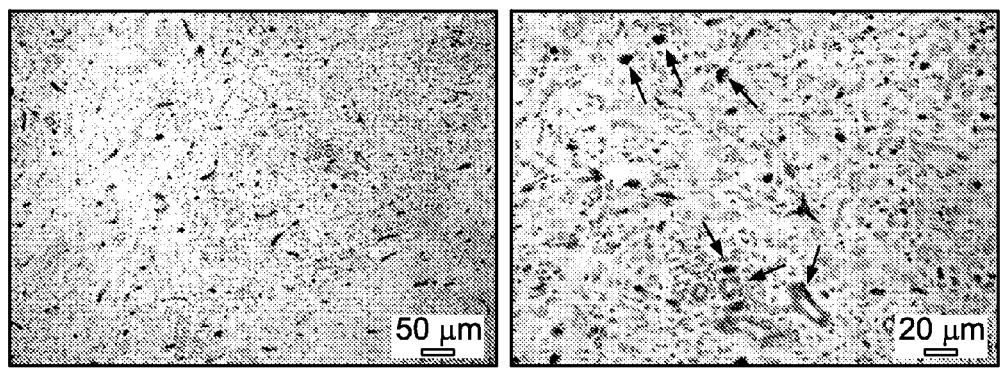
Figure 5C:
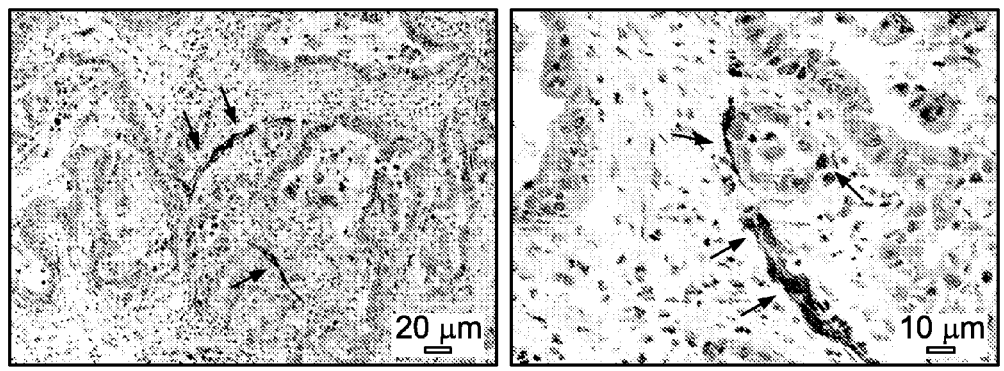

TIE2 immunostaining of cryostatic sections of cancer specimens (Table 1) showed, in addition to robust and near-uniform marking of blood vessels, the presence of scattered TIE2$^+$ mononuclear cells within the tumour stroma (FIG. 5). These cells appeared distinct from ECs because they did not show connection to blood vessels, had monocytic features (i.e. roundish cytoplasmic outline and small nuclei) and showed uniform staining by anti-TIE2 antibodies lining the cell surface. Note that this type of single-marker analysis could not identify TIE2$^+$ monocytes closely associated with TIE2$^+$ blood vessels. Consistently with the flow cytometry data, the frequency of the TIE2$^+$ mononuclear cells was low albeit variable among different tumour specimens, with some tumours displaying minimal infiltration and others showing focal increase of TIE2$^+$ cells. The vast majority of tumour-infiltrating hematopoietic cells, including TAMs, were TIE2$^-$, ruling out Fc-dependent binding of the antibody to macrophages.

Figure 6:
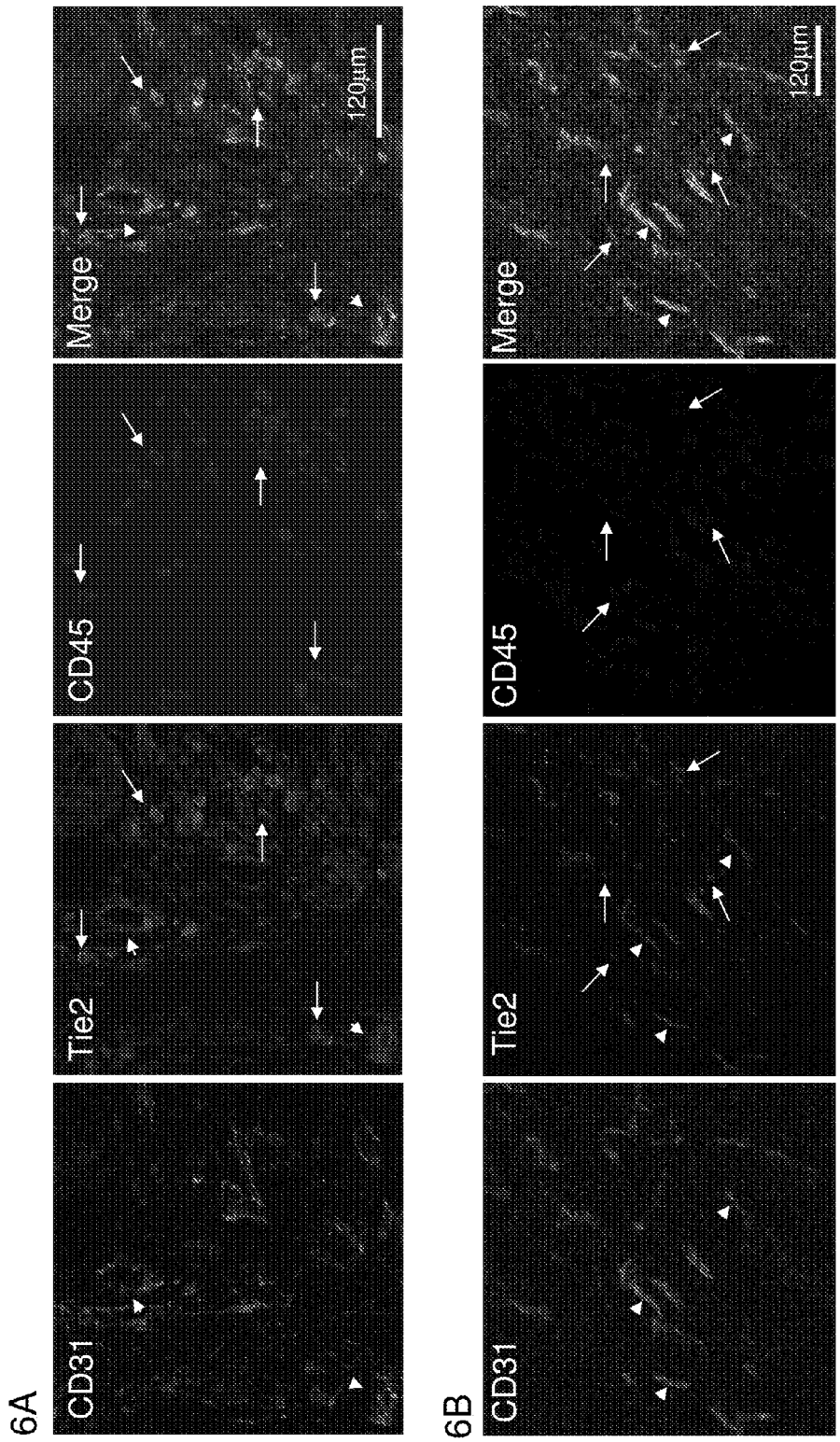
FIG. 6: Confocal immunofluorescence analysis of human cancer sections confirms the presence of TIE2$^+$CD45$^+$CD14$^+$ tumour-infiltrating monocytes. (A) Colon adenocarcinoma analysed for CD31 (green), TIE2 (red) and CD45 (blue). Confocal planes are shown individually and after merging. Several TIE2$^+$CD45$^+$CD31$^-$ hematopoietic cells (merge of red and blue giving purple; arrows) are found within the tumour stroma. Note that TIE2 is expressed by vascular ECs (merge of green and red giving yellow; arrowheads), which are TIE2$^+$CD45$^-$CD31$^+$. (B) Gastric adenocarcinoma analysed for CD31 (green), TIE2 (red) and CD45 (blue). Some TIE2$^+$CD45$^+$CD31$^-$ hematopoietic cells are found in the tumour stroma (arrows) together with TIE2$^+$CD45$^-$CD31$^+$ tumour blood vessels (arrowhead). Scale bars as indicated. (C) Colon adenocarcinoma analysed for CD14 (green), TIE2 (red) and CD11b (blue). Several TIE2$^+$CD14$^+$CD11b$^+$ monocytes (arrows) are found within the tumour stroma. Note TIE2 expression by TIE2$^+$CD14$^-$CD11b$^-$ vascular ECs (arrows). (D) Gastric adenocarcinoma analysed for vWF (green), TIE2 (red) and CD11b (blue). Arrows indicate TIE2$^+$CD11b+ vWF$^-$ monocytes. (E) Pancreatic adenocarcinoma analysed for CD16 (green), TIE2 (red) and CD14 (blue). High-magnification photos show the presence of TIE2$^+$CD16$^+$CD14$^+$ monocytes (arrows) in the tumour stroma. (F) Colon adenocarcinoma analysed for CD14 (green), TIE2 (red) and CD11b (blue). A triple-positive CD14$^+$TIE2$^+$CD11b$^+$ TEM with periendothelial localisation is indicated by the arrow. Note the presence of CD14$^-$ TIE2$^-$CD11b$^+$ inflammatory cells (arrowheads). Scale bars as indicated. (G) TIE2 expression in non-neoplastic tissues is restricted to vascular ECs. Nonneoplastic colon mucosa adjacent to tumour tissue analysed by confocal immunofluorescence staining of CD31 or CD14 (green), TIE2 (red) and CD45 (blue). Note that the lamina propria macrophages are CD14$^-$TIE2$^-$. A single CD14$^+$ TIE2$^-$ monocyte (arrow) is found within a TIE2$^+$ blood vessel. Tonsil sections show that TIE2 expression (red) is restricted to CD31$^+$ vascular ECs (green). CD19$^+$ B cells are stained in blue. Scale bars as indicated.
Figure 6:
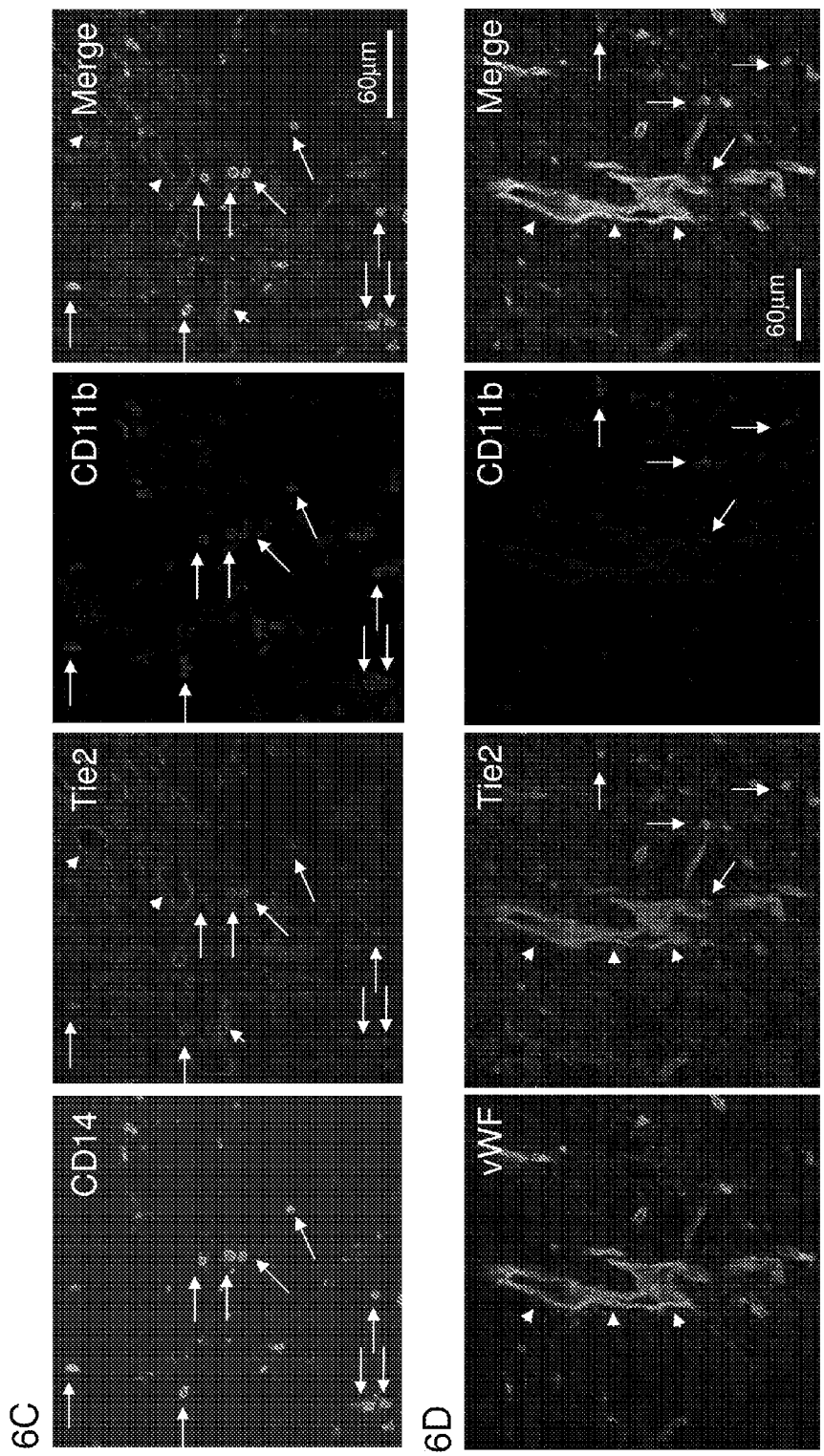
Figure 6:
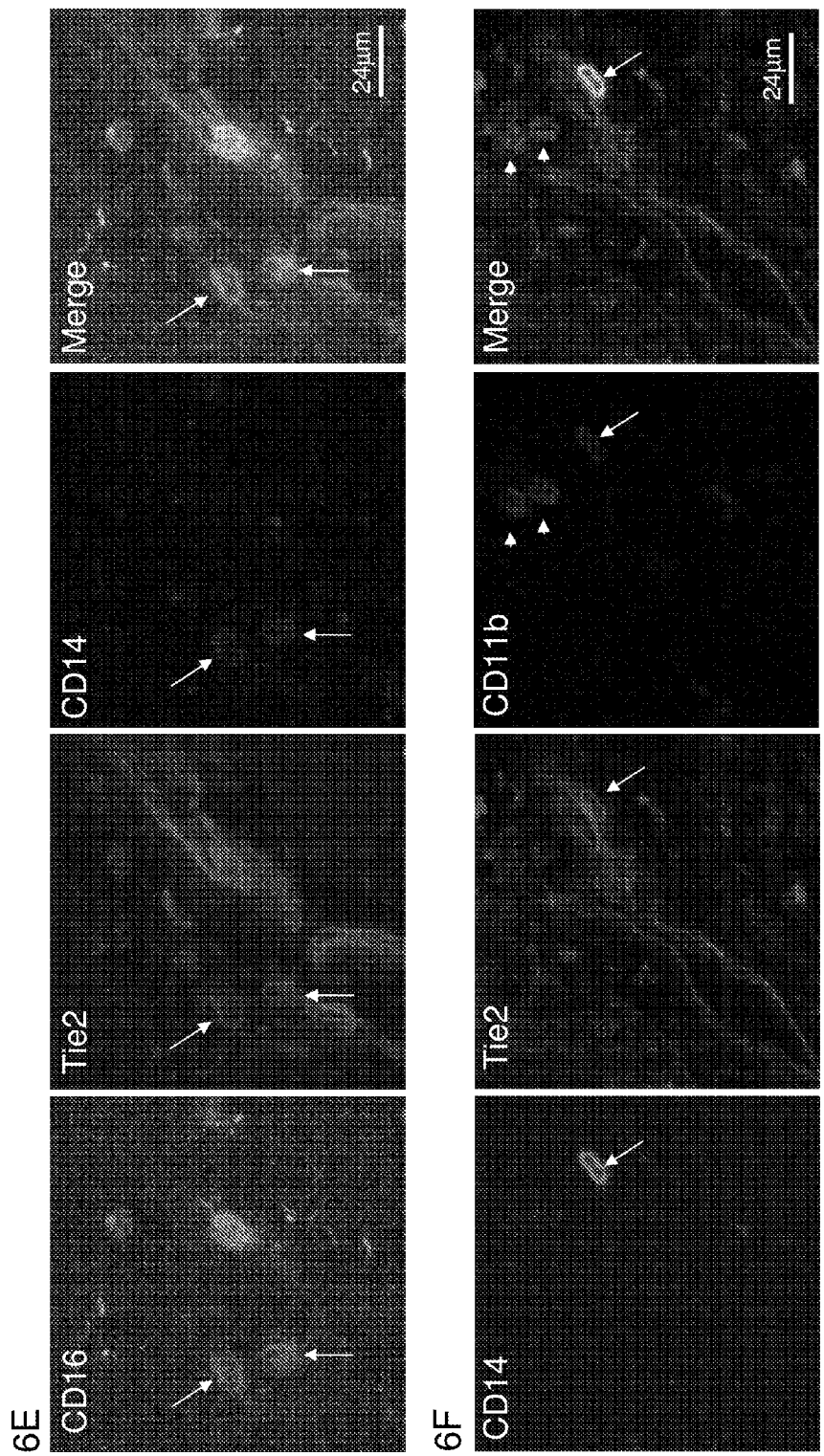

In order to confirm the hematopoietic, non-endothelial nature of the TIE2$^+$ mononuclear cells, we performed triple immunofluorescence staining and confocal microscopy on selected frozen sections obtained from different tumour specimens (n=8; FIG. 6A-F). Vascular ECs were clearly identified by their morphology, their organization in tubular structures and the co-expression of TIE2 and CD31, CD34 (not shown) or von Willenbrand Factor (vWF). Scattered TIE2$^+$ cells distinct from ECs (CD31$^-$ or CD34$^-$ or vWF$^-$) were frequently observed that co-expressed the hematopoietic marker CD45. These cells had a small, rounded shape, consistent with the morphology of monocytes and expressed the myeloid markers CD14, CD16, CD13 (not shown) and CD11b (FIG. 6A-E). These TIE2$^+$ monocytes were often found in well vascularised tumour regions and sometimes had a peri-endothelial location (FIG. 6F). Whereas the majority of CD14$^+$ monocytes were TIE2$^+$, only a minority of the total CD45$^+$ hematopoietic cells expressed TIE2, indicating that TIE2 was a distinguishing feature of tumour-infiltrating monocytes and was not expressed by the wide majority of TAMs.

Figure 6G:
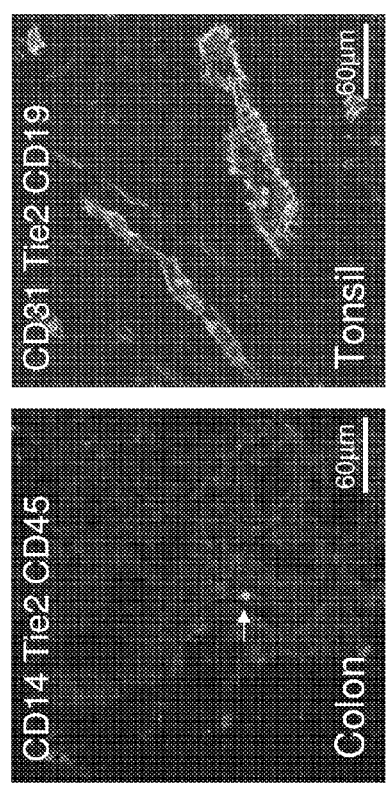

In agreement with flow analysis, we found that the non-neoplastic tissues adjacent to the tumours contained only few TIE2$^+$ hematopoietic cells (FIG. 6G). Moreover, in normal tissues obtained from surgery, we found that TIE2 expression was restricted to ECs, even in organs heavily infiltrated by hematopoietic lineage cells, such as the tonsils (FIG. 6G). Taken together, these findings indicated that human tumours selectively recruit a population of TIE2-expressing CD14$^+$ monocytes distinct from common macrophages (TAMs) and reminiscent of mouse TEMs.

Example 4

Angiopoietin-2 Exerts Chemotactic Activity on TIE2-Expressing Monocytes

Figure 7:
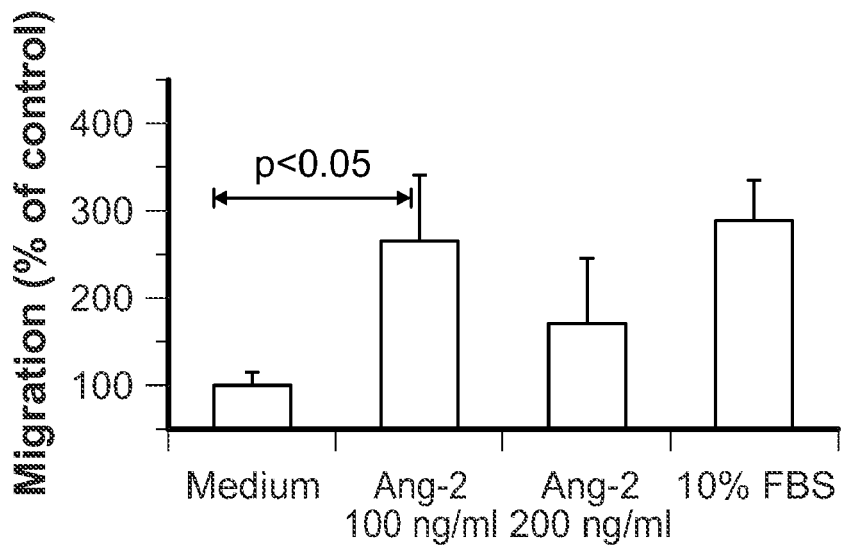
FIG. 7: Circulating TIE2$^+$ monocytes migrate towards Ang-2 and have marked pro-angiogenic activity in vivo. Modified Boyden chamber assays show migration of resident monocytes towards Ang-2. The two graphics show parts of two independent experiments of three performed. Both serum and Ang-2 induced significant migration of resident monocytes (left histograms; $p<0.05$ vs. control: Medium). Heat inactivation of Ang-2 or treatment of the cells with neutralizing anti-TIE2 antibodies, but not with control immunoglobulins, abrogate cell migration in response to Ang-2 (right histograms)
Figure 7:
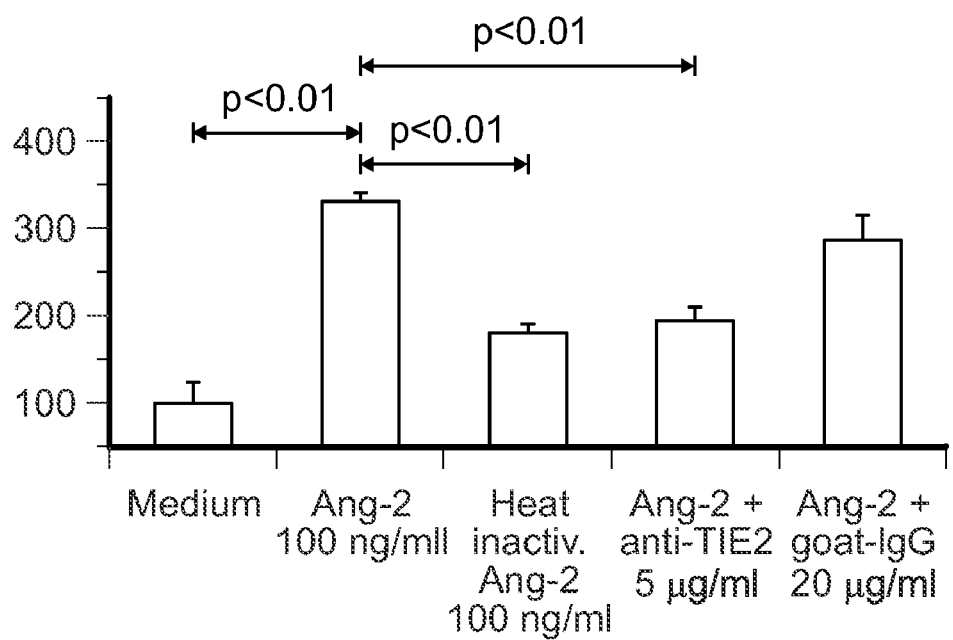

Ang-1 and Ang-2 stimulate vascular morphogenesis and shape adult angiogenesis by promoting EC chemotaxis, survival and/or apoptosis, in a context-dependent manner and in cooperation with other angiogenic factors (Jones et al., 2001). We then investigated whether Tie2 expressed by monocytes could impart similar biological responses also to these cells. Previous studies showed that Ang-2 stimulated the migration of blood-derived endothelial-like cells more efficiently than Ang-1. Using a modified Boyden chamber assay, we analyzed cell migration in response to an Ang-2 gradient. We isolated resident monocytes, which are enriched in TEMs, and inflammatory monocytes by magnetic sorting (see Methods in Example 1). As shown in FIG. 7, both serum and Ang-2 induced significant migration of resident monocytes (p<0.05 vs. control medium), with the higher response to an Ang-2 concentration of 100 ng/ml. Conversely, Ang-2 showed no significant chemotactic activity on inflammatory monocytes (data not shown). To verify that the chemotactic response observed was promoted by the specific interaction between Ang-2 and TIE2, the cells were pretreated with neutralizing anti-TIE2 antibodies. Anti-TIE2 antibodies, but not control immunoglobulins, significantly blocked Ang-2-induced cell migration. Of note, heat inactivation of Ang-2 abolished its chemotactic activity. Together, these results strongly suggest that TIE2 expressed on monocytes mediated their migration in response to Ang-2.

Example 5

Figure 8:
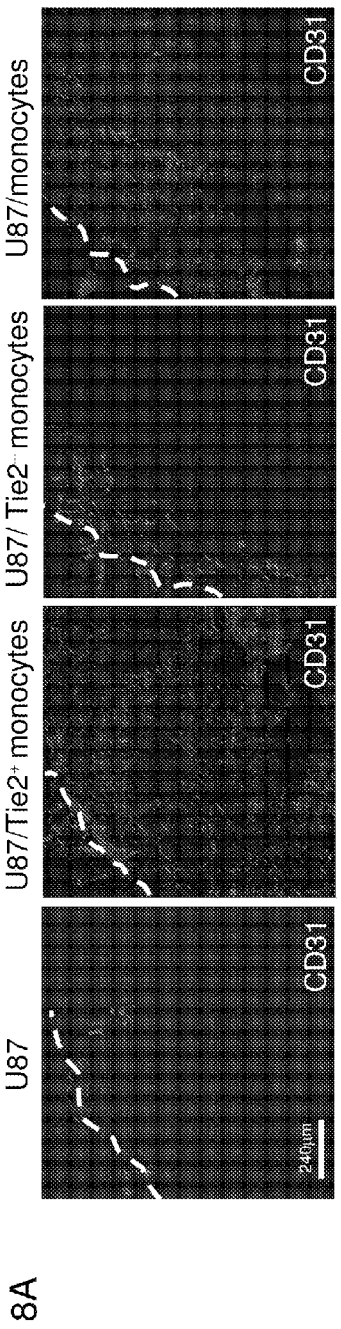
FIG. 8: Pro-angiogenic activity of circulating TEMs. Tumours were grown for 5 days subcutaneously in nude mice. (A) Representative pictures obtained by immunofluorescence staining for CD31 (red) and confocal analysis of tumours originated by the injection of U87 cells, or U87 cells co-injected with Tie2$^+$ monocytes, or U87 cells co-injected with Tie2$^-$ monocytes, or U87 cells co-injected with total monocytes, as indicated. Human glioma U87 cells were injected subcutaneously into nude mice with or without the indicated monocyte populations at 1:20 ratio. The tumour margin is indicated by a dashed line. (B) Human glioma U87 cells were injected subcutaneously into nude mice with or without the indicated monocyte populations at 1:100. The mean vascular area (n=3 tumors/group) was calculated by digital image analysis and expressed as fold increase over the value obtained in tumors from U87 cells only. Error bars indicate SD. Statistical difference between groups was calculated by Student's t Test. (C) Human glioma U87 cells were injected subcutaneously into nude mice with or without the indicated monocyte populations at 1:20 ratio.

Tie2-Expressing Monocytes are More Proangiogenic than Classical Inflammatory Monocytes We previously showed that mouse TEMs promote angiogenesis (De Palma et al., 2005). To investigate whether human TIE2$^+$ monocytes have proangiogenic activity, we isolated CD14$^+$ TIE2$^+$ and CD14$^+$TIE2$^-$ cells from human PB by cell sorting, and co-injected these cells in increasing ratios (1:100 and 1:20) with U87 human glioma cells subcutaneously in nude mice. As controls, we injected U87 cells alone and U87 cells together with unfractionated CD14$^+$ monocytes, which mostly comprise inflammatory monocytes. We studied tumour vascularisation 5 or 7 days post-injection, when tumours were at an early stage of growth (FIG. 8A).

In tumours derived from the injection of U87 cells alone (n=6), CD31$^+$ blood vessels were exceedingly scarce within the inner tumour mass, whereas few large blood vessels, likely sequestered from the subcutaneous space, surrounded the tumours. This finding indicates that angiogenesis had not yet started at this early time of tumour growth. On the contrary, tumours co-injected with human CD14$^+$TIE2$^+$ monocytes (n=6) were larger and much more vascularized, with a profuse vascular framework appreciably extending from the tumour periphery towards the inner mass. In these tumours, blood vessels had the typical morphology of angiogenic vessels (FIG. 8B). In tumours co-injected with unfractioned CD14$^+$ (n=6) or CD14$^+$TIE2$^-$ monocytes (n=6), a small rim of blood vessel ingrowths lined the tumour periphery, but only a few spots of angiogenic vessels were observed within the inner mass. Computer-assisted digital image analysis showed that the overall vascular area was significantly greater in tumours co-injected with CD14$^+$TIE2$^+$ monocytes than in control tumours and tumours co-injected with unfractioned or TIE2$^+$ monocyte-depleted CD14$^+$ cells at both cell ratios (FIG. 8B).

Taken together, these results indicated that, among human blood monocytes, the CD14$^+$TIE2$^+$ subset was specifically endowed with the ability to enhance angiogenesis in a tumour transplantation model.

Example 5

Tie2 Expression in Mouse Tumor Stroma

To identify the cell types that express Tie2 in tumors, we generated transgenic mice expressing GFP [TgN(Tie2-GFP)] under the control of a lentiviral vector (Tie2p/e LV; De Palma et al., 2003) containing transcription regulatory sequences of the Tie2/Tek gene (Jones et al., 2001). We injected the LV into the perivitelline space of fertilized oocytes, as described (Lois et al., 2002) and selected mouse lines carrying multiple vector copies per genome to amplify detection of Tie2 transcriptional activity. GFP immunofluorescence (IF) staining showed robust and EC-specific expression of GFP in all organs of TgN(Tie2-GFP) mice (n=9), including heart, liver, brain, gut and spleen.

Figure 9A:
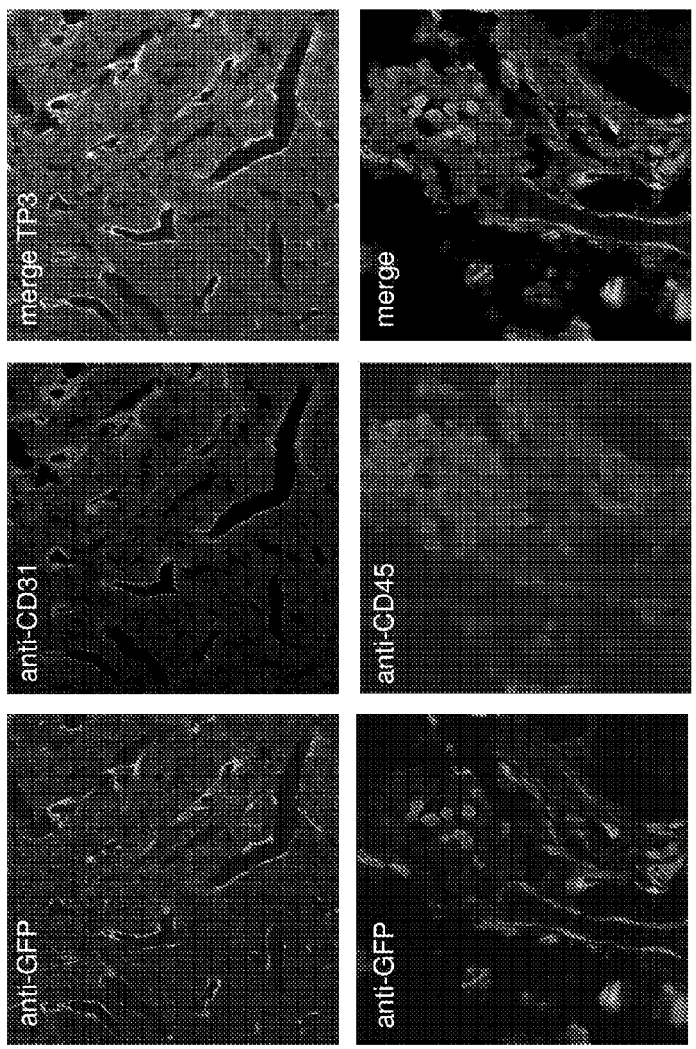
FIG. 9: Tie2 expression in tumors and in the hematopoietic system of Tie2-GFP transgenic mice. (A) Confocal IF analysis of N202 tumors shows GFP expression (green) in CD31$^+$ ECs (red) and in CD45$^+$ TEMs (arrows; red). Nuclei labeled by TO-PRO-3 (TP3, blue). Scale bar=120 μm. (B)-(D) Tumor FACS analysis. All GFP$^+$ cells expressed Tie2 and Sca-1 (dot plots on the left). The Tie2$^+$GFP$^+$ cells (density plots on the right) were CD45$^+$CD11b$^+$TEMs, CD45$^{Neg}$CD31$^+$ ECs, or CD45$^{Neg}$CD31$^{Neg}$ cells. The Tie2$^+$GFP$^+$CD45$^+$ TEMs were c-kit$^{Neg}$. (E) and (F) BM FACS analysis. The GFP$^+$ cells (dot plots on the left) were enriched in Sca-1$^+$ cells (open histogram; filled histogram is the IgG isotype control) and CD45$^+$ c-kit$^+$ cells. GFP was also expressed by CD45$^+$CD11b$^+$ myeloid cells (density plots on the right). (G) and (H) PB FACS analysis. The GFP$^+$ cells were monocytes (dot plots on the bottom left; L, lymphocytes; M, monocytes; G, granulocytes) and were mostly CD45$^+$CD11b$^+$/CD45$^+$ c-kit$^{Neg}$/CD45$^+$CD31$^{Neg}$ myeloid-lineage hematopoietic TEMs (density plots on the right).
Figure 9B:
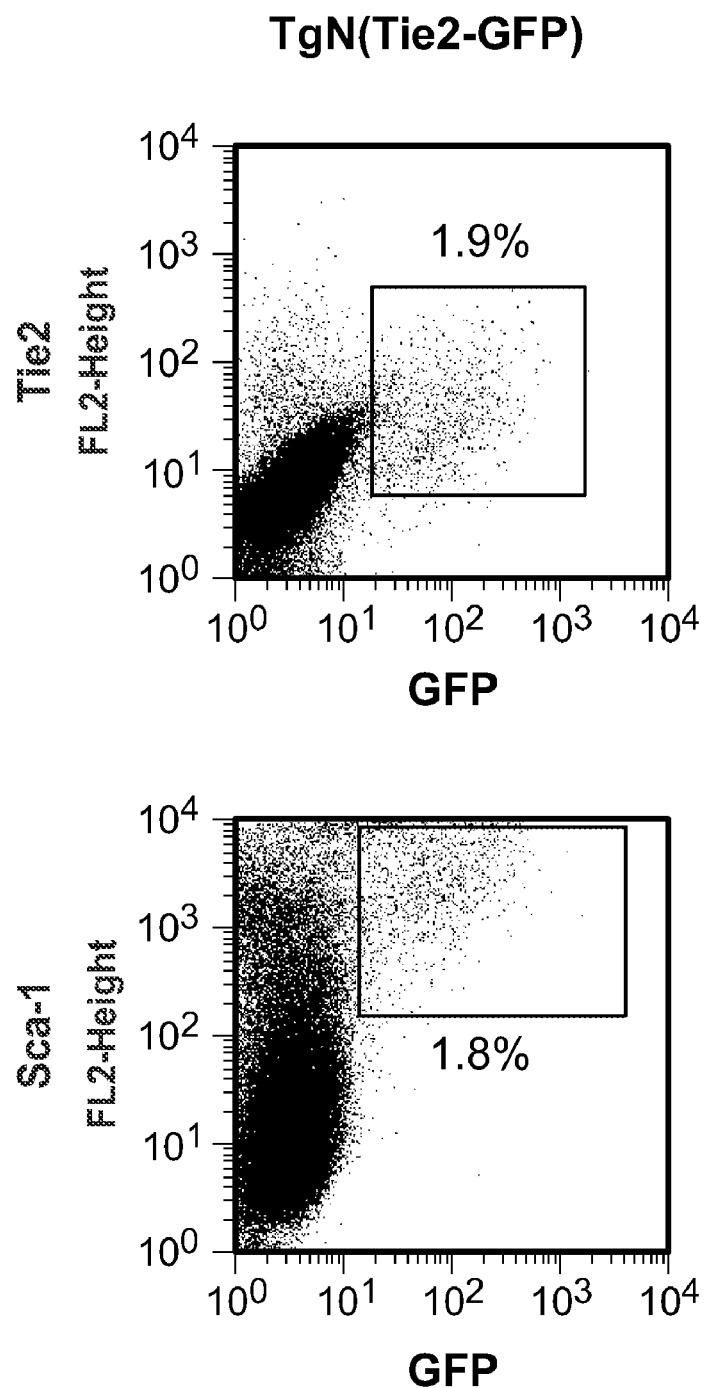

We then analyzed N202 mouse mammary tumors grown subcutaneously (s.c.) and found that GFP was expressed in the majority of vascular ECs and by a small fraction of tumor-infiltrating leukocytes, identified as TEMs. Fluorescence-activated cell sorting (FACS) of tumors made into single cell suspensions showed that that the Tie2-GFP$^+$ cells were uniformly Tie2$^+$ and Sca-1$^+$ and accounted for 1%-2% of the total cells (FIG. 9A-B). The majority of the tumor-derived Tie2-GFP$^+$ cells were ECs (Tie2CD31$^+$CD45$^-$), whereas ~5% were identified as Tie2$^+$CD11b$^+$CD45$^+$ TEMs. These TEMs, which expressed Sca-1, were c-kit-. Interestingly, a significant fraction of tumor-derived Tie2-GFP$^+$ cells were Tie2$^+$CD31$^-$CD45$^-$ (FIG. 9A-B). In summary, three distinct cell populations expressed Tie2 in tumor grafts: vascular ECs, hematopoietic TEMs, and a population of stromal cells distinct from ECs and HCs.

Example 6

Tie2 Expression in the Mouse Hematopoietic System

Figure 9C:
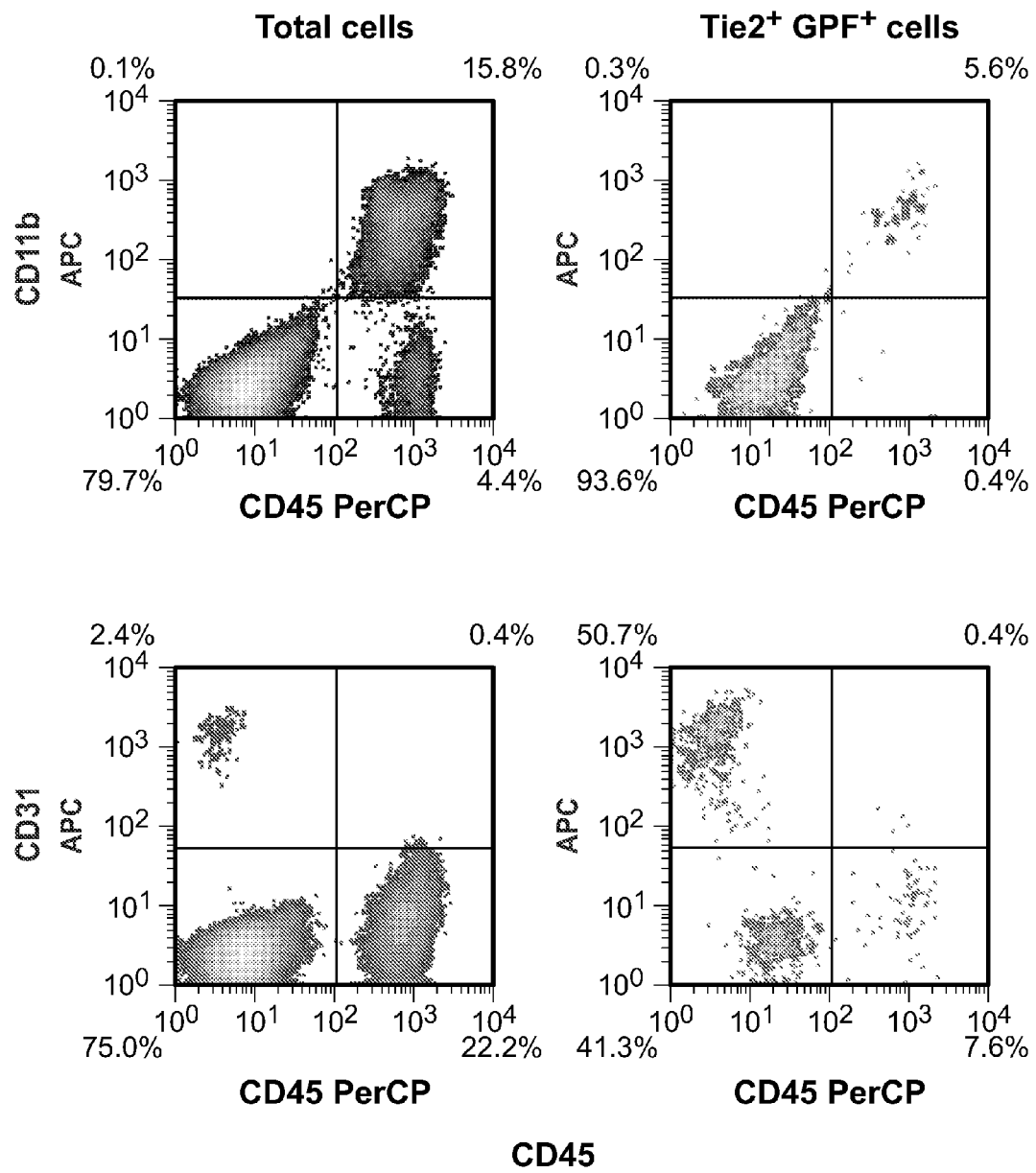
Figure 9D:
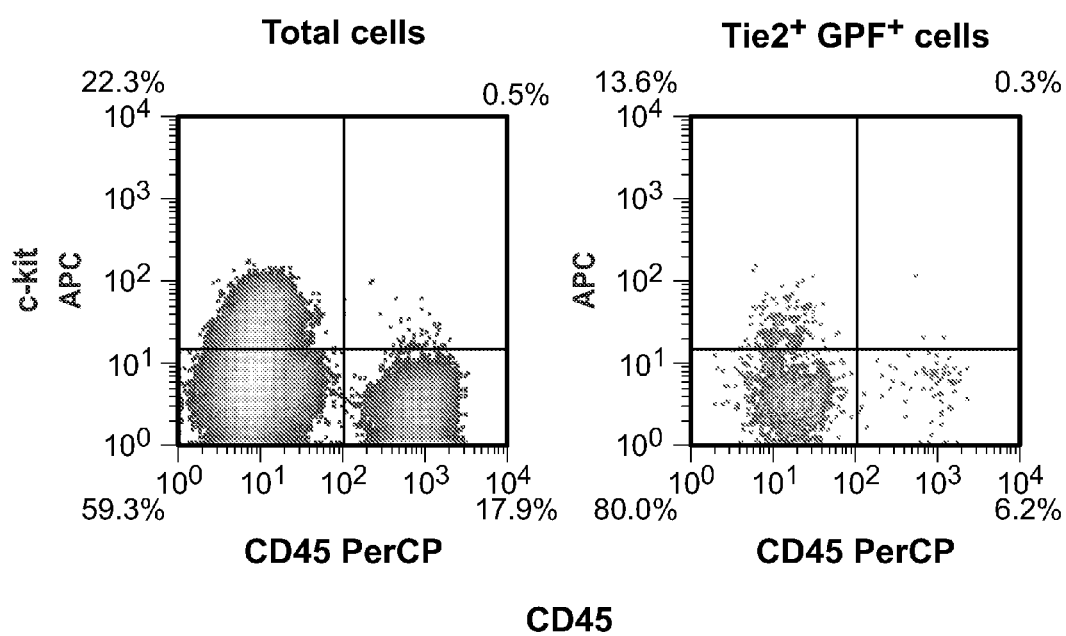
Figure 9E:
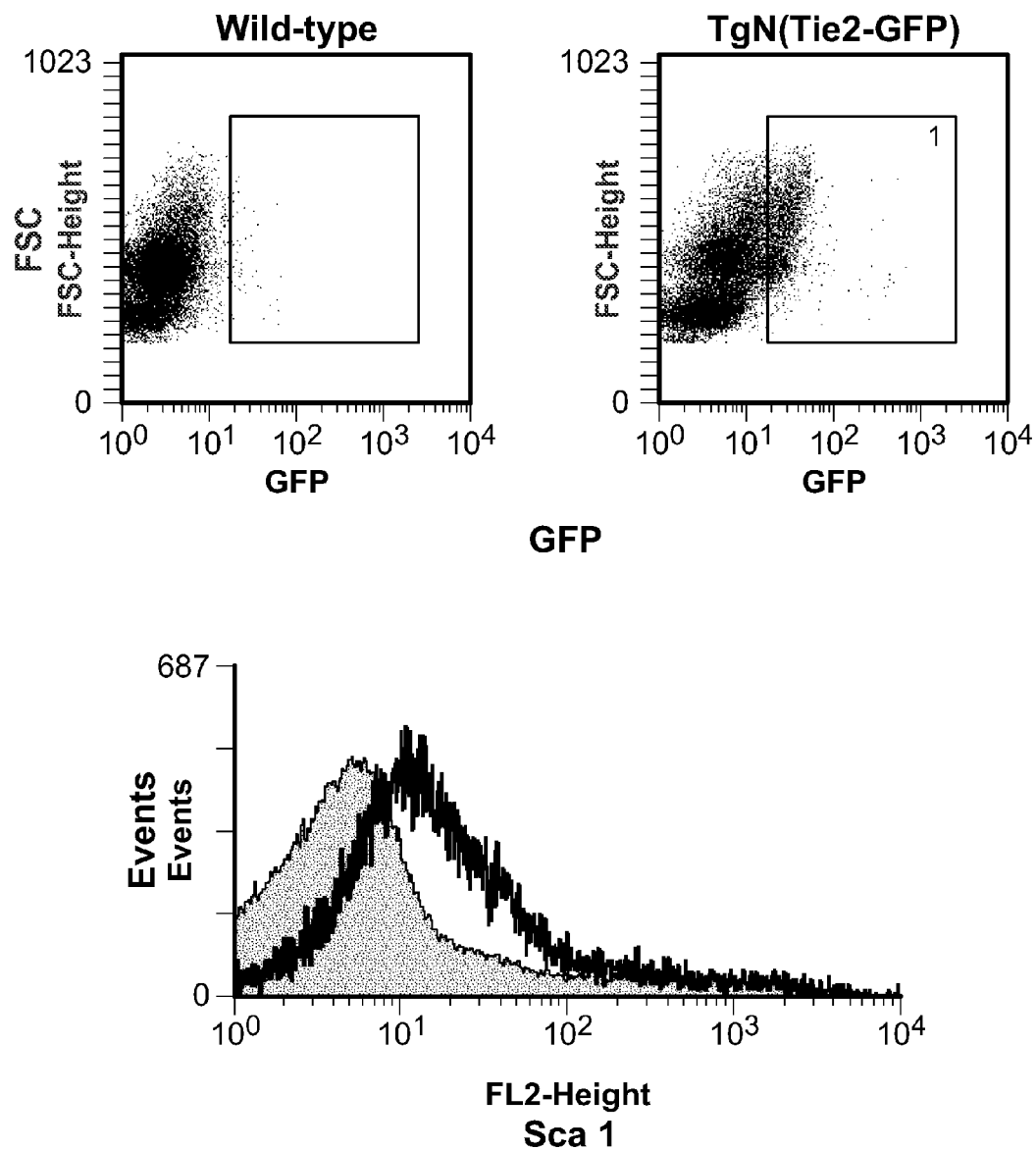
Figure 9F:
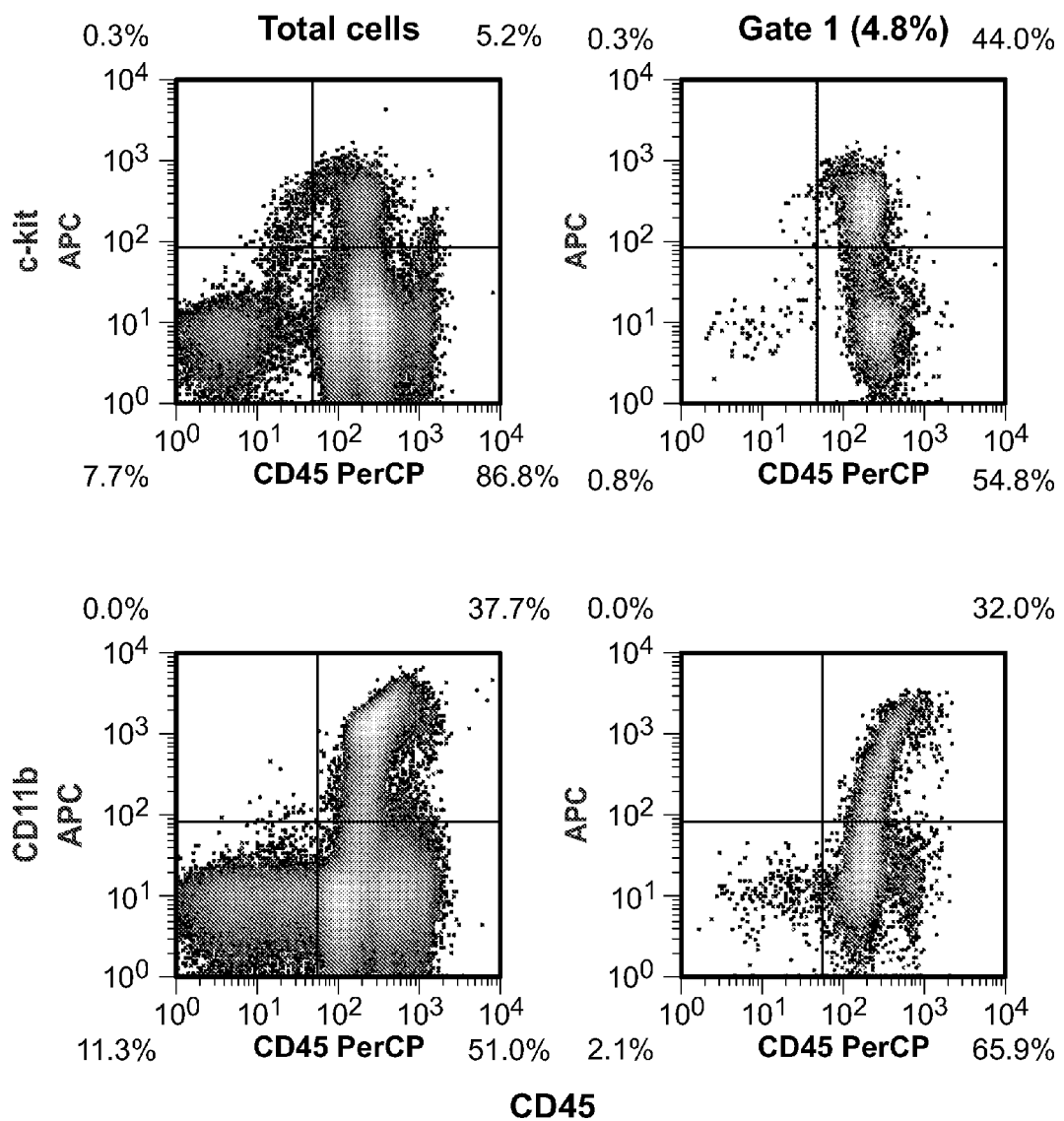
Figure 9G:
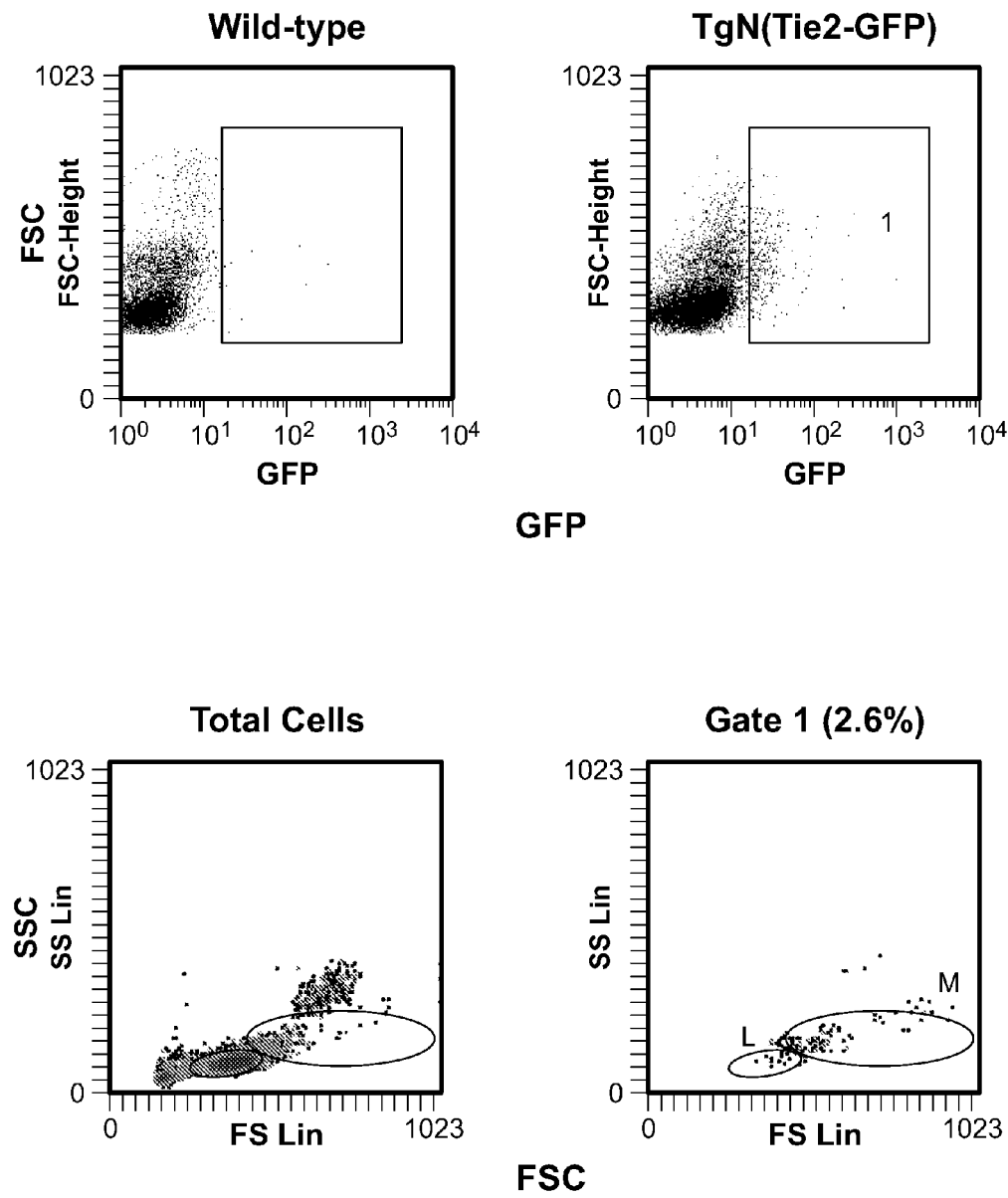
Figure 9H:
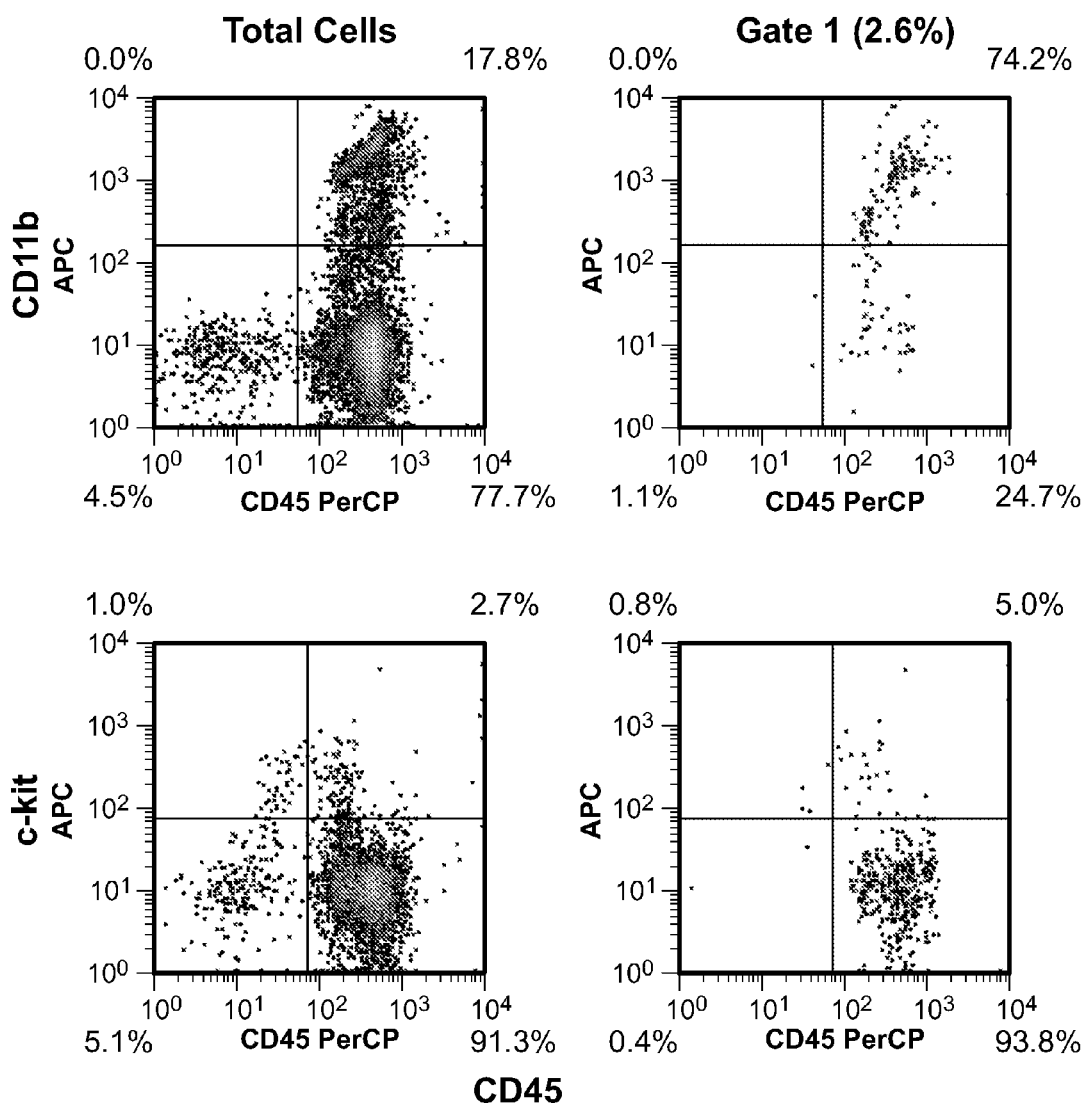

We analyzed GFP expression in the bone marrow (BM) and peripheral blood (PB) of TgN(Tie2-GFP) mice (FIG. 9C-D). Two to five percent of BM cells were Tie2$^-$GFP$^+$ (FIG. 9C). FACS analysis showed that these Tie2$^-$GFP$^+$ cells were endothelial cells (ECs) (<5% CD31$^+$CD45$^-$) and hematopoietic cells (HCs) (>95% CD45$^+$). The Tie2-GFP$^+$ HCs were enriched in Sca-1$^+$ (~30%) and c-kit$^+$ (~50%) progenitors. Colony-forming cell (CFC) assays of sorted cells showed that the Tie2-GFP$^+$ fraction of c-kit$^+$CD45$^+$ BM cells did not form colonies, in contrast to the Tie2-GFP$^-$ fraction, which gave 10% outgrowth, suggesting that Tie2 expression was associated with the more primitive HPCs (hematopoietic progenitor cells)/hematopoietic stem cells (HSCs). In agreement with this notion, we showed that Tie2 receptor$^+$ HCs were highly enriched in the BM HSC fraction of wild-type mice. Interestingly, the Tie2-GFP$^+$ HCs of the BM of TgN(Tie2-GFP) mice also contained a population of myeloid lineage (CD45$^+$ CD11b$^+$) cells. These cells were distinct from committed progenitors, because they did not form colonies in CFC assays. Thus, in the BM, Tie2 was expressed by ECs and putative HSCs, as shown in previous studies (Arai et al., 2004) and by a subset of myeloid lineage cells distinct from HPCs.

In the PB (FIG. 9D), a small fraction (~1%-2%) of the leukocytes were identified as TEMs (Tie2-GFP$^+$). These circulating TEMs were 99% CD45$^+$ and >85% CD11b$^+$, accounted for approximately 10% of the total myeloid CD11b$^+$ cells, were distinct from granulocytes according to light scattering features and the expression of Gr-1, and mostly did not express the HSC/HPC markers c-kit (95% c-kit$^-$) and Sca-1 (>70% Sca-1$^-$). TEMs did not express the B cell marker CD19, the T cell marker CD3, or the pan-NK marker CD49b. In addition, TEMs were CD31 Low and VEGFR-2- and thus were distinct from EPCs and CECs. In summary, the phenotype of circulating TEMs indicates that they represent a distinct subset of monocytes.

Example 7

Generation of Conditional Angiogenesis-Defective Transgenic Mice

To study the function of the different Tie2$^+$ cell types observed in tumors, we generated transgenic mice expressing the conditionally toxic gene thymidine kinase (tk) under the control of the Tie2p/e LV [TgN(Tie2-tk)]. In these mice, GFP expression was linked to that of tk by an IRES element. The GFP pattern in TgN(Tie2-tk) mice was similar to that observed in TgN(Tie2-GFP) mice, although the expression level was weaker because it was IRES dependent, and labelling with anti-GFP antibodies was required to detect GFP expression.

Example 8

Elimination of Mouse TEMs Without Myelosuppression and Without Loss of Long-Term Repopulating HSCs Although Tie2 is likely expressed by HSCs, GCV-treated TgN(Tie2-tk) mice had normal hematopoiesis for up to 8 weeks after the end of the treatment, the longest time point analyzed. GCV-treated mice, however, had substantially reduced frequency of Tie2-GFP$^+$ cells in the BM and almost no circulating TEMs in PB. Despite the depletion of the majority of Tie2-expressing cells, BM cells exposed to GCV in vivo remained capable of radioprotecting lethally irradiated mice in a BM transplantation (BMT) model. Eight weeks after the transplant, all recipients were surviving and had normal hematopoiesis, indicating long-term engraftment of Tie2-tk BM cells exposed to GCV. These results strongly suggested that HSCs, even if they expressed Tie2, were resistant to GCV. Furthermore, because elimination of the majority of the BM Tie2-GFP$^+$ cells did not cause obvious myelotoxicity in GCV-treated mice, the GCV-sensitive Tie2-GFP$^+$ cells likely represented a specific lineage of HCs, rather than multipotent HPCs Example 9

Mouse Tumor TEMs Promote Angiogenesis

Figure 10A:
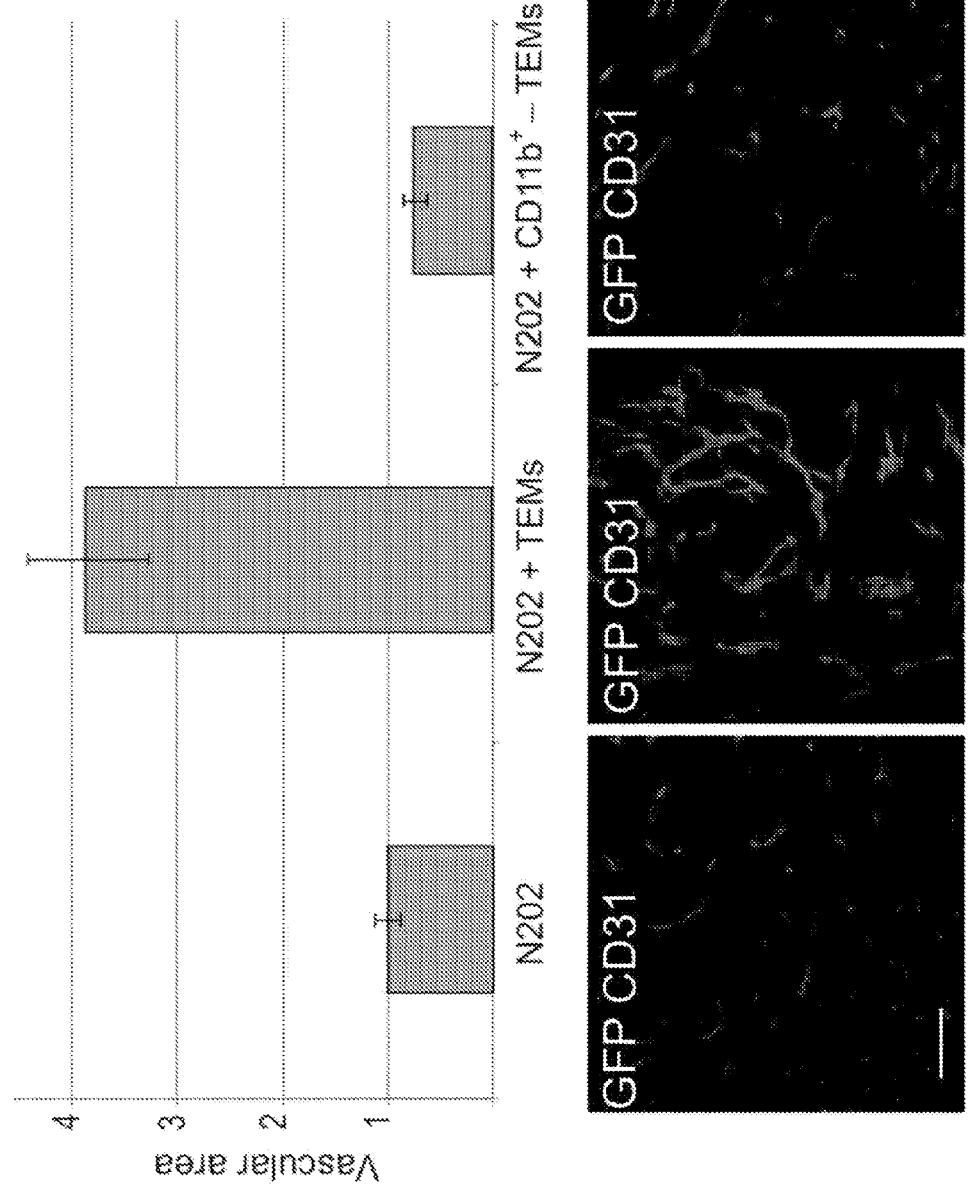
FIG. 10. Pro-angiogenic activity of tumor and circulating TEMs. (A) Vascular area (histograms showing fold increase over reference value) in tumors originated from the injection of N202 cells (n=3; reference value), N202 cells and TEMs (n=3), or N202 cells and CD11b$^+$ myeloid cells depleted of TEMs (n=3), and grown for 5 days in nude mice. Representative pictures of tumor sections immunostained for CD31 (red) and GFP (green) are shown on the bottom. Scale bar=120 μm. (B) Confocal IF analysis for NG2 (green), CD45, or CD34 (red), and TP3 (blue) staining of tumors originated by the injection of N202 cells (left) or N202 cells and TEMs (right), as in A. Scale bar=120 μm. (C) Average number of cell nuclei (black bars) and of nuclei belonging to CD34$^+$ vascular structures (gray bars) per 200× microscope field in matrigel sections. Matrigel alone (n=3), matrigel containing TEMs (n=5), matrigel containing an excess of PBMCs (n=2), or matrigel containing PBMCs depleted of TEMs (n=5) were injected 8 days earlier s.c. in nude mice. Representative pictures of sections immunostained for CD34 (red) and stained with TP3 (blue) are shown on the bottom. Scale bar=120 μm. (D) N202 tumor growth in wild-type FVB mice transplanted with transgenic Tie2-tk BM cells 8 weeks earlier, and either treated with GCV for the indicated time (n=5), or left untreated (n=5).
Figure 10B:
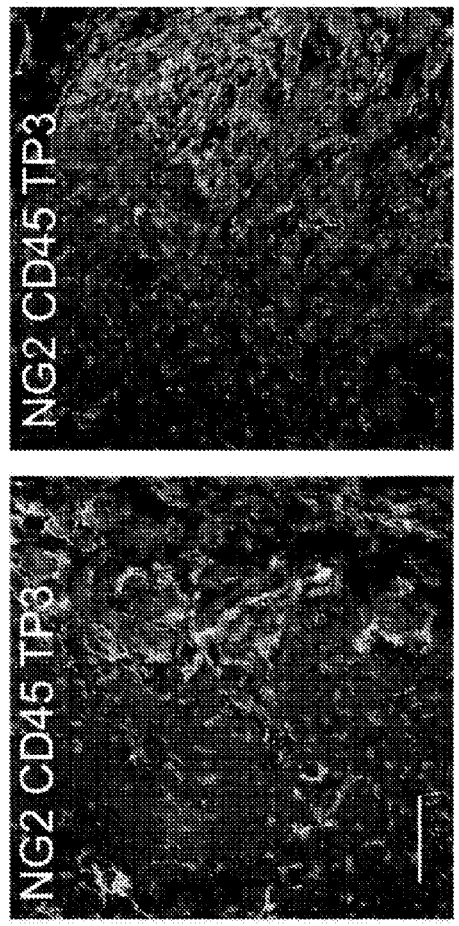

To directly assay the proangiogenic activity of tumor TEMs, we isolated GFP$^+$CD11b$^+$ cells from N202 tumors grown in TgN(Tie2-GFP) mice by FACS and injected these cells (>95% purity) together with N202 tumor cells (1:20 ratio; 2.5×10$^4$ TEMs) in nude mice (FIG. 10A-B). As controls, we injected N202 cells alone, and N202 cells with GFP-CD11b$^+$ tumor-derived myeloid cells, which included all myeloid lineage cells, except for TEMs. We studied tumor vascularisation 6 days postinjection, when tumors were at an early stage of growth and had a diameter of 2-3 mm. We observed scant vascularisation in tumors (n=3) derived from the injection of N202 cells alone. In these tumors, CD31$^+$ or CD34$^+$ blood vessels were few, had a small diameter, and were little branched. On the contrary, tumor challenges coinjected with TEMs (n=3) were much more vascularised, and the blood vessels were larger and irregularly shaped and had a more developed branching pattern (FIG. 10A). Computer-assisted digital image analysis showed that the overall vascular area was 4-fold higher in tumors coinjected with TEMs than in control tumors (FIG. 10A) Interestingly, tumor angiogenesis was not enhanced by the coinjection of N202 cells and CD11b$^+$ myeloid cells depleted of TEMs (n=3). These results indicated that TEMs have a superior proangiogenic activity among tumor-infiltrating myeloid cells. We did not detect GFP$^+$ cells in the tumors 6 days after injection of the cells, suggesting a rapid turnover of TEMs in growing tumors, a circumstance that argues against the possibility that these cells are immature HPCs. Interestingly, all tumors displayed abundant infiltration of both CD45$^+$ hematopoietic cells and NG2$^+$ pericytes/myofibroblasts, suggesting that these cells colonize tumors during the early stages of development, possibly before a functional vasculature has been established, or in concomitance with the angiogenic switch (FIG. 10B).

Example 10

Figure 10C:
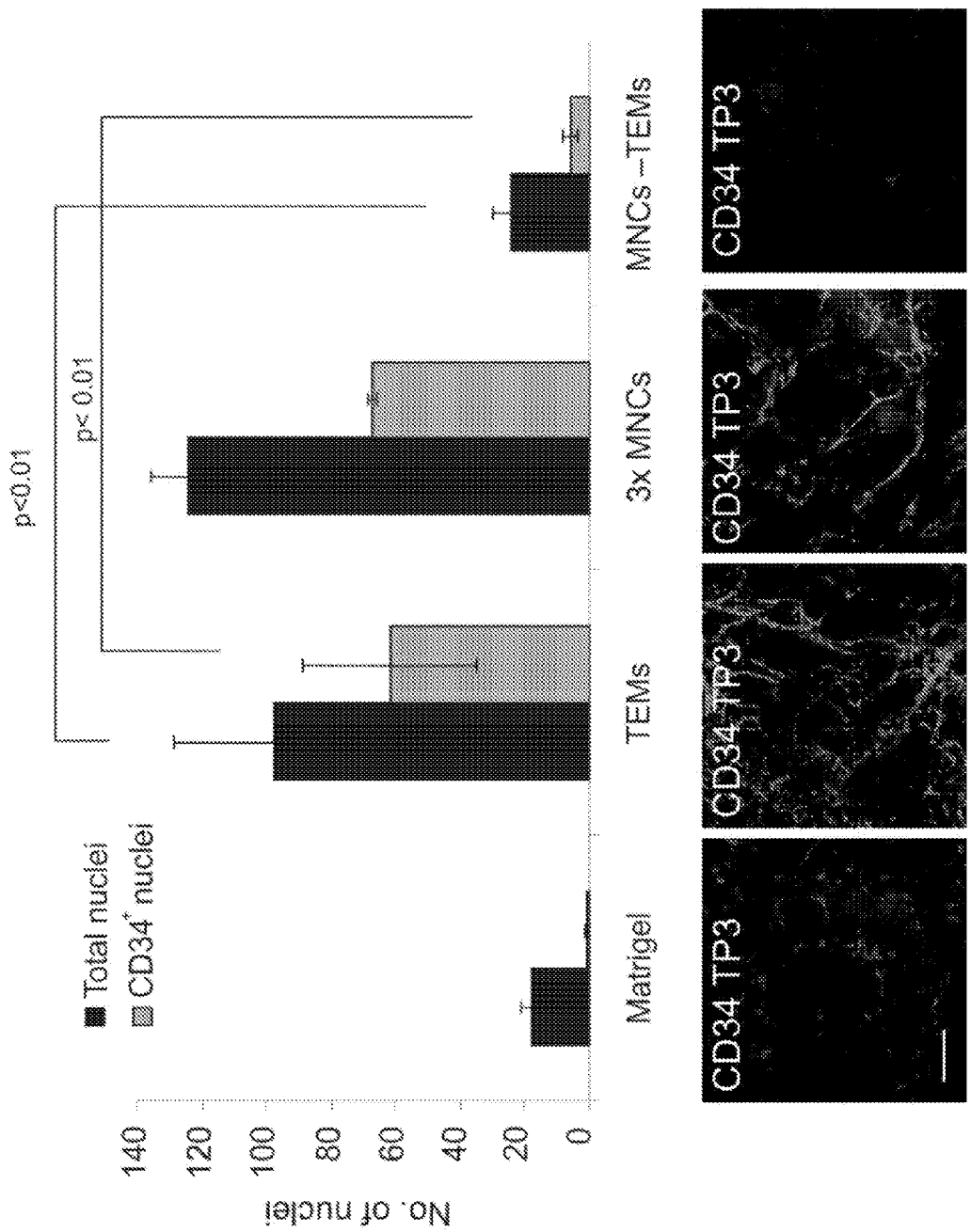

Circulating Mouse TEMs Promote Angiogenesis and are the Likely Precursors of Tumor TEMs To explore the relationship between circulating and tumor-homing TEMs, and to investigate whether commitment to a proangiogenic function already occurs in circulating cells rather than being locally induced within the tumor stroma, we purified TEMs from the PB of TgN(Tie2-GFP) mice by FACS (purity>95%) and tested their proangiogenic activity in an in vivo matrigel plug assay (FIG. 10C). We injected matrigel alone (n=3), or matrigel containing freshly isolated TEMs ($7 \times 10^4$ cells; n=5), or an equal number of peripheral blood mononuclear cells (PBMCs) depleted of TEMs (n=5), or an excess of total PBMCs ($2.5 \times 10^5$ cells; n=2), s.c. in nude mice. We excised matrigel plugs 8 days later and found that, while matrigel alone contained few cells, TEMs induced a robust capillary network, as shown by CD34 immunostaining of matrigel sections Remarkably, PBMCs depleted of TEMs did not induce significant angiogenesis in matrigel (p<0.01 versus TEMs), and an excess of total PBMCs was no more effective than purified TEMs. Thus, PB TEMs had superior capacity to trigger an early angiogenic response among PBMCs in the experimental conditions used (FIG. 10C).

Figure 10D:
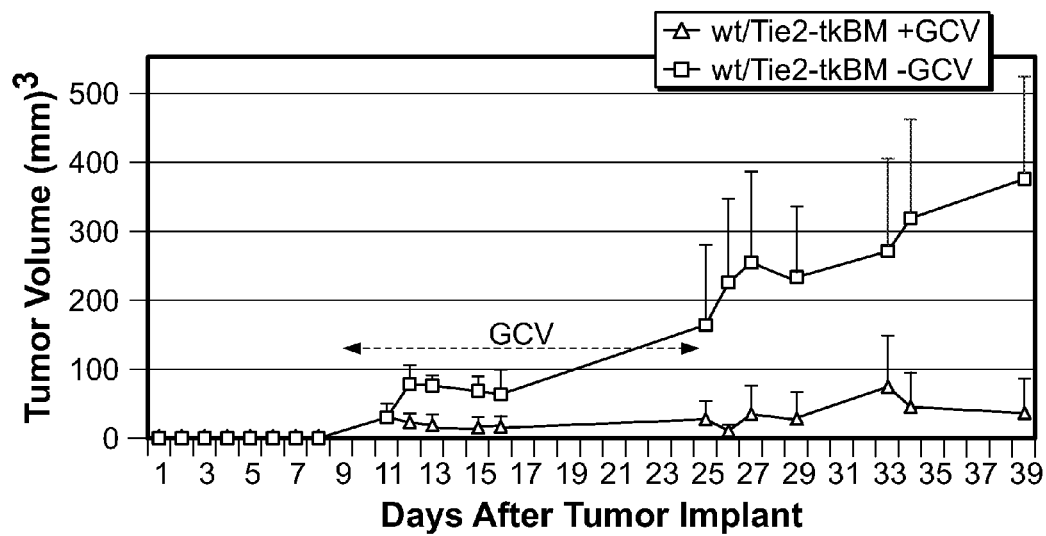

The proangiogenic activity of PB TEMs suggested that these cells were the likely precursors of tumor TEMs. To further investigate this relationship, we transplanted wild-type mice with TgN(Tie2-tk) transgenic BM cells, and 8 weeks later we challenged them with N202 tumors and administered GCV before the tumors became visible, in order to eliminate TEMs before they reached the tumor site (FIG. 10D). GCV-treated mice (n=5) showed a drastically reduced tumor growth as compared with untreated mice (n=5), indicating that elimination of circulating TEMs was sufficient to inhibit tumor growth. Interestingly when we stopped GCV treatment, the tumors remained dormant for more than 2 weeks before resuming their growth (date not shown), suggesting that reconstitution of the TEM lineage was required before the tumors could turn on angiogenesis and resume their growth. Taken together, these findings imply that circulating TEMs represent a distinct lineage of proangiogenic monocytes required to promote vascular growth in vivo.

Example 11

Figure 11A:
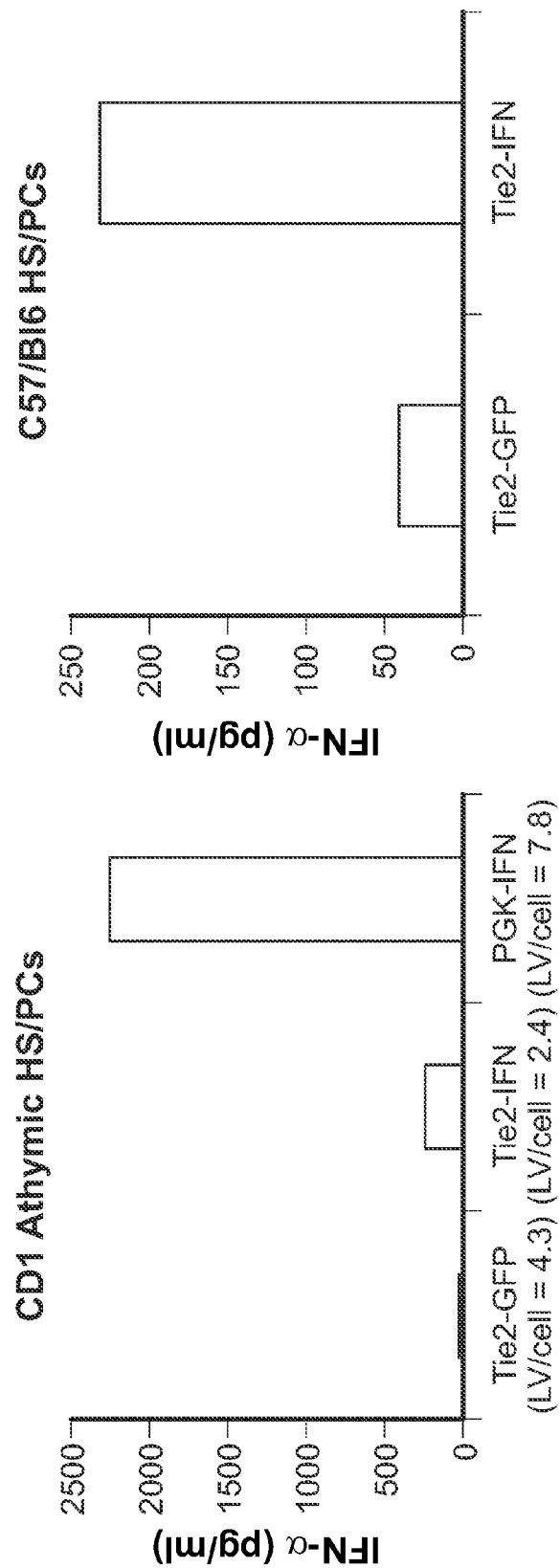
FIG. 11: Gene modified TEMs target an interferon-alpha transgene to tumors and inhibit tumor growth (A) IFN-α expression by LV-transduced HS/PCs. Cells were transduced (day 0) with p24-matched LV doses and cultured in vitro for 9 days. At day 9, medium was collected and IFN-α measured by ELISA (R&D Systems). Cells were collected to measure LV integration amounts by qPCR. Left histogram shows HS/PCs isolated from the BM of CD1 athymic mice and transduced by control Tie2-GFP, Tie2-IFN and PGK-IFN LVs. Right histogram shows HS/PCs isolated from the BM of C57B1/6 mice and transduced by control Tie2-GFP and Tie2-IFN LVs. Two of three experiments performed are shown. (B): Survival proportions of BM-transplanted mice. Lethally irradiated (975 cGy) CD1 athymic mice were transplanted with 106 LV-transduced HS/PCs. All mice transplanted with PGK-IFN LV-transduced HS/PCs died between 10 and 12 days post-transplant, whereas all Tie2-GFP and PGK-GFP (GFP), and Tie2-IFN BM-transplanted mice survived until the end of the experiments. (C) Representative photos of mouse heart endothelial cells (top panels) and U87 human glioma cells (bottom panels) cultured in the presence of conditioned medium from PGK-IFN LV-transduced N202 cells. IFN-α concentration in conditioned medium of IFN-α-expressing N202 cells was determined by ELISA. IFN-α-containing medium was then diluted in fresh medium to a final concentration of 0.5 and 2.5 ng/ml. Cells were cultured for 7 days, and then stained with 3-(4,5-Dimethylthiazol-2-yl)-2,5-diphenyltetrazolium bromide (MTT) to identify viable cells (showing dark mitochondrial staining). Whereas mouse heart endothelial cell proliferation was inhibited by IFN-α, U87 human glioma cells were not inhibited at the same IFN-α doses, nor were they inhibited when exposed to mouse recombinant IFN-α (r-IFN-α). (D) and (E) Inhibition of orthotopic human gliomas in Tie2-IFN BM-transplanted mice Glioma growth (volume determined by MRI) in individual BM-transplanted mice. Mice were transplanted with Tie2-GFP (n=5), PGK-GFP (n=7) or Tie2-IFN (n=10) LV-transduced HS/PCs. Note that some mice were euthanized between 3 and 5 weeks PTI for further analyses. (E) Contrast-enhanced T1-weighted coronal MRI analyses of tumor growth in representative control PGK-GFP and Tie2-IFN mice. Tumor growth was analyzed at the indicated time-points PTI. Intracranial gliomas are indicated by arrows and dashed line. (F) Inhibition of tumor angiogenesis in orthotopic human gliomas of Tie2-IFN BM-transplanted mice. GFP, Ki-67 or Caspase-3 (Casp-3; green), CD31 or IFN-α (red) and CD11b (blue) immunofluorescence staining, and TP3 (blue) staining of intracranial gliomas grown in Tie2-GFP (n=5) and Tie2-IFN (n=6) mice. Top panels: Inset in rightmost panel shows high-power magnification of an IFN-α-expressing cell. Bottom panels: Inset in top left panel shows high-power magnification of Ki-67+ ECs. Arrows show Ki-67+ or Caspase-3+ ECs, as indicated. The dashed lines indicate tumor perimeter. Brain sections were analyzed between 3 and 5 weeks PTI. (G) Inhibition of tumor angiogenesis in orthotopic human gliomas of Tie2-IFN BM-transplanted mice. Top panels: NG2 (green), CD31 (red) and CD11b (blue) immunofluorescence staining, and TP3 (blue) staining of intracranial gliomas grown in Tie2-GFP (n=5) and Tie2-IFN (n=6) mice. The rightmost panel shows a high-power magnification of a tumor vessel covered by NG2+ pericytes. Bottom left panel: Glioma grown in a Tie2-IFN mouse. The dense TP3 nuclear indicates tumor mass. Bottom left panel: Vascular area (histograms showing fold-change over reference value) in intracranial gliomas grown in control (GFP, including Tie2-GFP (n=5) and PGK-GFP (n=3) tumors) and Tie2-IFN (n=5) mice. Representative pictures of tumor sections immunostained for CD31 are shown on the bottom. Brain sections were analyzed between 3 and 5 weeks PTI. (H) Tumor stroma-targeted IFN response in Tie2-IFN BM-transplanted mice, RNase protection assay performed using mouse gene probes (left) shows strong upregulation of the IFN-inducible gene 2'5'-OAS/OAS1 in tumor tissue (T) of Tie2-IFN mice, but not in tumor tissue (T) of PGK-GFP mice or in the contralateral brain parenchyma (P) of either Tie2-IFN or PGK-GFP mice. Note that the proinflammatory cytokines TNF-α, IL-1a and IL-1b were also upregulated in tumors of Tie2-IFN mice. Similar assay performed using human gene probes (right) shows only minimal expression of 2'5'-OAS. The housekeeping gene L32 is used to estimate the amount of mouse and human mRNA in each sample. Rightmost lanes in both panels represent positive controls. Results representative of 4 Tie2-IFN and 4 PGK-GFP mice analyzed at 4-5 weeks PTI. (I) Hemocytometric blood cell counts of selected CD1 athymic BM-transplanted mice. Peripheral blood was collected by intracardiac puncture of deeply anaesthetized mice between 3 and 5 weeks PTI. Fifty µl of heparinised blood were analyzed by a hemocytometer. Note the marked thrombocytopenic condition of s-IFN mice. Blood cells counts were similar in Tie2-GFP, PGK-GFP and Tie2-IFN mice. Similar results were obtained in FVB and C57B1/6 BM-transplanted mice. t test statistical analysis shows p values for all groups. WBC, white blood cells; RBC, red blood cells; HGB, haemoglobin; HCT, hematocrit; PLT, platelets. (J) Tie2 expression by qPCR in FACS-sorted TEMs and ECs, as indicated. Relative quantification values of Tie2 transcript are shown as fold-change over reference value (Tie2 expression in TEMs isolated from peripheral blood, PB). For each relative value, an interval of confidence was calculated; confidence intervals that do not overlap indicate statistically significant differences (p<0.05). Results shown as average±SEM of two independent samples analyzed in 4 technical replicates. (K) Lack of antitumor activity in mice expressing systemic IFN-α. Top panels: hematoxylin/eosin staining of representative brain sections showing intracranial gliomas injected in Tie2-GFP (left) and Tie2-IFN (middle) BM-transplanted mice, and in Tie2-GFP BM-transplanted mice engineered to express systemic IFN-α (s-IFN; right). Arrows indicate tumor margin; (*) and arrowheads indicate central hemorrhage in s-IFN tumors. Bottom left panel: brain tumor growth (average volume±SEM by MRI analyses at 3 weeks PTI) in Tie2-GFP and PGK-GFP (GFP, n=11), Tie2-IFN (n=9) and s-IFN (n=4) BM-transplanted mice. Bottom right panel: GFP (green), CD31 (red) and CD11b (blue) immunofluorescence staining of an intracranial glioma grown in a s-IFN mouse. Note GFP+ TEMs surrounding CD31+ angiogenic blood vessels. Brain sections were analyzed between 3 and 5 weeks PTI.
Figure 11:
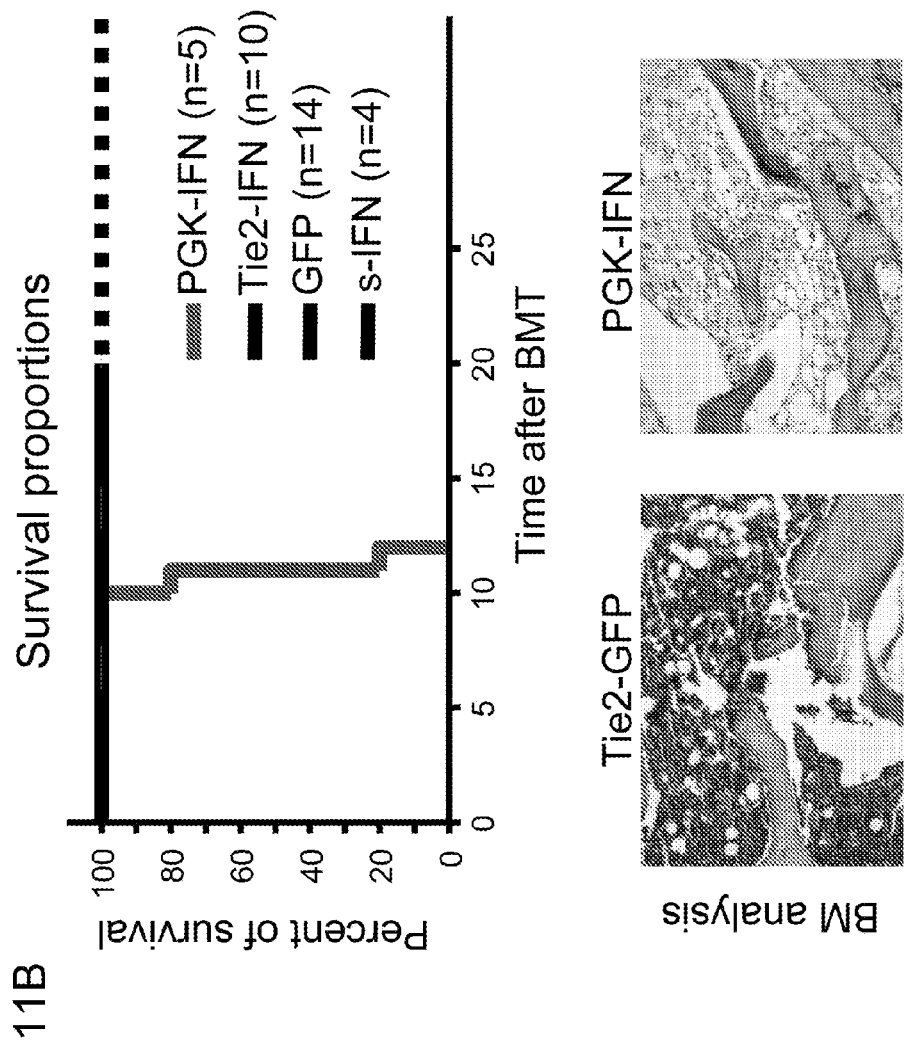
Figure 11:
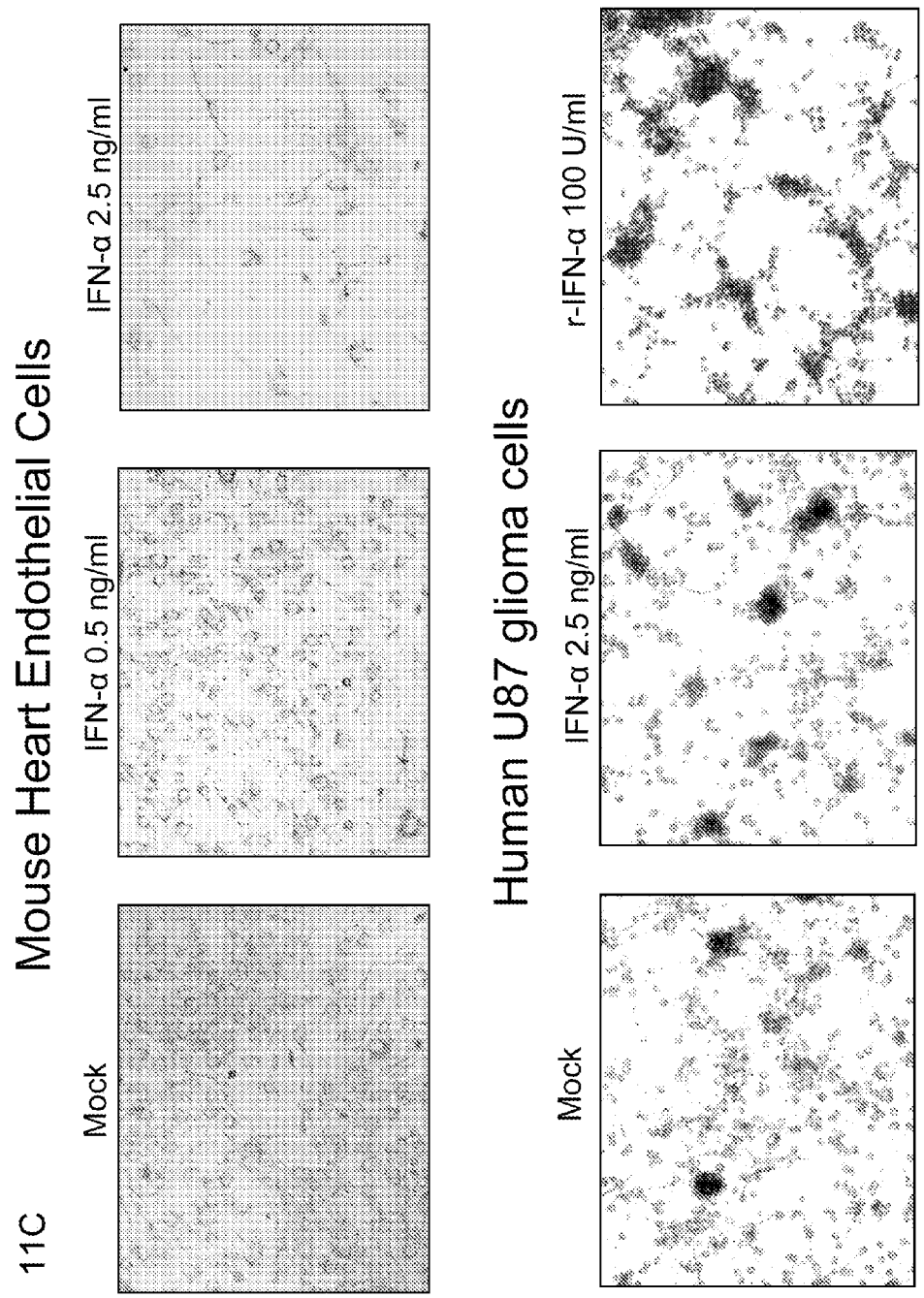
Figure 11:
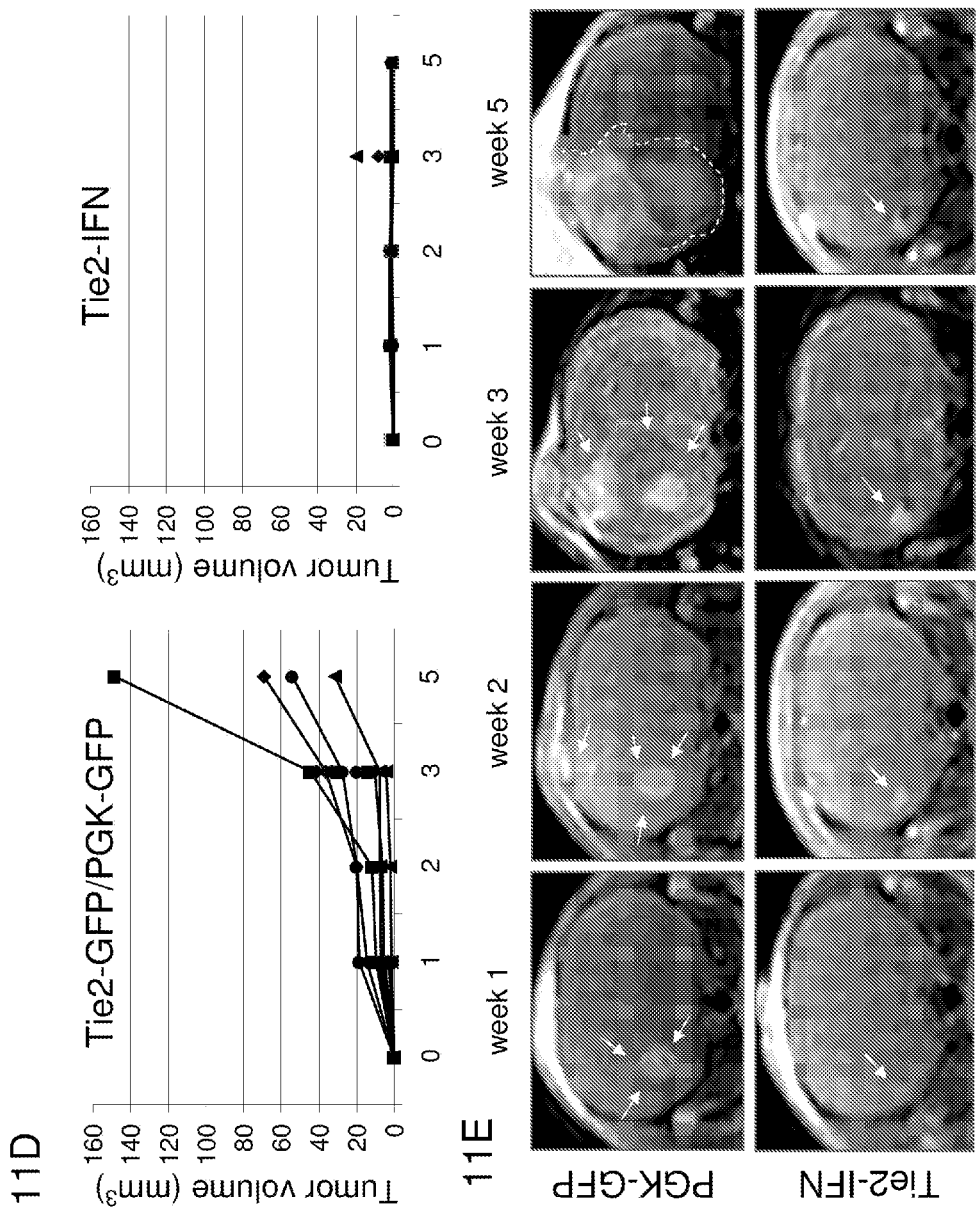
Figure 11:
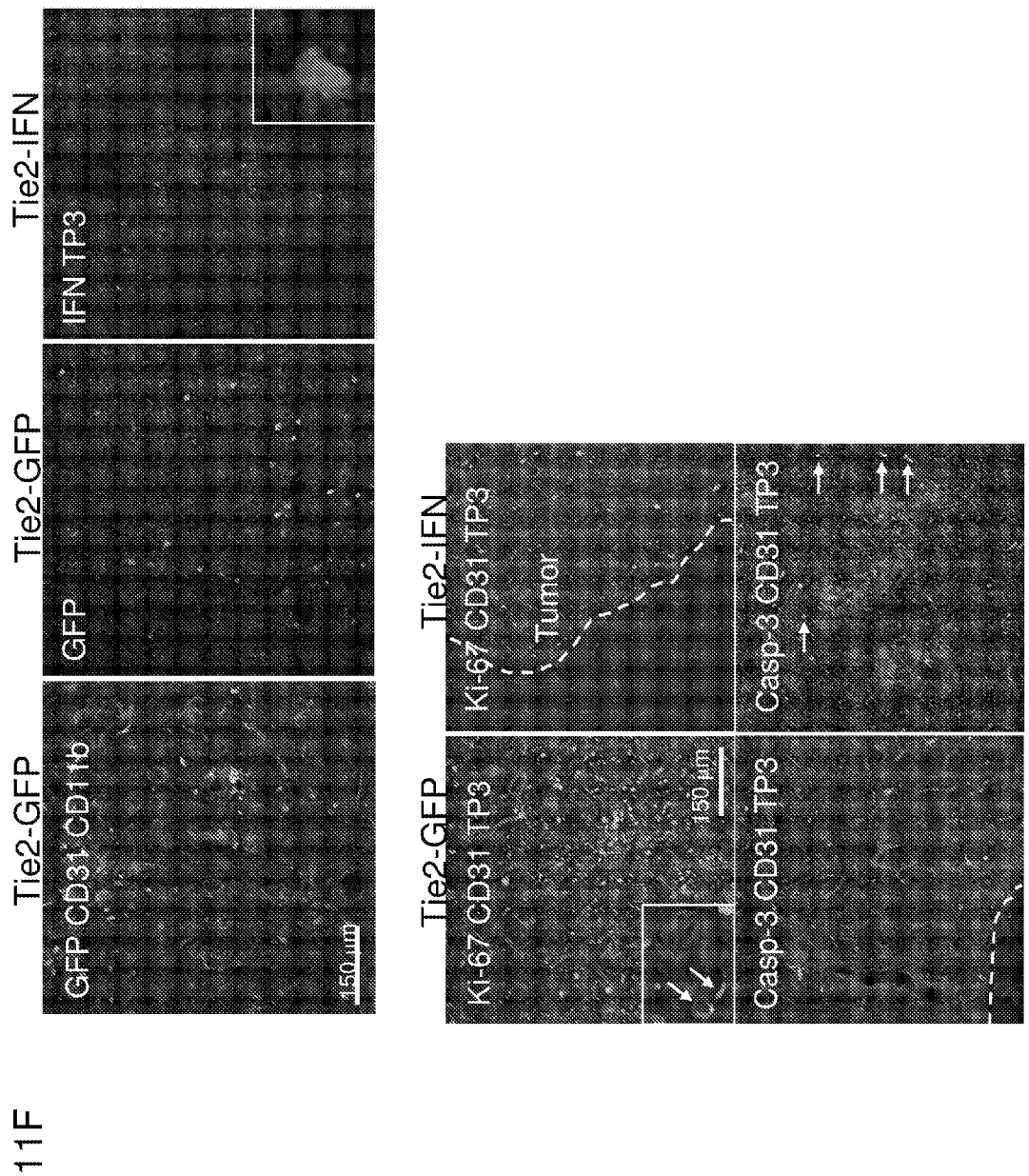
Figure 11:
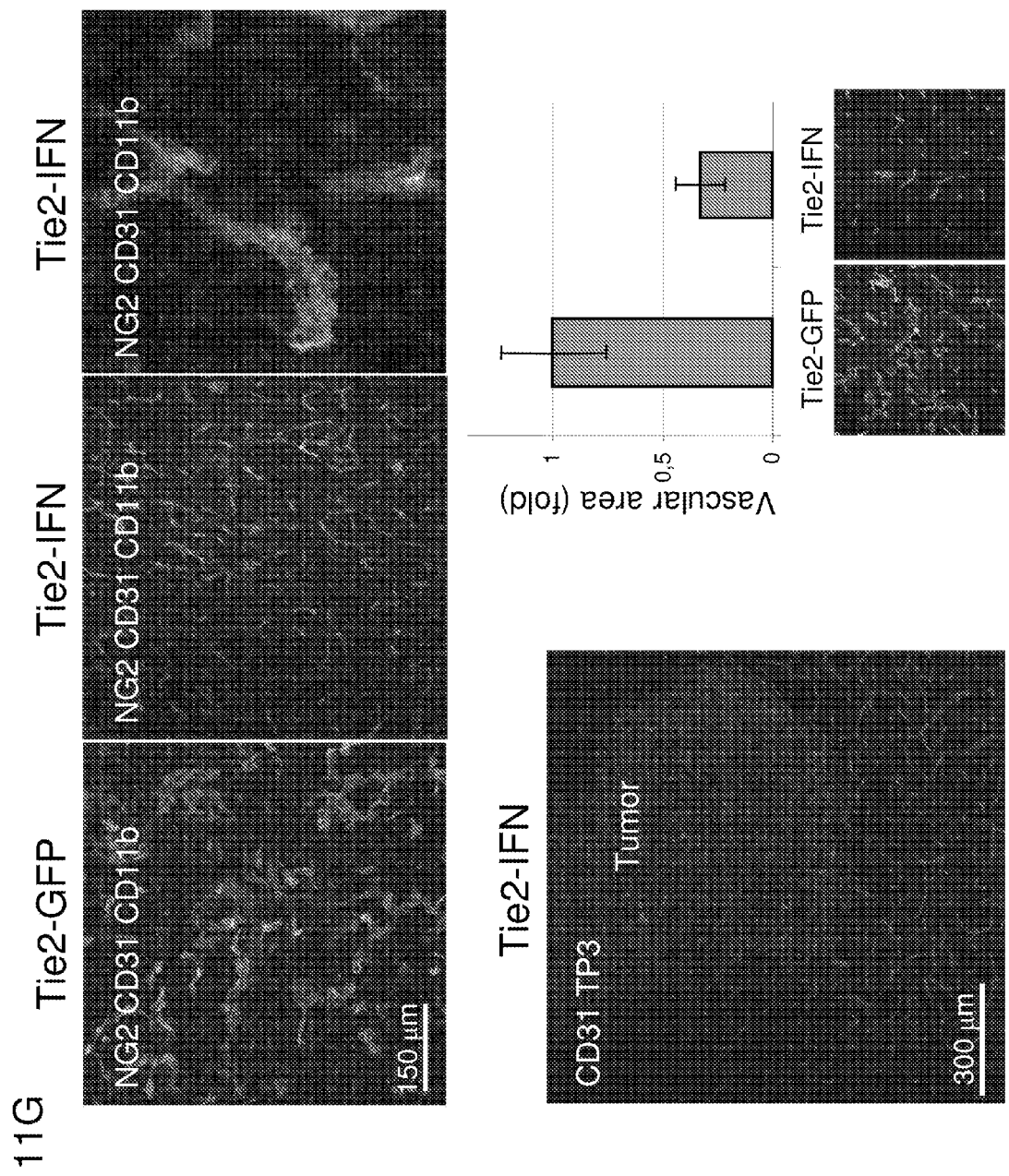
Figure 11:
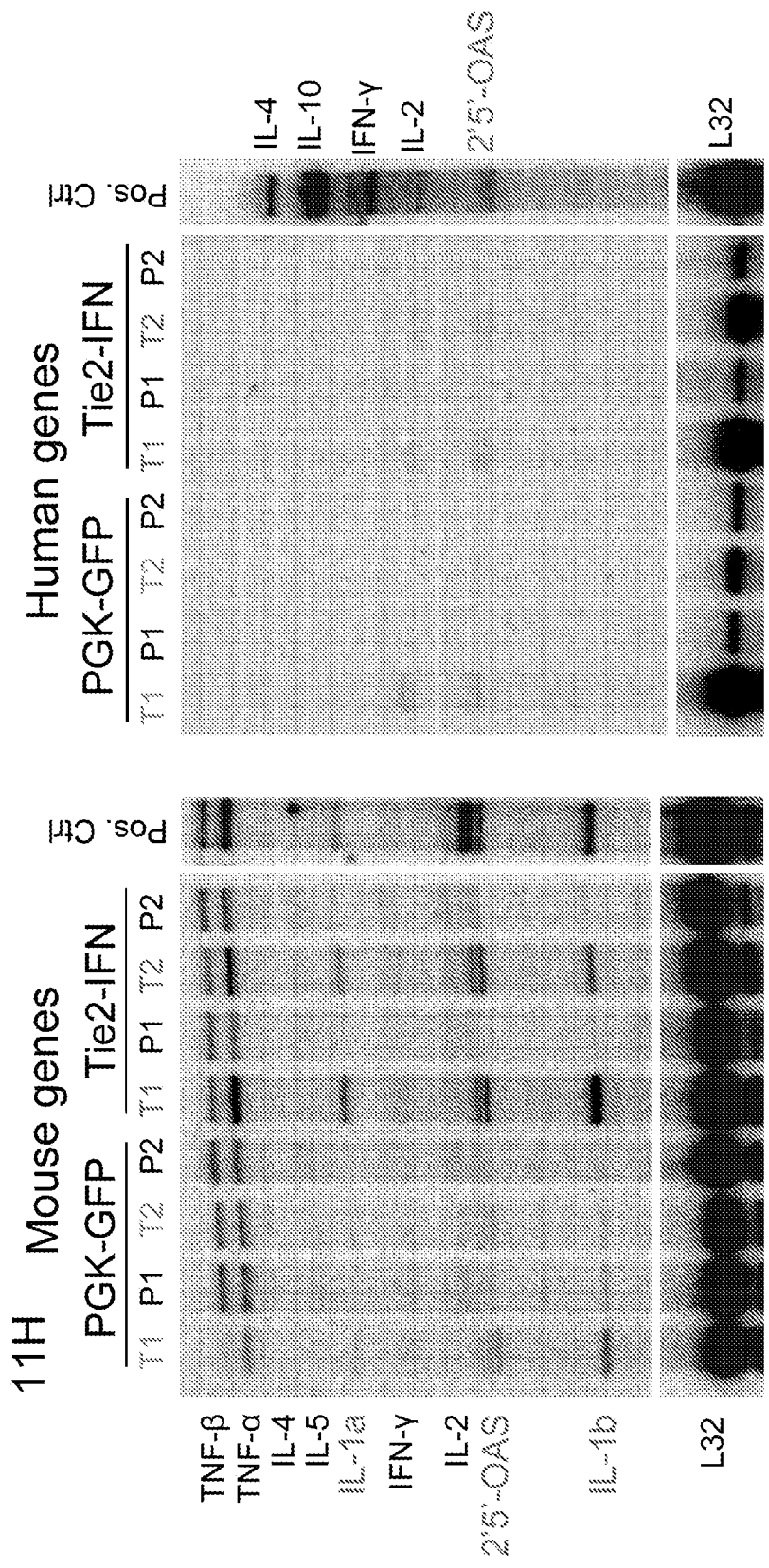
Figure 11:
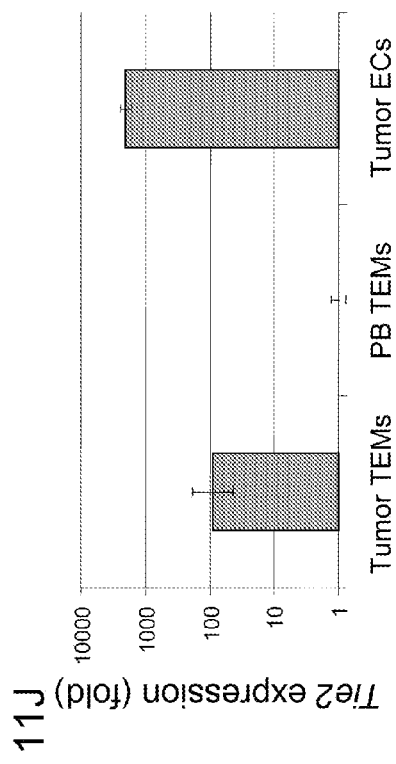

Mouse Tie2-Expressing Monocytes can be Used for Efficacious and Safe Delivery of Gene Therapy to Tumors We constructed late generation lentiviral vectors (LVs) expressing murine interferon-alpha1 (mIFN-$\alpha$). We cloned mIFN-$\alpha$ either under the control of the ubiquitously active phosphoglycerate kinase (PGK) promoter or of transcription regulatory sequences of the Tie2 gene, and obtained PGK-mIFN-$\alpha$ (PGK-IFN) and Tie2-mIFN-$\alpha$ (Tie2-IFN) LVs, respectively. We produced concentrated vectors, including control GFP-expressing LVs (PGK-GFP and Tie2-GFP), and transduced BM-derived hematopoietic stem/progenitor (HS/PCs) cells. HS/PCs transduced by PGK-IFN LVs efficiently produced IFN-$\alpha$ when grown in liquid culture, whereas cells transduced by Tie2-IFN LVs expressed IFN-$\alpha$ to a much lower extent, consistent with the low frequency of cells expressing Tie2 (and its low expression level) among HS/PCs and differentiating precursors (FIG. 11A). Although transduction of BM progenitors by PGK-IFN LVs did not inhibit their proliferation in vitro, it impaired their engraftment in recipient mice, which died 10-12 days after the transplant with overt BM aplasia (FIG. 11B). In contrast, mice transplanted with Tie2-IFN LV-transduced cells were successfully reconstituted by gene modified cells, as shown by Real Time PCR of vector sequences in BM cells several weeks after the transplant ($0.6 \pm 0.4$ LV copies/cell genome, n=8), and all survived long-term. Despite the long-term engraftment of gene modified cells, IFN-$\alpha$ was not detectable in the plasma of Tie2-IFN mice by ELISA. These results showed that the IFN-$\alpha$ transgene, when regulated by Tie2 regulatory sequences, did not interfere with long-term HS/PC engraftment and did not induce systemic over-expression of IFN-$\alpha$ from the reconstituted transgenic hematopoietic system. Thus, Tie2-IFN mice provide the means for testing TEM-mediated delivery of IFN-$\alpha$ to tumors. We analyzed the anti-tumor activity of TEM-released IFN-$\alpha$ in athymic mice intracranially inoculated with human gliomas. In this model, putative antitumor activity of IFN-$\alpha$ should primarily consist of direct inhibition of stromal, host-derived components of the tumor. In fact, athymic mice cannot mount adaptive immune responses and largely lack T lymphocytes, which are important components of antitumor responses mediated by IFNs. In addition, IFNs display species specificity of action and murine IFN-$\alpha$ does not effectively activate IFN responses in cells of human origin. Accordingly, we found that murine IFN-$\alpha$ secreted by LV-transduced cells potently inhibited the proliferation of murine cell lines (including tumor and ECs), but not of human glioma cells in vitro (FIG. 11C).

We injected human glioma cells in Tie2-IFN (n=10), Tie2-GFP (n=5) and PGK-GFP (n=7) mice, 8 weeks after the transplant of gene-modified HS/PCs, and monitored tumor growth by MRI for up to 5 weeks PTI (FIG. 11D). Tumor volumes were indistinguishable in control Tie2-GFP and PGK-GFP mice at 3 weeks PTI (average tumor volume$\pm$SEM: $24.6 \pm 4.3$ mm$^3$). In sharp contrast, tumor growth was dramatically inhibited in Tie2-IFN mice. At 3 weeks PTI, the median tumor volume was >6-fold lower in Tie2-IFN mice than in GFP mice ($3.8 \pm 2.1$ vs. $24.6 \pm 4.3$ mm$^3$, respectively; p<0.01). Moreover, by 5 weeks PTI (FIG. 11D), the majority of Tie2-IFN mice were either tumor-free or had tumors barely detectable by MRI (tumor volume$\leq 1$ mm$^3$) or histology, whereas all GFP mice had developed large tumors and were thereafter euthanized. Interestingly, tumors detectable in Tie2-IFN mice appeared more necrotic than those growing in GFP mice, as measured by MRI at 3 wks PTI (relative necrotic fraction, %$\pm$SEM: $22.9 \pm 6.6$ vs. $3.7 \pm 1.3$, respectively; p<0.01). These results showed that TEM-mediated release of IFN-$\alpha$ effectively inhibited human glioma growth in the mouse brain (FIG. 11D).

We then analysed tumor cell proliferation/apoptosis, angiogenesis and stromal composition of the tumors. In tumors of Tie2-GFP mice, GFP$^+$ TEMs mostly had a typical perivascular location (FIG. 11F). These TEMs were CD11b$^+$ but could be distinguished from the majority of tumor-associated macrophages (TAMs) based on their small, rounded shape, and their vicinity to newly formed blood vessels. Immunofluorescence staining using anti-IFN-$\alpha$ antibodies detected distinct IFN-$\alpha^+$ mononuclear cells in gliomas of Tie2-IFN, but not of control mice (FIG. 11F). In Tie2-IFN tumors, the frequency and distribution of IFN-$\alpha^+$ cells was similar to that of GFP$^+$ TEMs in control tumors, suggesting that the IFN-$\alpha^+$ cells represented bona fide IFN-producing TEMs. Compared to control tumors, Tie2-IFN tumors that grew sufficiently to be analyzed displayed decreased cell proliferation and greatly enhanced apoptosis (FIG. 11F).

There were striking differences in the vascularization of GFP and Tie2-IFN gliomas (FIG. 11G). Indeed, whereas the blood vessels of control tumors were notably enlarged and tortuous, those of Tie2-IFN tumors had small lumen and displayed a regular profile, often resembling brain parenchyma capillaries (FIG. 11G). Moreover, the relative vascular area of Tie2-IFN tumors was only 33% of that of GFP tumors. Intriguingly, the blood vessels of Tie2-IFN tumors were richly covered by NG2$^+$ pericytes, a typical feature of quiescent or "normalized" blood vessels (FIG. 11G), and contained fewer Ki-67$^+$ proliferating ECs and increased numbers of caspase-3$^+$ apoptotic cells than the blood vessels of control tumors (FIG. 11F above). Together, these findings strongly suggested that blood vessels of Tie2-IFN gliomas were in an antiangiogenic state.

We then analysed the expression of a panel of IFN-α-inducible genes. RNase protection assays performed using a set of mouse-specific probes showed that IFN responsive genes were strongly upregulated in the stromal compartment of Tie2-IFN gliomas, as compared to control tumors or brain tissue obtained from the contralateral, non-injected brain hemisphere (FIG. 11H). In particular, OAS1/2'5'-OAS, tumor necrosis factor-α (TNF-α) and interleukin-1α and -1β (IL-1α/β), all typical indicators of IFN-induced cytotoxic inflammation, were significantly upregulated in Tie2-IFN tumors. Interestingly, when we performed the same analysis using human-specific probes, we only detected little expression of 2'5'-OAS in Tie2-IFN tumors, indicating that the IFN pathway was minimally activated in the tumor cells (FIG. 11H). Thus, in this human glioma model, the IFN response was mainly targeted to the stromal components of the tumor. Taken together, these results indicated that we achieved effective antitumor activity even when the IFN response was specifically targeted to the tumor stroma, and suggested that stromal cells, rather than tumor cells, may represent the main target of type I IFNs during antitumor responses.

Clinical use of type I IFN has been hampered by significant myelotoxicity. To examine the potential hematopoietic toxicity of our IFN-α delivery strategy, we measured blood cell counts and composition in Tie2-IFN and control transplanted mice. Tie2-IFN mice showed no obvious hematopoietic alterations; indeed, red blood cell and platelet counts, hemoglobin and hematocrit were similar in Tie2-IFN and control mice, and were in the normal range (FIG. 11I). Moreover, IFN-α did not affect the frequency of colony-forming cells (CFCs) in the mouse BM, as assessed by CFC assays (data not shown). The lack of hematopoietic toxicity suggested that, in spite of the presence of BM and blood populations of Tie2-expressing cells (De Palma et al., 2005), IFN-α was not expressed to toxic levels in the hematopoietic tissues of Tie2-IFN mice. The preferential activation of Tie2 transcription regulatory sequences in tumors, possibly mediated by hypoxia or environmental differentiation cues, may contribute to this effect. To specifically address this issue, we compared the expression of Tie2 mRNA by qPCR in TEMs isolated from blood and tumors grown in Tie2-GFP transgenic mice. Tie2 expression was strongly upregulated (~100-fold) in tumor-derived TEMs, as compared to blood-derived TEMs (FIG. 11J). This finding highlighted a major and unanticipated mechanism contributing to the selectivity of IFN-α expression at the tumor site and, together with the tumor homing-specificity of TEMs, well explained both the effective antitumor activity and the lack of myelotoxicity observed in Tie2-IFN mice.

In order to better assess the advantages of targeted delivery, we compared the safety and efficacy of IFN-α delivery in a model of systemic administration. To this aim, we intravenously injected a group of CD1 athymic Tie2-GFP mice (n=4) with 10 μg p24-equivalents of PGK-IFN LVs, and obtained s-IFN mice. By intravenous injection, LVs preferentially transduce liver and spleen cells, where they establish a stable source of the transgene product.

Figure 11K:
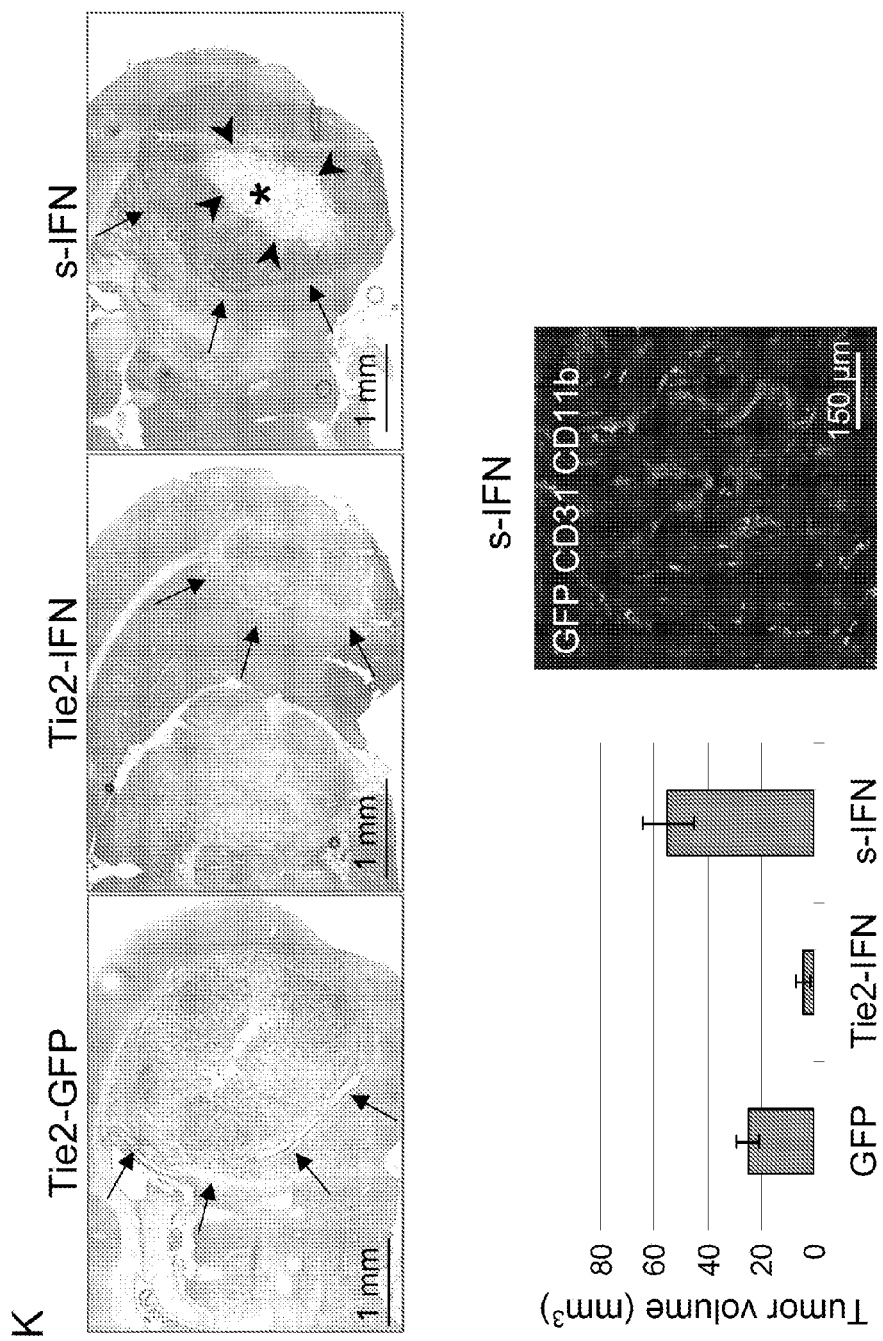

As expected, 3 weeks following LV injection s-IFN mice (n=4) expressed well-detectable levels of IFN-α in the plasma (418±124 pg/ml by ELISA). Despite the sustained IFN-α expression, tumor growth was not inhibited in s-IFN mice. Paradoxically, tumor volumes were significantly increased (~2-fold; p<0.01) in s-IFN as compared to GFP mice (n=12) at 3 wks PTI (FIG. 11K). In addition, s-IFN tumors were highly vascularized, with the blood vessels having the typical features of angiogenic vessels (FIG. 11K). Interestingly, systemic IFN-α did not affect the homing and perivascular localization of TEMs, nor the recruitment of other CD11b$^+$ myeloid cells to the tumors (FIG. 11K). However, MRI analysis and histology detected enhanced necrosis (p<0.001 versus GFP controls) and the presence of large central hemorrhage in all s-IFN tumors (FIG. 11K), the latter finding a likely consequence of the thrombocytopenic condition of these mice. Indeed, we found that s-IFN mice had much lower platelets and decreased red blood cells, hematocrit and hemoglobin, as compared to the other mice (FIG. 11I). These findings indicated that systemic IFN-α, as opposed to TEM-mediated delivery, significantly harmed hematopoiesis—and more markedly thrombopoiesis—in our experimental system. Moreover, systemic IFN-α induced progressive body weight loss in s-IFN mice (data not shown). In agreement with these observations, elevated doses of IFN-α have suppressive effects on hematopoiesis and are highly toxic in humans. Taken together, these results indicated that systemic IFN-α not only failed to restrict glioma growth, but also had significant myelotoxicity. In conclusion, our results showed that targeted IFN-α delivery by TEMs, but not ubiquitous expression in BM-derived cells or sustained expression in the plasma, achieved substantial antitumor activity in several mouse tumor models, without inducing hematopoietic toxicity.

In conclusion, targeted delivery of mIFN-α by TEMs achieved substantial anti-tumor activity in the absence of systemic toxicity, while ubiquitous expression in BM-derived cells or systemic delivery were not efficacious and were highly toxic. These results provide proof of principle of a new gene therapy paradigm in which ex vivo transduction of Bm-derived progenitors can be used to safely deliver potent anti-cancer molecules in a tumor-targeted fashion.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

REFERENCES

Arai, F., Hirao, A., Ohmura, M., Sato, H., Matsuoka, S., Takubo, K., Ito, K., Koh, G. Y., and Suda, T. (2004). Tie2/ angiopoietin-1 signaling regulates hematopoietic stem cell quiescence in the bone marrow niche. Cell 118, 149-161.

De Palma, M., Venneri, M. A., Galli, R., Sergi, L. S., Politi, L. S., Sampaolesi, M., and Naldini, L. (2005). Tie2 identifies a hematopoietic lineage of proangiogenic monocytes required for tumor vessel formation and a mesenchymal population of pericyte progenitors. Cancer Cell 8, 211-226.

Elsheikh, E., Uzunel, M., He, Z., Holgersson, J., Nowak, G., and Sumitran-Holgersson, S. (2005). Only a specific subset of human peripheral-blood monocytes has endothelial-like functional capacity. Blood 106, 2347-2355.

Gordon, S., and Taylor, P. R. (2005). Monocyte and macrophage heterogeneity. Nat Rev Immunol 5, 953-964.

Jones, N., Iljin, K., Dumont, D. J., and Alitalo, K. (2001). Tie receptors: new modulators of angiogenic and lymphangiogenic responses. Nat Rev Mol Cell Biol 2, 257-267.

Lemieux, C., Maliba, R., Favier, J., Theoret, J. F., Merhi, Y., and Sirois, M. G. (2005). Angiopoietins can directly activate endothelial cells and neutrophils to promote proinflammatory responses. Blood 105, 1523-1530.

Rafii, S., Lyden, D., Benezra, R., Hattori, K., and Heissig, B. (2002). Vascular and haematopoietic stem cells: novel targets for anti-angiogenesis therapy? Nat Rev Cancer 2, 826-835.

Taussig, D. C., Pearce, D. J., Simpson, C., Rohatiner, A. Z., Lister, T. A., Kelly, G., Luongo, J. L., Danet-Desnoyers, G. A., and Bonnet, D. (2005). Hematopoietic stem cells express multiple myeloid markers: implications for the origin and targeted therapy of acute myeloid leukemia. Blood 106, 4086-4092.

Wild, R., Ramakrishnan, S., Sedgewick, J., and Griffioen, A. W. (2000). Quantitative assessment of angiogenesis and tumor vessel architecture by computer-assisted digital image analysis: effects of VEGF-toxin conjugate on tumor microvessel density. Microvasc Res 59, 368-376.

The invention claimed is:

1. An isolated human monocyte cell expressing the following markers: Tie2 and CD14, wherein the cell does not express the following markers: CCR2 and VEGFR2.

2. The isolated human monocyte cell according to claim 1 expressing the following markers: Tie2, CD14 and CD16.

3. The isolated human monocyte cell according to claim 1 expressing the following markers: Tie2, CD14, CD16, CD115 and CD33.

4. The isolated human monocyte cell according to claim 1 expressing the following markers: Tie2, CD11b, CD14, CD16, CD45, CD115, CD33 and CCR5.

5. The isolated human monocyte cell according to claim 1 wherein the cell does not express the following markers: CCR2, CD19, CD3, CD62L and VEGFR2.

6. The isolated human monocyte cell according to claim 1 expressing the following markers: Tie2, CD11b, CD14, CD16, CD45, CD115, CD33 and CCR5; and wherein the cell does not express the following markers: CCR2, CD19, CD3, CD62L and VEGFR2.

7. The isolated human monocyte cell according to claim 1 wherein said cell is not a $CD14^{high}CD16^-$ classical monocyte.

8. A pharmaceutical composition comprising monocyte cells, wherein said monocyte cells consist essentially of monocyte cells as defined in claim 1, and a pharmaceutically acceptable carrier dilute or excipient.

9. The isolated monocyte cell as defined in claim 1 obtained from hematopoietic precursor cells.

10. An isolated human monocyte cell expressing the following markers: Tie2 and CD16, wherein the cell does not express the following markers: CCR2 and VEGFR2.

* * * * *